United States Patent
Yamano et al.

(10) Patent No.: US 8,952,185 B2
(45) Date of Patent: Feb. 10, 2015

(54) PRODUCTION METHOD OF OPTICALLY ACTIVE DIHYDROBENZOFURAN DERIVATIVE

(75) Inventors: Mitsuhisa Yamano, Osaka (JP); Mitsutaka Goto, Yamaguchi (JP); Takahiro Konishi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/985,395

(22) PCT Filed: Feb. 16, 2012

(86) PCT No.: PCT/JP2012/054337
§ 371 (c)(1),
(2), (4) Date: Sep. 11, 2013

(87) PCT Pub. No.: WO2012/111849
PCT Pub. Date: Aug. 23, 2012

(65) Prior Publication Data
US 2013/0345444 A1     Dec. 26, 2013

(30) Foreign Application Priority Data
Feb. 17, 2011 (JP) .................. 2011-032610

(51) Int. Cl.
| | |
|---|---|
| C07D 307/86 | (2006.01) |
| C07D 307/80 | (2006.01) |
| C07C 215/32 | (2006.01) |
| C07C 315/04 | (2006.01) |
| C07C 317/18 | (2006.01) |
| C07C 211/27 | (2006.01) |
| B01J 31/22 | (2006.01) |
| C07F 9/50 | (2006.01) |
| C07F 15/00 | (2006.01) |
| C07F 17/02 | (2006.01) |
| C07F 9/572 | (2006.01) |
| C07F 9/6568 | (2006.01) |

(52) U.S. Cl.
CPC .......... *B01J 31/2295* (2013.01); *C07C 211/27* (2013.01); *C07C 215/32* (2013.01); *C07C 315/04* (2013.01); *C07C 317/18* (2013.01); *C07D 307/80* (2013.01); *C07F 9/5018* (2013.01); *C07F 15/006* (2013.01); *C07F 17/02* (2013.01); *C07D 307/86* (2013.01); *C07B 2200/07* (2013.01); *C07F 9/5004* (2013.01); *C07F 9/5022* (2013.01); *C07F 9/5027* (2013.01); *C07F 9/5031* (2013.01); *C07F 9/5726* (2013.01); *C07F 9/5728* (2013.01); *C07F 9/65683* (2013.01)
USPC .............................. 549/462; 556/21; 568/33

(58) Field of Classification Search
None
See application file for complete search history.

(56) References Cited

U.S. PATENT DOCUMENTS

| | | |
|---|---|---|
| 2006/0258722 A1 | 11/2006 | Yasuma et al. |
| 2007/0149608 A1 | 6/2007 | Yasuma et al. |
| 2007/0155808 A1 | 7/2007 | Yasuma et al. |
| 2007/0213364 A1 | 9/2007 | Yasuma et al. |
| 2008/0269220 A1 | 10/2008 | Yasuma et al. |
| 2009/0012093 A1 | 1/2009 | Fukatsu et al. |
| 2010/0004312 A1 | 1/2010 | Yasuma et al. |
| 2010/0144806 A1 | 6/2010 | Yasuma et al. |

FOREIGN PATENT DOCUMENTS

| | | |
|---|---|---|
| WO | 2008/001931 | 1/2008 |
| WO | 2008/101197 | 8/2008 |
| WO | 2010/143733 | 12/2010 |

OTHER PUBLICATIONS

Nobuyuki Negoro et al., "Discovery of TAK-875: A Potent, Selective, and Orally Bioavailable GPR40 Agonist", ACS Medicinal Chemistry Letters, Jun. 18, 2010, 1(6), pp. 290-294.
B. Bachiller-Baeza et al., "Ruthenium-Supported Catalysts for the Stereoselective Hydrogenation of Paracetamol to 4-*trans*-acetamidocyclohexanol: Effect of Support, Metal Precursor, and Solvent", (Abstract), Jan. 2005, Journal of Catalysis, vol. 229, Issue 2.
Kathelyne Everaere et al., "Stereoselective Synthesis of 3-substituted Phtalides Via Asymmetric Transfer Hydrogenation Using Well-Defined Ruthenium Catalysts Under Neutral Conditions", (Abstract), Mar. 2001, Tetrahedron Letters, vol. 42, Issue 10.
International Search Report issued Jul. 27, 2012 in International (PCT) Application No. PCT/JP2012/054337.
W. Tang et al., "New Chiral Phosphorus Ligands for Enantioselective Hydrogenation", Chemical Reviews, American Chemical Society, vol. 103, pp. 3029-3069, Jan. 1, 2003.
N. Ortega et al., "Ruthenium NHC Catalyzed Highly Asymmetric Hydrogenation of Benzofurans", Angewandte Chemie International Edition, vol. 51, No. 7, pp. 1710-1713, Jan. 3, 2012.
M. J. Burk, $C_2$-Symmetric Bis(Phospholanes) and Their Use in Highly Enantioselective Hydrogenation Reactions, J. Am. Chem. Soc., vol. 113, pp. 8518-8519, 1991.

*Primary Examiner* — Sun Jae Yoo
(74) *Attorney, Agent, or Firm* — Wenderoth, Lind & Ponack, L.L.P.

(57) ABSTRACT

Provided is a production method of an optically active dihydrobenzofuran derivative. A production method of an optically active form of a compound represented by the formula: wherein each symbol is as defined in the specification, or a salt thereof and the like.

(X)

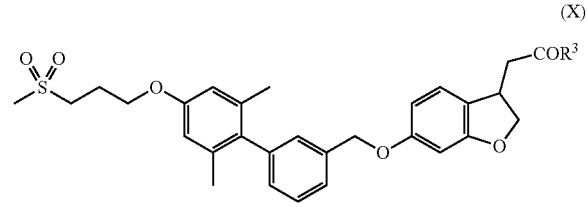

1 Claim, 3 Drawing Sheets

PRODUCTION METHOD OF OPTICALLY ACTIVE DIHYDROBENZOFURAN DERIVATIVE

TECHNICAL FIELD OF THE INVENTION

The present invention relates to a production method of an optically active dihydrobenzofuran derivative and the like.

BACKGROUND OF THE INVENTION

A compound having an optically active dihydrobenzofuran ring (e.g., [(3S)-6-({2',6'-dimethyl-4'-[3-(methylsulfonyl)propoxy]biphenyl-3-yl}methoxy)-2,3-dihydro-1-benzofuran-3-yl]acetic acid) as a GPR40 receptor agonist useful as a drug for the prophylaxis or treatment of diabetes and the like, and a production method thereof (WO2008/001931).

SUMMARY OF THE INVENTION

Problems to be Solved by the Invention

The aforementioned compound has an optically active dihydrobenzofuran ring, and there is a demand for a convenient production method of an optically active dihydrobenzofuran derivative. Accordingly, it is an object of the present invention to provide a production method of an optically active dihydrobenzofuran derivative, and the like.

Means of Solving the Problems

The present inventors have conducted intensive studies and found a production method of an optically active dihydrobenzofuran derivative, which is convenient and has high stereoselectivity, which resulted in the completion of the present invention.

Accordingly, the present invention relates to

[1] a method of producing an optically active form of a compound represented by the formula:

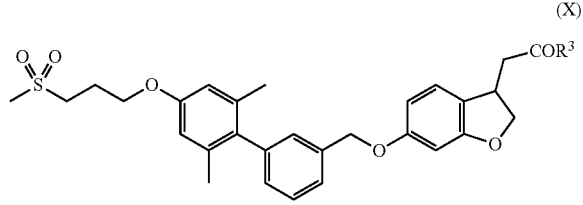

(X)

wherein $R^3$ is a hydroxy group or an optionally substituted $C_{1-6}$ alkoxy group,
or a salt thereof (hereinafter to be also referred to as compound (X)), comprising a step of producing an optically active form of a compound represented by the formula:

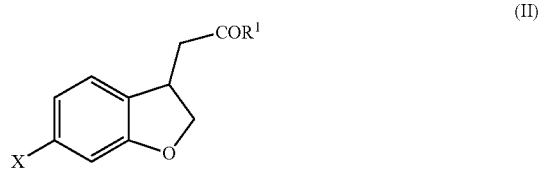

(II)

wherein $R^1$ is a hydroxy group or an optionally substituted $C_{1-6}$ alkoxy group; and
X is a halogen atom, a hydroxy group or an optionally substituted $C_{1-6}$ alkoxy group,
or a salt thereof (hereinafter to be also referred to as compound (II)) by subjecting a compound represented by the formula:

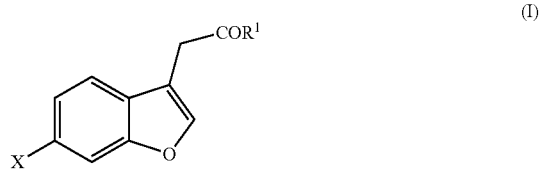

(I)

wherein each symbol is as defined above,
or a salt thereof (hereinafter to be also referred to as compound (I)) to an asymmetric hydrogenation reaction in the presence of a ruthenium complex;
[2] the production method according to the aforementioned [1], wherein the ruthenium complex comprises a compound represented by the formula:

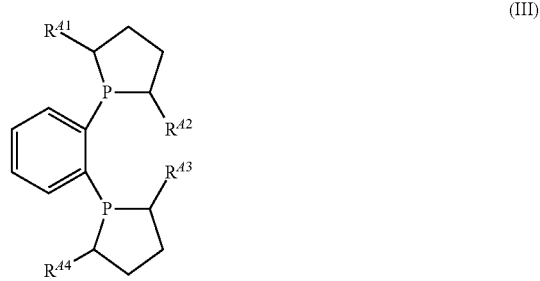

(III)

wherein $R^{A1}$, $R^{A2}$, $R^{A3}$ and $R^{A4}$ are each independently an optionally substituted hydrocarbon group (hereinafter to be also referred to as compound (III)) as a ligand;
[3] the production method according to the aforementioned [1] or [2], wherein $R^1$ is a hydroxy group;
[4] the production method according to any one of the aforementioned [1] to [3], further comprising a step of adding (1) an optically active form of a compound represented by the formula:

(IVa1)

wherein $R^{B1a}$ is an optionally substituted $C_{6-14}$ aryl group or an optionally substituted $C_{7-13}$ aralkyl group; and
$R^{B4}$ is an optionally substituted $C_{1-6}$ alkyl group, or a salt thereof (hereinafter to be also referred to as compound (IVa1)), or
(2) an optically active form of a compound represented by the formula:

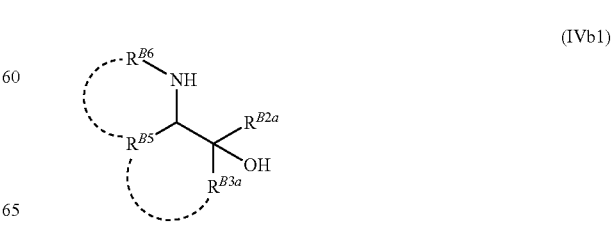

(IVb1)

wherein $R^{B2a}$ is a hydrogen atom or an optionally substituted $C_{6-14}$ aryl group;
$R^{B3a}$ is an optionally substituted $C_{6-14}$ aryl group or an optionally substituted $C_{1-6}$ alkyl group;
$R^{B5}$ is an optionally substituted $C_{1-6}$ alkyl group or an optionally substituted $C_{6-14}$ aryl group;
$R^{B6}$ is a hydrogen atom or an optionally substituted $C_{1-6}$ alkyl group; or
$R^{B3a}$ and $R^{B5}$ optionally form, together with the adjacent carbon atom, an optionally substituted 4- to 6-membered ring (said 4- to 6-membered ring is optionally fused with an optionally substituted benzene ring); or
$R^{B5}$ and $R^{B6}$ optionally form, together with the adjacent nitrogen atom and carbon atom, an optionally substituted 4- to 6-membered ring,
or a salt thereof (hereinafter to be also referred to as compound (IVb1));
[5] the production method according to any one of the aforementioned [1] to [4], wherein an organic base of a salt of a compound represented by the formula:

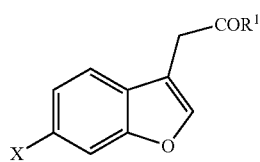
(I)

wherein each symbol is as defined above, is
(1) an optically active form of a compound represented by the formula:

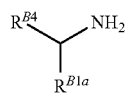
(IVa1)

wherein $R^{B1a}$ is an optionally substituted $C_{6-14}$ aryl group or an optionally substituted $C_{7-13}$ aralkyl group; and
$R^{B4}$ is an optionally substituted $C_{1-6}$ alkyl group, or
(2) an optically active form of a compound represented by the formula:

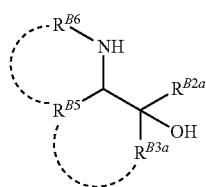
(IVb1)

wherein $R^{B2a}$ is a hydrogen atom or an optionally substituted $C_{6-14}$ aryl group;
$R^{B3a}$ is an optionally substituted $C_{6-14}$ aryl group or an optionally substituted $C_{1-6}$ alkyl group;
$R^{B5}$ is an optionally substituted $C_{1-6}$ alkyl group or an optionally substituted $C_{6-14}$ aryl group;
$R^{B6}$ is a hydrogen atom or an optionally substituted $C_{1-6}$ alkyl group; or
$R^{B3a}$ and $R^{B5}$ optionally form, together with the adjacent carbon atom, an optionally substituted 4- to 6-membered ring (said 4- to 6-membered ring is optionally fused with an optionally substituted benzene ring); or
$R^{B5}$ and $R^{B6}$ optionally form, together with the adjacent nitrogen atom and carbon atom, an optionally substituted 4- to 6-membered ring;
[6] the production method according to any one of the aforementioned [2] to [5], wherein $R^{A1}$, $R^{A2}$, $R^{A3}$ and $R^{A4}$ are each an isopropyl group;
[7] the production method according to any one of the aforementioned [1] to [6], wherein the ruthenium complex is a complex represented by the formula:

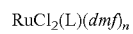
$$RuCl_2(L)(dmf)_n \quad (V)$$

wherein L is an optically active form of 1,2-bis(2,5-diisopropylphosphorano)benzene;
dmf is N,N-dimethylformamide; and,
n is an integer of one or more,
(hereinafter to be also referred to as compound (V));
[8] the production method according to the aforementioned [4] or [5], wherein $R^{B1a}$, $R^{B2a}$ and $R^{B3a}$ are each a phenyl group, $R^{B4}$ and $R^{B5}$ are each independently a $C_{1-6}$ alkyl group, and
$R^{B6}$ is a hydrogen atom;
[9] a salt of an optically active form of a compound represented by the formula:

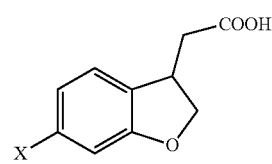
(VI)

wherein X is a halogen atom, a hydroxy group or an optionally substituted $C_{1-6}$ alkoxy group (hereinafter to be also referred to as compound (VI)),
wherein an organic base of the salt is
(1) an optically active form of a compound represented by the formula:

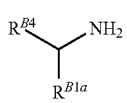
(IVa1)

wherein $R^{B1a}$ is an optionally substituted $C_{6-14}$ aryl group or an optionally substituted $C_{7-13}$ aralkyl group; and
$R^{B4}$ is an optionally substituted $C_{1-6}$ alkyl group, or
(2) an optically active form of a compound represented by the formula:

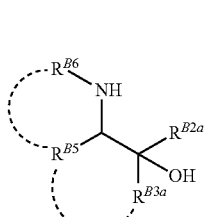
(IVb1)

wherein $R^{B2a}$ is a hydrogen atom or an optionally substituted $C_{6-14}$ aryl group;

$R^{B3a}$ is an optionally substituted $C_{6-14}$ aryl group or an optionally substituted $C_{1-6}$ alkyl group;

$R^{B5}$ is an optionally substituted $C_{1-6}$ alkyl group or an optionally substituted $C_{6-14}$ aryl group;

$R^{B6}$ is a hydrogen atom or an optionally substituted $C_{1-6}$ alkyl group; or $R^{B3a}$ and $R^{B5}$ optionally form, together with the adjacent carbon atom, an optionally substituted 4- to 6-membered ring (said 4- to 6-membered ring is optionally fused with an optionally substituted benzene ring); or $R^{B5}$ and $R^{B6}$ optionally form, together with the adjacent nitrogen atom and carbon atom, an optionally substituted 4- to 6-membered ring;

[10] the salt according to the aforementioned [9], which is represented by the formula:

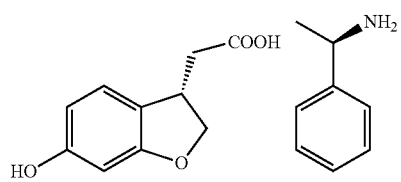
(VIIa)

(hereinafter to be also referred to as compound (VIIa));

[11] the salt according to the aforementioned [9], which is represented by the formula:

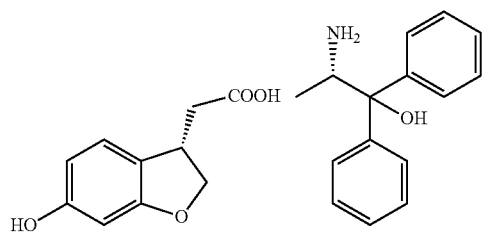
(VIIb)

(hereinafter to be also referred to as compound (VIIb);

[12] a ruthenium complex represented by the formula:

$$RuCl_2(L)(dmf)_n \qquad (V)$$

wherein L is an optically active form of 1,2-bis(2,5-diisopropylphosphorano)benzene;

dmf is N,N-dimethylformamide; and, n is an integer of one or more;

[13] a method of producing an optically active form of a compound represented by the formula:

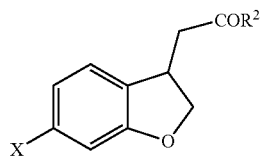
(VIII)

wherein $R^2$ is a $C_{1-6}$ alkoxy group; and other symbols are as defined above, or a salt thereof (hereinafter to be also referred to as compound (VIII)), comprising a step of esterifying the salt according to the aforementioned [9];

[14] a method of producing an optically active form of a compound represented by the formula:

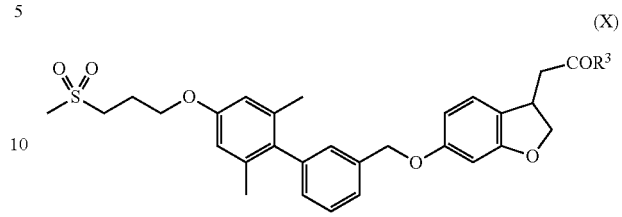
(X)

wherein $R^3$ is a hydroxy group or an optionally substituted $C_{1-6}$ alkoxy group, or a salt thereof, comprising a step of reacting a compound represented by the formula:

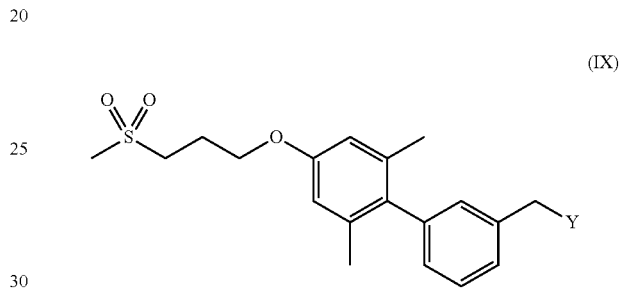
(IX)

wherein Y is a leaving group, or a salt thereof (hereinafter to be also referred to as compound (IX)) with an optically active form of a compound represented by the formula:

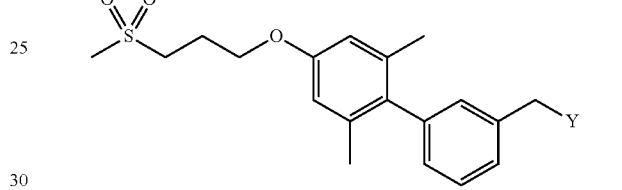
(VIIIa)

wherein $R^3$ is as defined above, or a salt thereof (hereinafter to be also referred to as compound (VIIIa));

[15] a compound represented by the formula:

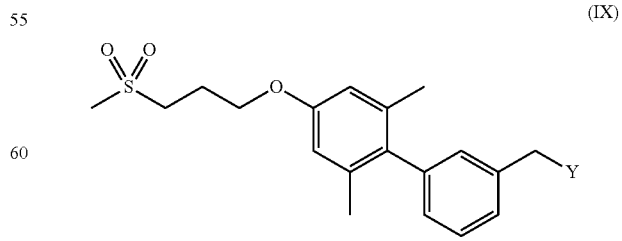
(IX)

wherein Y is a leaving group, or a salt thereof;

[16] a method of producing an optically active form of a compound represented by the formula:

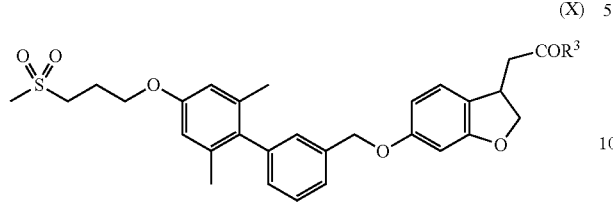

wherein $R^3$ is a hydroxy group or an optionally substituted $C_{1-6}$ alkoxy group,
or a salt thereof, comprising a step of producing a compound represented by the formula:

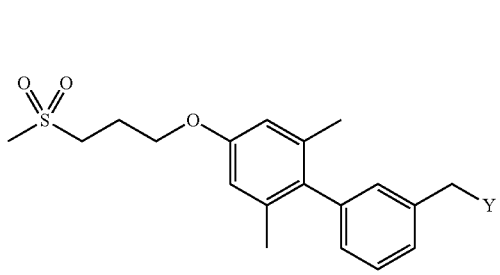

wherein Y is a leaving group,
or a salt thereof, by converting a compound represented by the formula:

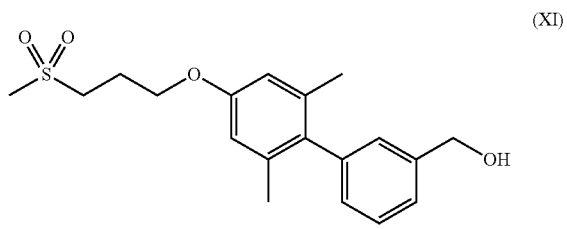 [SMILES: Cc1cc(OCCCS(C)(=O)=O)cc(C)c1-c1cccc(CO)c1]

or a salt thereof (hereinafter to be also referred to as compound (XI));

[17] a method of producing an optically active form of a compound represented by the formula:

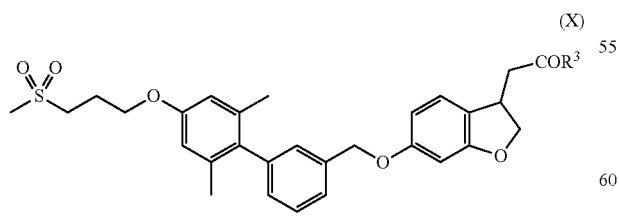

wherein $R^3$ is a hydroxy group or an optionally substituted $C_{1-6}$ alkoxy group,
or a salt thereof, comprising a step of producing a compound represented by the formula:

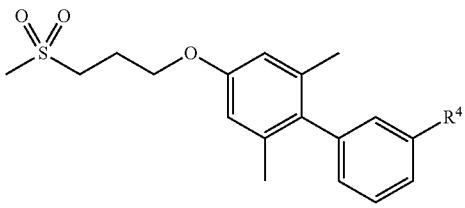

wherein $R^4$ is a formyl group or a hydroxymethyl group,
or a salt thereof (hereinafter to be also referred to as compound (XIV)) by reacting a compound represented by the formula:

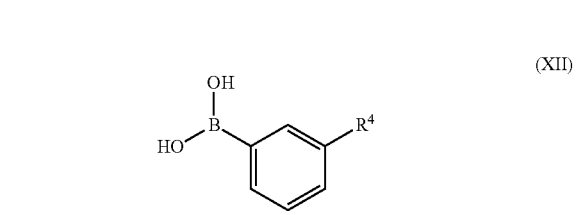

wherein each symbol is as defined above,
or a salt thereof (hereinafter to be also referred to as compound (XII)) with a compound represented by the formula:

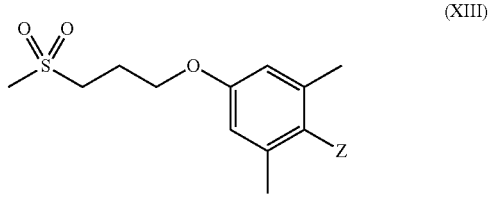

wherein Z is a halogen atom,
or a salt thereof (hereinafter to be also referred to as compound (XIII)) in the presence of a palladium catalyst;

[18] a compound represented by the formula:

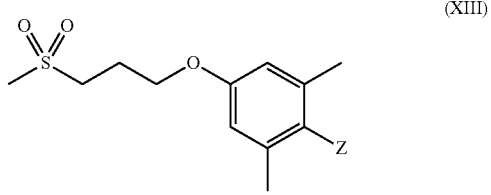

wherein Z is a halogen atom,
or a salt thereof;

[19] the production method according to the aforementioned [14], comprising (1) a step of producing an optically active form of a compound represented by the formula:

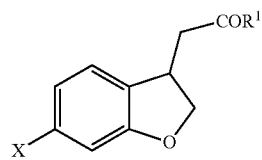
(II)

wherein each symbol is as defined above, or a salt thereof by subjecting a compound represented by the formula:

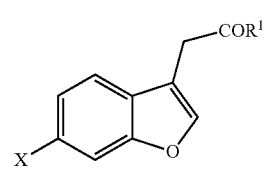
(I)

wherein each symbol is as defined above, or a salt thereof to an asymmetric hydrogenation reaction in the presence of a ruthenium complex;

(2) a step of producing a compound represented by the formula:

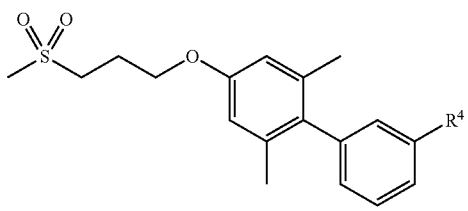
(XIV)

wherein each symbol is as defined above, or a salt thereof, by reacting a compound represented by the formula:

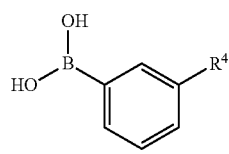
(XII)

wherein each symbol is as defined above, or a salt thereof, with a compound represented by the formula:

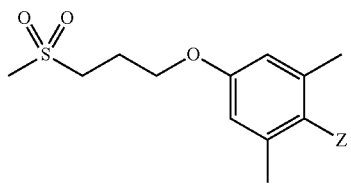
(XIII)

wherein each symbol is as defined above, or a salt thereof, in the presence of a palladium catalyst; and (3) a step of producing a compound represented by the formula:

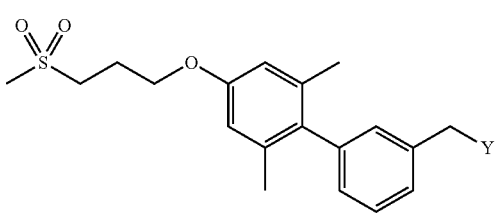
(IX)

wherein each symbol is as defined above, or a salt thereof, by converting a compound represented by the formula:

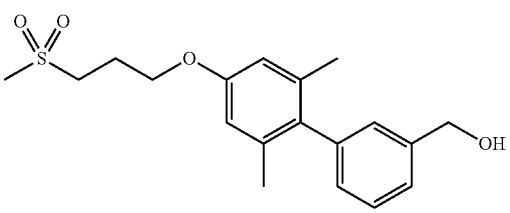
(XI)

or a salt thereof;

[20] a method of producing an optically active form of a compound represented by the formula:

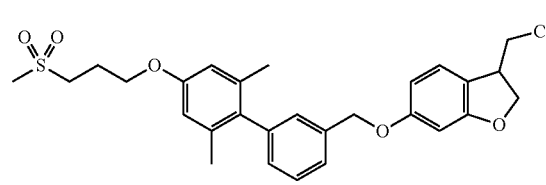
(X)

wherein $R^3$ is a hydroxy group or an optionally substituted $C_{1-6}$ alkoxy group, or a salt thereof, comprising a step of subjecting a compound represented by the formula:

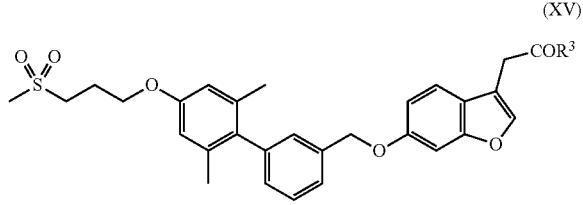

(XV)

wherein each symbol is as defined above,
or a salt thereof (hereinafter to be also referred to as compound (XV)) to an asymmetric hydrogenation reaction in the presence of a transition metal complex;

[21] a crystal of [(3S)-6-({2',6'-dimethyl-4'-[3-(methylsulfonyl)propoxy]biphenyl-3-yl}methoxy)-2,3-dihydro-1-benzofuran-3-yl]acetic acid, showing a powder X-ray diffraction pattern having characteristic peaks at lattice spacing (d) of about 19.24±0.2, 18.79±0.2, 6.35±0.2, 5.37±0.2, 4.91±0.2 and 4.83±0.2 angstroms by powder X-ray diffraction;

[22] a method of producing an optically active form of a compound represented by the formula:

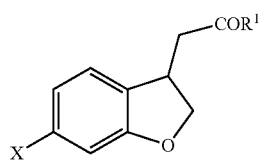

(II)

wherein $R^1$ is a hydroxy group or an optionally substituted $C_{1-6}$ alkoxy group; and
X is a halogen atom, a hydroxy group or an optionally substituted $C_{1-6}$ alkoxy group,
or a salt thereof, comprising a step of subjecting a compound represented by the formula:

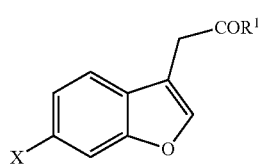

(I)

wherein each symbol is as defined above,
or a salt thereof, to an asymmetric hydrogenation reaction in the presence of a ruthenium complex;

[23] a method of producing an optically active form of a compound represented by the formula:

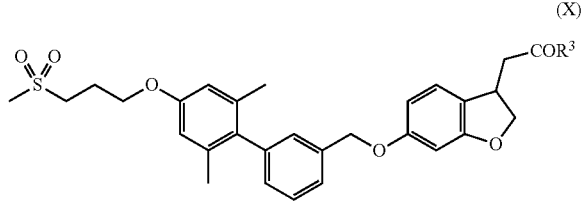

(X)

wherein $R^3$ is a hydroxy group or an optionally substituted $C_{1-6}$ alkoxy group, or a salt thereof, comprising a step of reacting a compound represented by the formula:

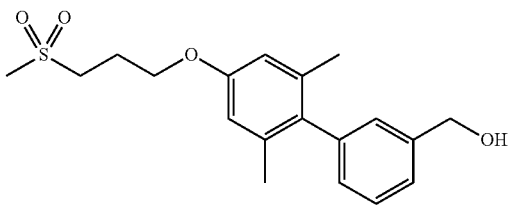

(XI)

or a salt thereof, with an optically active form of a compound represented by the formula:

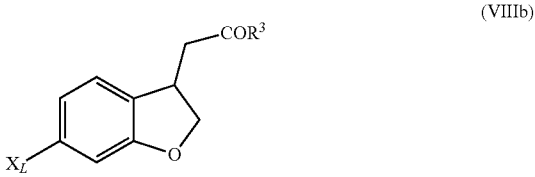

(VIIIb)

wherein $R^3$ is as defined above; and
$X_L$ is a leaving group,
or a salt thereof (hereinafter to be also referred to as compound (VIIIb));

[24] the production method according to any one of the aforementioned [1] to [9] and [13], comprising the step of the aforementioned [14];

[25] the production method according to any one of the aforementioned [1] to [9] and [13], comprising the step of the aforementioned [16];

[26] the production method according to any one of the aforementioned [1] to [9] and [13], comprising the step of the aforementioned [17];

[27] the production method according to any one of the aforementioned [1] to [9] and [13], comprising the steps of the aforementioned [14] and [16];

[28] the production method according to any one of the aforementioned [1] to [9] and [13], comprising the steps of the aforementioned [14] and [17];

[29] the production method according to any one of the aforementioned [1] to [9] and [13], comprising the steps of the aforementioned [16] and [17];

[30] the production method according to the aforementioned [14], comprising the step of the aforementioned [16];

[31] the production method according to the aforementioned [14], comprising the step of the aforementioned [17];

[32] the production method according to the aforementioned [14], comprising the steps of the aforementioned [16] and [17];

[33] the production method according to the aforementioned [16], comprising the step of the aforementioned [17];

[34] the production method according to any one of the aforementioned [24] to [29], wherein the ruthenium complex comprises an optically active form of a compound represented by the formula:

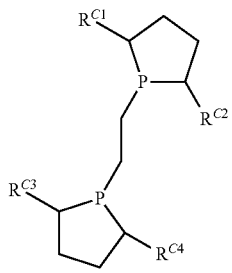 (IIIa)

wherein $R^{C1}$, $R^{C2}$, $R^{C3}$ and $R^{C4}$ are each independently an optionally substituted hydrocarbon group, as a ligand;

[35] the production method according to the aforementioned [34], wherein $R^{C1}$, $R^{C2}$, $R^{C3}$ and $R^{C4}$ are each independently a methyl group;

[36] a ruthenium complex represented by the formula:

$$RuCl_2(La)(dmf)_n \quad (Va)$$

wherein La is an optically active form of 1,2-bis(2,5-diethylphosphorano)benzene, or an optically active form of 1,2-bis(2,5-dimethylphosphorano)ethane;

dmf is N,N-dimethylformamide; and, n is an integer of one or more;

and the like.

In addition, the present invention relates to

[1A] a method of producing an optically active form of a compound represented by the formula:

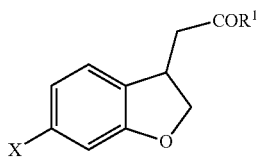 (II)

wherein $R^1$ is a hydroxy group or an optionally substituted $C_{1-6}$ alkoxy group; and X is a halogen atom, a hydroxy group or an optionally substituted $C_{1-6}$ alkoxy group, or a salt thereof, comprising a step of subjecting a compound represented by the formula:

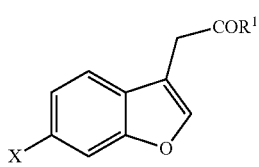 (I)

wherein each symbol is as defined above, or a salt thereof to an asymmetric hydrogenation reaction in the presence of a ruthenium complex;

[2A] the production method according to the aforementioned [1A], wherein the ruthenium complex comprises a compound represented by the formula:

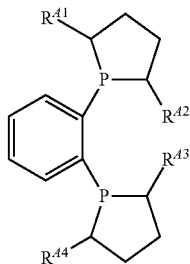 (III)

wherein $R^{41}$, $R^{42}$, $R^{43}$ and $R^{44}$ are each independently an optionally substituted hydrocarbon group, as a ligand;

[3A] the production method according to the aforementioned [1A] or [2A], wherein $R^1$ is a hydroxy group;

[4A] the production method according to any one of the aforementioned [1A] to [3A], further comprising a step of adding (1) an optically active form of a compound represented by the formula:

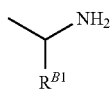 (IVa)

wherein $R^{B1}$ is an optionally substituted $C_{6-14}$ aryl group, or a salt thereof (hereinafter to be also referred to as compound (IVa)), or (2) an optically active form of a compound represented by the formula:

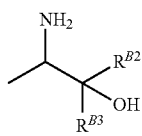 (IVb)

wherein $R^{B2}$ and $R^{B3}$ are each independently an optionally substituted $C_{6-14}$ aryl group, or a salt thereof (hereinafter to be also referred to as compound (IVb));

[5A] the production method according to any one of the aforementioned [1A] to [4A], wherein the organic base of a salt of a compound represented by the formula:

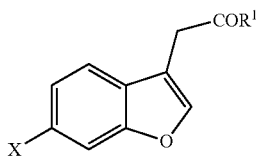 (I)

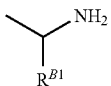
(IVa)

wherein each symbol is as defined above, or (2) an optically active form of a compound represented by the formula:

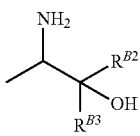
(IVb)

wherein each symbol is as defined above;

[6A] the production method according to any one of the aforementioned [2A] to [5A], wherein $R^{A1}$, $R^{A2}$, $R^{A3}$ and $R^{A4}$ are each an isopropyl group;

[7A] the production method according to any one of the aforementioned [1A] to [6A], wherein the ruthenium complex is a complex represented by the formula:

$$RuCl_2(L)(dmf)_n \quad (V)$$

wherein L is an optically active form of 1,2-bis(2,5-diisopropylphosphorano)benzene;

dmf is N,N-dimethylformamide; and, n is an integer of one or more;

[8A] the production method according to the aforementioned [4A] or [5A], wherein $R^{B1}$, $R^{B2}$ and $R^{B3}$ are each independently phenyl;

[9A] a salt of an optically active form of a compound represented by the formula:

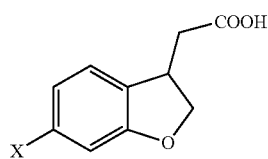
(VI)

wherein X is a halogen atom, a hydroxy group or an optionally substituted $C_{1-6}$ alkoxy group, wherein an organic base of the salt is (1) an optically active form of a compound represented by the formula:

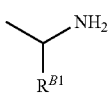
(IVa)

wherein $R^{B1}$ is an optionally substituted $C_{6-14}$ aryl group, or (2) an optically active form of a compound represented by the formula:

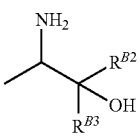
(IVb)

wherein $R^{B2}$ and $R^{B3}$ are each independently an optionally substituted $C_{6-14}$ aryl group;

[10A] the salt according to the aforementioned [9A], which is represented by the formula:

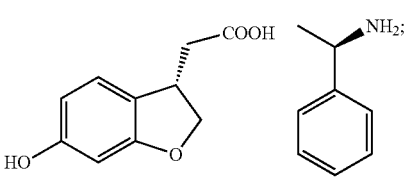
(VIIa)

[11A] the salt according to the aforementioned [9A], which is represented by the formula:

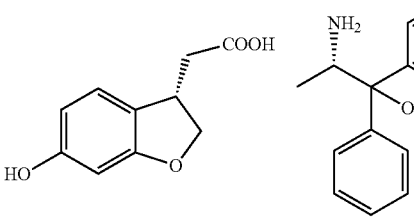
(VIIb)

[12A] a ruthenium complex represented by the formula:

$$RuCl_2(L)(dmf)_n \quad (V)$$

wherein L is an optically active form of 1,2-bis(2,5-diisopropylphosphorano)benzene;

dmf is N,N-dimethylformamide; and, n is an integer of one or more;

[13A] a method of producing an optically active form of a compound represented by the formula:

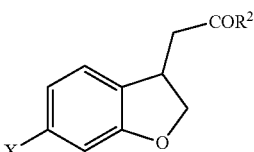
(VIII)

wherein $R^2$ is a $C_{1-6}$ alkoxy group; and and other symbols are as defined above, or a salt thereof, comprising a step of esterifying the salt according to the aforementioned [9A];

[14A] a method of producing an optically active form of a compound represented by the formula:

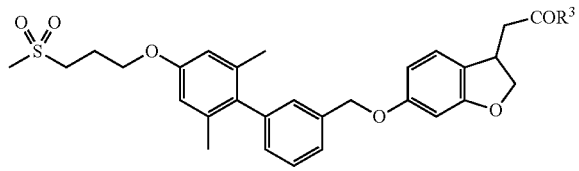

wherein R[3] is a hydroxy group or an optionally substituted C[1-6] alkoxy group, or a salt thereof, comprising a step of reacting a compound represented by the formula:

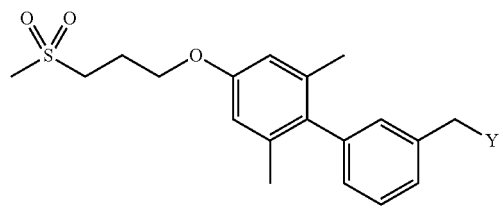

wherein Y is a halogen atom, or a salt thereof, with an optically active form of a compound represented by the formula:

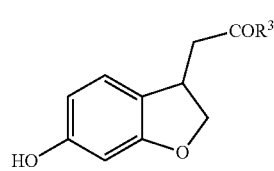

wherein each symbol is as defined above, or a salt thereof;

[15A] a compound represented by the formula:

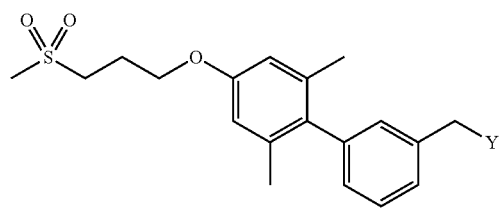

wherein Y is a halogen atom, or a salt thereof;

[16A] a method of producing a compound represented by the formula:

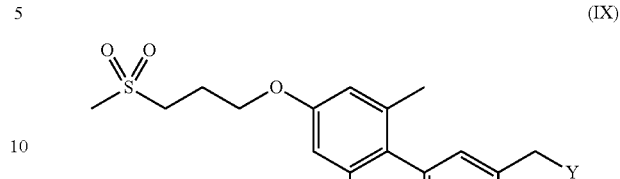

wherein Y is a halogen atom, or a salt thereof, comprising a step of halogenating a compound represented by the formula:

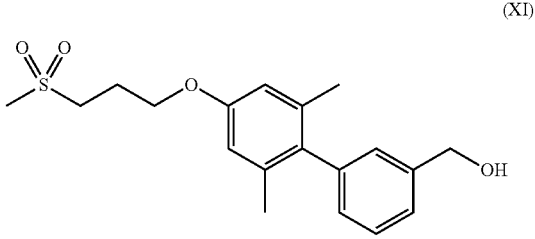 [SMILES: Cc1cc(OCCCS(C)(=O)=O)cc(C)c1-c1cccc(CO)c1]

or a salt thereof;

[17A] a method of producing a compound represented by the formula:

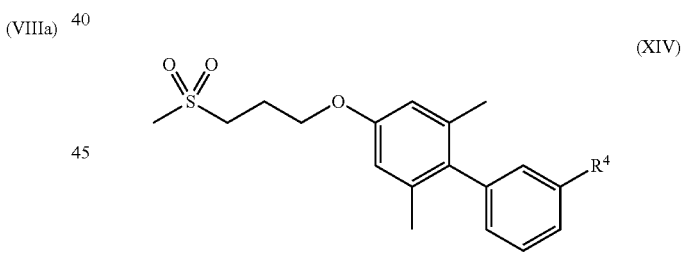

wherein R[4] is a formyl group or a hydroxymethyl group, or a salt thereof, comprising a step of reacting a compound represented by the formula:

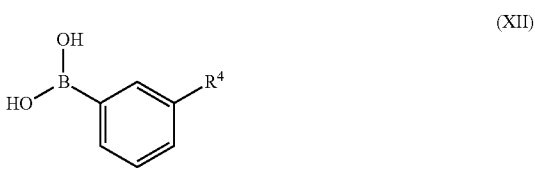

wherein R[4] is as defined above, or a salt thereof, with a compound represented by the formula:

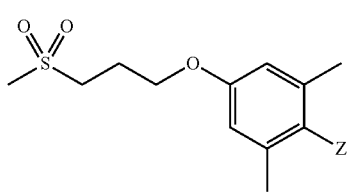
(XIII)

wherein Z is a halogen atom,
or a salt thereof in the presence of a palladium catalyst;

[18A] a compound represented by the formula:

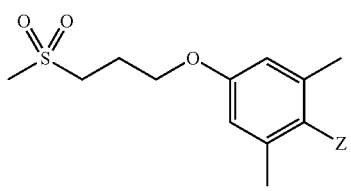
(XIII)

wherein Z is a halogen atom,
or a salt thereof;

[19A] the production method according to the aforementioned [14A], comprising (1) a step of producing an optically active form of a compound represented by the formula:

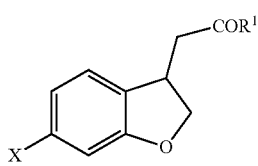
(II)

wherein each symbol is as defined above,
or a salt thereof, by subjecting a compound represented by the formula:

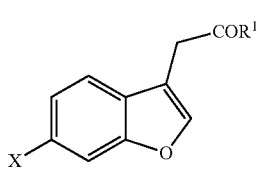
(I)

wherein each symbol is as defined above,
or a salt thereof, to an asymmetric hydrogenation reaction in the presence of a ruthenium complex;

(2) a step of producing a compound represented by the formula:

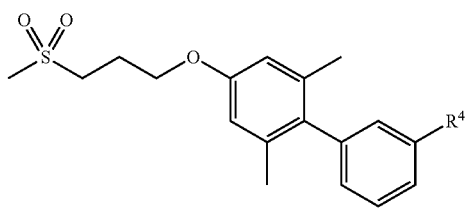
(XIV)

wherein each symbol is as defined above,
or a salt thereof, by reacting a compound represented by the formula:

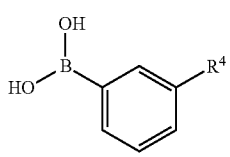
(XII)

wherein each symbol is as defined above,
or a salt thereof, with a compound represented by the formula:

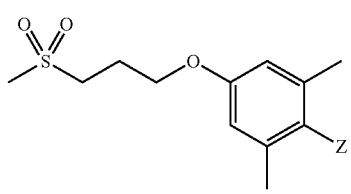
(XIII)

wherein each symbol is as defined above,
or a salt thereof, in the presence of a palladium catalyst; and (3) a step of producing a compound represented by the formula:

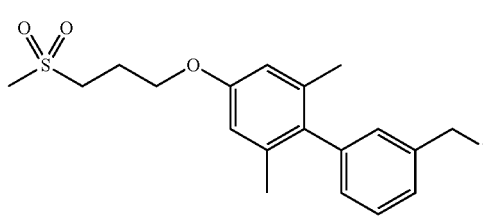
(IX)

wherein each symbol is as defined above,
or a salt thereof, by halogenating a compound represented by the formula:

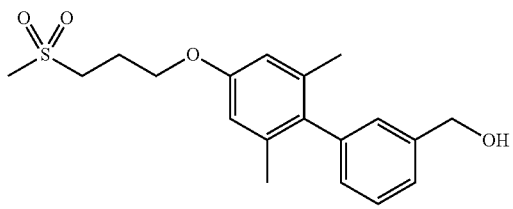

or a salt thereof;
[20A] a method of producing an optically active form of a compound represented by the formula:

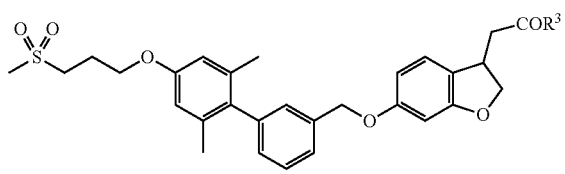

wherein $R^3$ is a hydroxy group or an optionally substituted $C_{1-6}$ alkoxy group,
or a salt thereof, comprising a step of subjecting a compound represented by the formula:

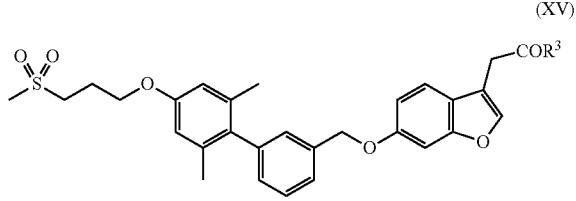

wherein each symbol is as defined above,
or a salt thereof, to an asymmetric hydrogenation reaction in the presence of a transition metal complex;
[21A] a crystal of [(3S)-6-({2',6'-dimethyl-4'-[3-(methylsulfonyl)propoxy]biphenyl-3-yl}methoxy)-2,3-dihydro-1-benzofuran-3-yl]acetic acid, which shows a powder X-ray diffraction pattern having characteristic peaks at lattice spacing (d) of about 19.24±0.2, 18.79±0.2, 6.35±0.2, 5.37±0.2, 4.91±0.2 and 4.83±0.2 angstroms by powder X-ray diffraction;
[22A] a method of producing an optically active form of a compound represented by the formula:

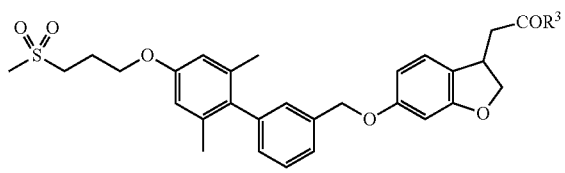

wherein each symbol is as defined above,
or a salt thereof, comprising the step of the aforementioned [1A];
[23A] a method of producing an optically active form of a compound represented by the formula:

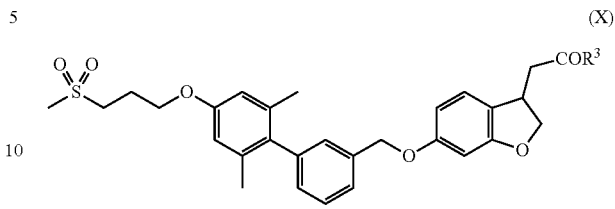

wherein each symbol is as defined above,
or a salt thereof, comprising the step of the aforementioned [16A];
[24A] a method of producing an optically active form of a compound represented by the formula:

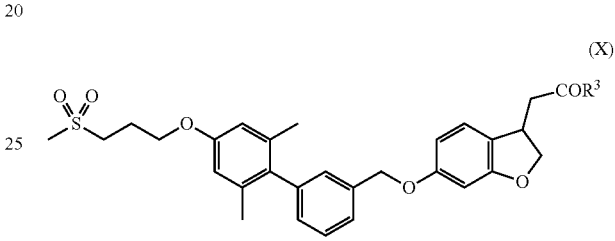

wherein each symbol is as defined above,
or a salt thereof, comprising the step of the aforementioned [17A];
[25A] the production method according to the aforementioned [14A], comprising the step of the aforementioned [1A];
[26A] the production method according to the aforementioned [14A], comprising the step of the aforementioned [16A];
[27A] the production method according to the aforementioned [14A], comprising the step of the aforementioned [17A];
[28A] the production method according to the aforementioned [14A], comprising the steps of the aforementioned [1A] and [16A];
[29A] the production method according to the aforementioned [14A], comprising the steps of the aforementioned [1A] and [17A];
[30A] the production method according to the aforementioned [14A], comprising the steps of the aforementioned [16A] and [17A]; and the like.

Moreover, the present invention relates to
[1B] a method of producing an optically active form of a compound represented by the formula:

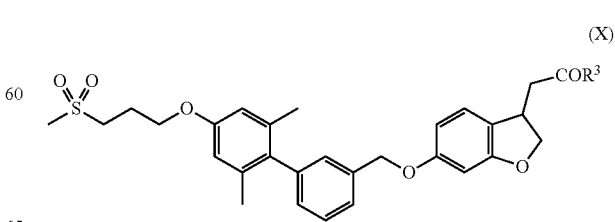

wherein $R^3$ is a hydroxy group or a $C_{1-6}$ alkoxy group, or a salt thereof, comprising a step of producing an optically active form of a compound represented by the formula:

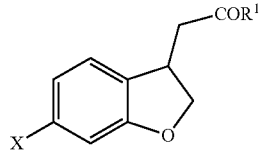

(II)

wherein $R^1$ is a hydroxy group or a $C_{1-6}$ alkoxy group; and X is a halogen atom, a hydroxy group or a $C_{1-6}$ alkoxy group, or a salt thereof, by subjecting a compound represented by the formula:

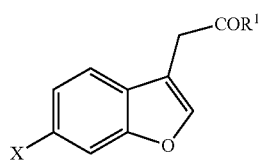

(I)

wherein $R^1$ is a hydroxy group or a $C_{1-6}$ alkoxy group; and X is a halogen atom, a hydroxy group or a $C_{1-6}$ alkoxy group, or a salt thereof, to an asymmetric hydrogenation reaction in the presence of a ruthenium complex;

[2B] the production method according to the aforementioned [1B], wherein the ruthenium complex comprises a compound represented by the formula:

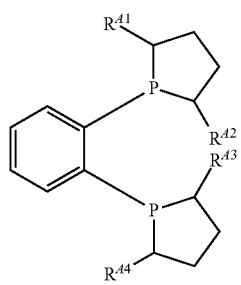

(III)

wherein $R^{A1}$, $R^{A2}$, $R^{A3}$ and $R^{A4}$ are each independently a $C_{1-6}$ alkyl group,
as a ligand;

[3B] the production method according to the aforementioned [1B] or [2B], wherein $R^1$ is a hydroxy group;

[4B] the production method according to any one of the aforementioned [1B] to [3B], further comprising a step of adding
(1) an optically active form of a compound represented by the formula:

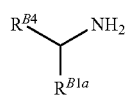

(IVa1)

wherein $R^{B1a}$ is a $C_{6-14}$ aryl group or a $C_{7-13}$ aralkyl group; and $R^{B4}$ is a $C_{1-6}$ alkyl group,
Or a salt thereof, or
(2) an optically active form of a compound represented by the formula:

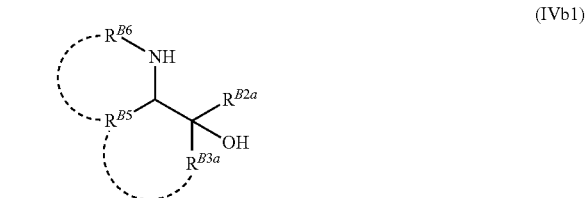

(IVb1)

wherein $R^{B2a}$ is a hydrogen atom or a $C_{6-14}$ aryl group;
$R^{B3a}$ is a $C_{6-14}$ aryl group or a $C_{1-6}$ alkyl group;
$R^{B5}$ is a $C_{1-6}$ alkyl group or a $C_{6-14}$ aryl group; and
$R^{B6}$ is a hydrogen atom or a $C_{1-6}$ alkyl group,
or a salt thereof;

[5B] the production method according to any one of the aforementioned [1B] to [4B], wherein an organic base of a compound represented by the formula:

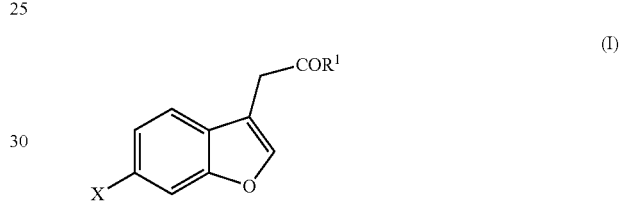

(I)

wherein $R^1$ is a hydroxy group or a $C_{1-6}$ alkoxy group; and X is a halogen atom, a hydroxy group or a $C_{1-6}$ alkoxy group, a salt thereof is
(1) an optically active form of a compound represented by the formula:

(IVa1)

wherein $R^{B1a}$ is a $C_{6-14}$ aryl group or a $C_{7-13}$ aralkyl group; and
$R^{B4}$ is a $C_{1-6}$ alkyl group, or
(2) an optically active form of a compound represented by the formula:

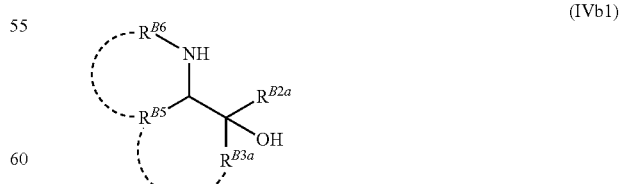

(IVb1)

wherein $R^{B2a}$ is a hydrogen atom or a $C_{6-14}$ aryl group;
$R^{B3a}$ is a $C_{6-14}$ aryl group or a $C_{1-6}$ alkyl group;
$R^{B5}$ is a $C_{1-6}$ alkyl group or a $C_{6-14}$ aryl group; and
$R^{B6}$ is a hydrogen atom or a $C_{1-6}$ alkyl group;

[6B] the production method according to any one of the aforementioned [2B] to [5B], wherein $R^{A1}$, $R^{A2}$, $R^{A3}$ and $R^{A4}$ are each an isopropyl group;

[7B] the production method according to any one of the aforementioned [1B] to [6B], wherein the ruthenium complex is represented by the formula:

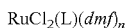

RuCl$_2$(L)(dmf)$_n$    (V)

wherein L is an optically active form of 1,2-bis(2,5-diisopropylphosphorano)benzene;
dmf is N,N-dimethylformamide; and,
n is an integer of one or more;

[8B] the production method according to the aforementioned [4B] or [5B], wherein $R^{B1a}$, $R^{B2a}$ and $R^{B3a}$ are each a phenyl group, $R^{B4}$ and $R^{B5}$ are each independently a $C_{1-6}$ alkyl group, and
$R^{B6}$ is a hydrogen atom;

[9B] a salt of an optically active form of a compound represented by the formula:

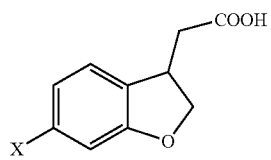

wherein X is a halogen atom, a hydroxy group or a $C_{1-6}$ alkoxy group,
wherein an organic base of the salt is
(1) an optically active form of a compound represented by the formula:

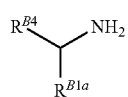

wherein $R^{B1a}$ is a $C_{6-14}$ aryl group or a $C_{7-13}$ aralkyl group; and
$R^{B4}$ is a $C_{1-6}$ alkyl group, or
(2) an optically active form of a compound represented by the formula:

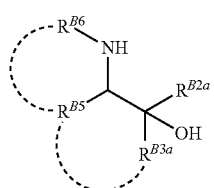

wherein $R^{B2a}$ is a hydrogen atom or a $C_{6-14}$ aryl group;
$R^{B3a}$ is a $C_{6-14}$ aryl group or a $C_{1-6}$ alkyl group;
$R^{B5}$ is a $C_{1-6}$ alkyl group or a $C_{6-14}$ aryl group; and
$R^{B6}$ is a hydrogen atom or a $C_{1-6}$ alkyl group;

[10B] the salt according to the aforementioned [9B], which is represented by the formula:

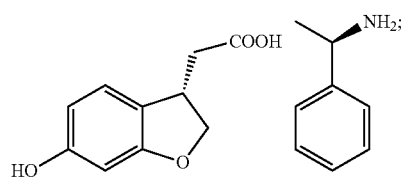

[11B] the salt according to the aforementioned [9B], which is represented by the formula:

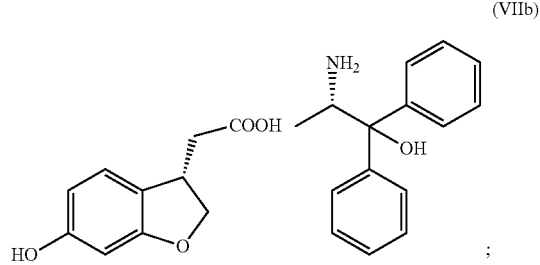 [SMILES: O=C(O)C[C@@H]1COc2cc(O)ccc21 ; C[C@H](N)C(O)(c1ccccc1)c1ccccc1]

[12B] a ruthenium complex represented by the formula:

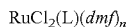

RuCl$_2$(L)(dmf)$_n$    (V)

wherein L is an optically active form of 1,2-bis(2,5-diisopropylphosphorano)benzene;
dmf is N,N-dimethylformamide; and,
n is an integer of one or more;

[13B] a method of producing an optically active form of a compound represented by the formula:

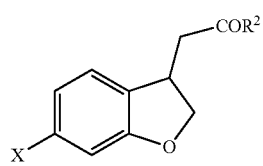

wherein $R^2$ is a $C_{1-6}$ alkoxy group; and
X is a halogen atom, a hydroxy group or a $C_{1-6}$ alkoxy group, or a salt thereof, comprising a step of esterifying the salt according to the aforementioned [9B];

[14B] a method of producing an optically active form of a compound represented by the formula:

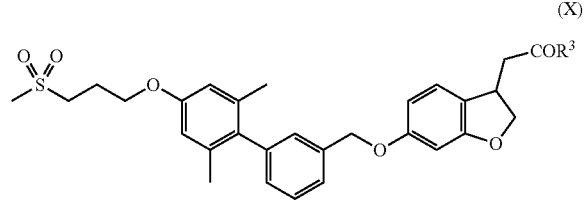

wherein $R^3$ is a hydroxy group or a $C_{1-6}$ alkoxy group, or a salt thereof, comprising a step of reacting a compound represented by the formula:

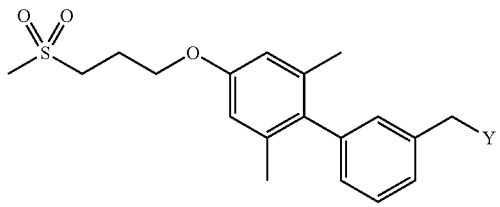

(IX)

wherein Y is a leaving group,
or a salt thereof with an optically active form of a compound represented by the formula:

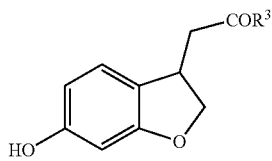

(VIIIa)

wherein $R^3$ is a hydroxy group or a $C_{1-6}$ alkoxy group,
or a salt thereof;

[15B] a compound represented by the formula:

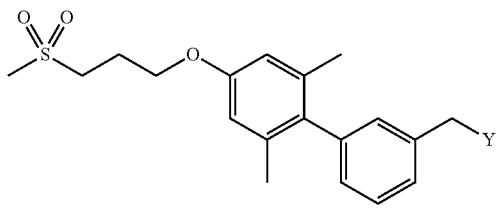

(IX)

wherein Y is a leaving group,
or a salt thereof;

[16B] a method of producing an optically active form of a compound represented by the formula:

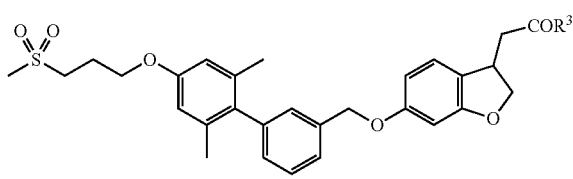

(X)

wherein $R^3$ is a hydroxy group or a $C_{1-6}$ alkoxy group,
or a salt thereof, comprising a step of producing a compound represented by the formula:

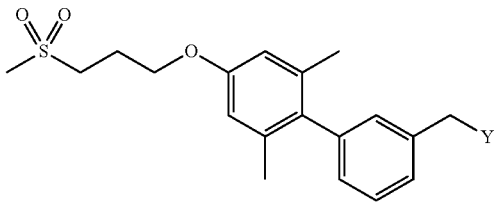

(IX)

wherein Y is a leaving group,
or a salt thereof, by converting a compound represented by the formula:

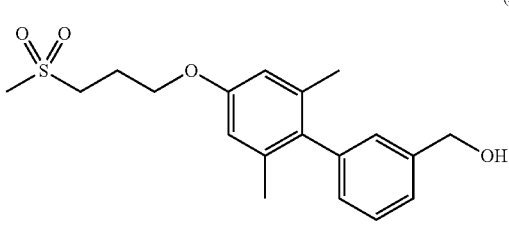

(XI)

or a salt thereof;

[17B] a method of producing an optically active form of a compound represented by the formula:

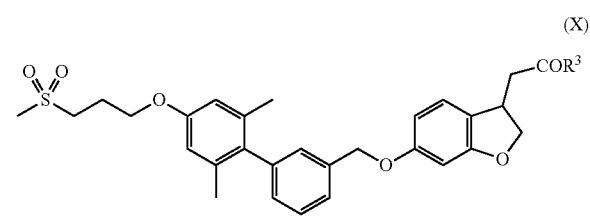

(X)

wherein $R^3$ is a hydroxy group or a $C_{1-6}$ alkoxy group,
or a salt thereof, comprising a step of producing a compound represented by the formula:

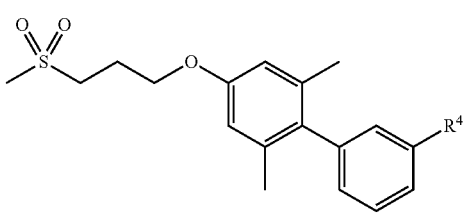

(XIV)

wherein $R^4$ is a formyl group or a hydroxymethyl group,
or a salt thereof, by reacting a compound represented by the formula:

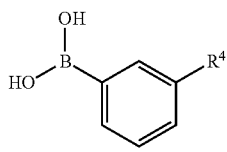
(XII)

wherein R⁴ is a formyl group or a hydroxymethyl group, or a salt thereof with a compound represented by the formula:

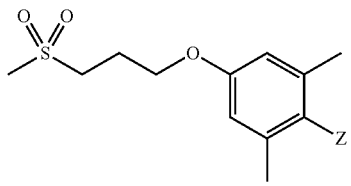
(XIII)

wherein Z is a halogen atom,
or a salt thereof, in the presence of a palladium catalyst;
[18B] a compound represented by the formula:

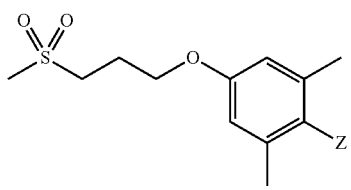
(XIII)

wherein Z is a halogen atom,
or a salt thereof;
[19B] the production method according to the aforementioned [14B], comprising
(1) a step of producing an optically active form of a compound represented by the formula:

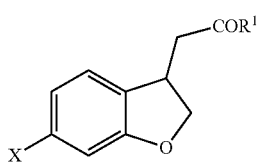
(II)

wherein $R^1$ is a hydroxy group or a $C_{1-6}$ alkoxy group; and
X is a halogen atom, a hydroxy group or a $C_{1-6}$ alkoxy group, or a salt thereof, by subjecting a compound represented by the formula:

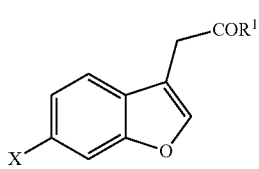
(I)

wherein $R^1$ is a hydroxy group or a $C_{1-6}$ alkoxy group; and
X is a halogen atom, a hydroxy group or a $C_{1-6}$ alkoxy group, or a salt thereof, to an asymmetric hydrogenation reaction in the presence of a ruthenium complex;
(2) a step of producing a compound represented by the formula:

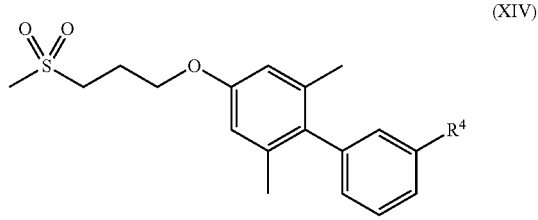
(XIV)

wherein R⁴ is a formyl group or a hydroxymethyl group, or a salt thereof, by reacting a compound represented by the formula:

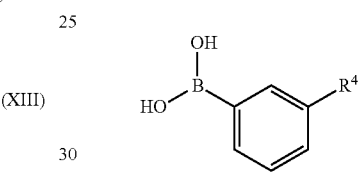
(XII)

wherein R⁴ is a formyl group or a hydroxymethyl group, or a salt thereof with a compound represented by the formula:

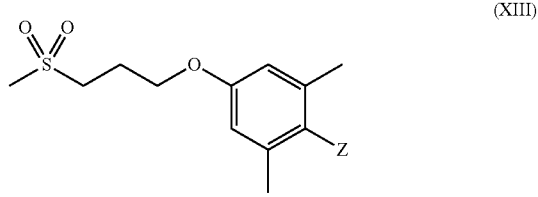
(XIII)

wherein Z is a halogen atom,
or a salt thereof, in the presence of a palladium catalyst; and
(3) a step of producing a compound represented by the formula:

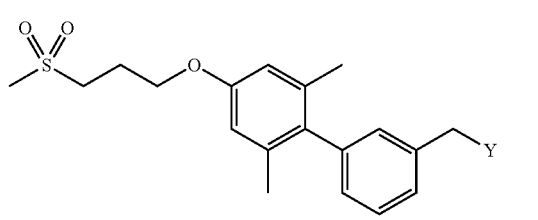
(IX)

wherein Y is a leaving group,
or a salt thereof, by converting a compound represented by the formula:

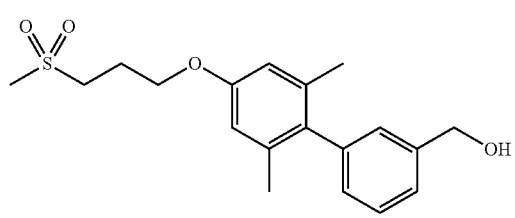
(XI)

or a salt thereof;
[20B] a method of producing an optically active form of a compound represented by the formula:

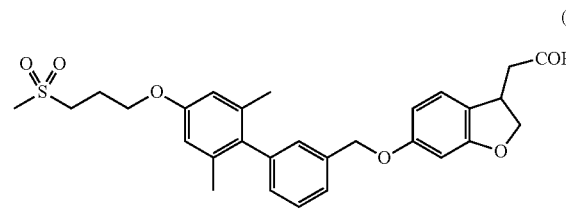
(X)

wherein $R^3$ is a hydroxy group or a $C_{1-6}$ alkoxy group, or a salt thereof, comprising a step of subjecting a compound represented by the formula:

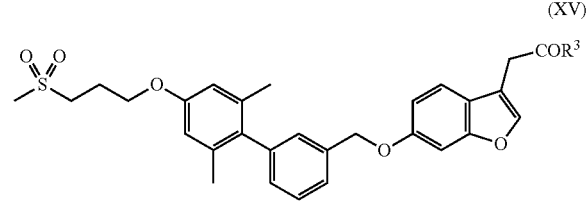
(XV)

wherein $R^3$ is a hydroxy group or a $C_{1-6}$ alkoxy group, or a salt thereof, to an asymmetric hydrogenation reaction in the presence of a transition metal complex;
[21B] a crystal of [(3S)-6-({2',6'-dimethyl-4'-[3-(methylsulfonyl)propoxy]biphenyl-3-yl}methoxy)-2,3-dihydro-1-benzofuran-3-yl]acetic acid, which shows a powder X-ray diffraction pattern having characteristic peaks at lattice spacing (d) of about 19.24±0.2, 18.79±0.2, 6.35±0.2, 5.37±0.2, 4.91±0.2, 4.83±0.2, 4.49±0.2, 3.84±0.2 and 3.74±0.2 angstroms by powder X-ray diffraction;
[22B] a method of producing an optically active form of a compound represented by the formula:

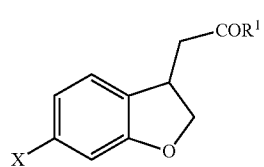
(II)

wherein $R^1$ is a hydroxy group or a $C_{1-6}$ alkoxy group; and X is a halogen atom, a hydroxy group or a $C_{1-6}$ alkoxy group, or a salt thereof, comprising a step of subjecting a compound represented by the formula:

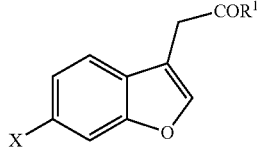
(I)

wherein $R^1$ is a hydroxy group or a $C_{1-6}$ alkoxy group; and X is a halogen atom, a hydroxy group or a $C_{1-6}$ alkoxy group, or a salt thereof, to an asymmetric hydrogenation reaction in the presence of a ruthenium complex;
[23B] a method of producing an optically active form of a compound represented by the formula:

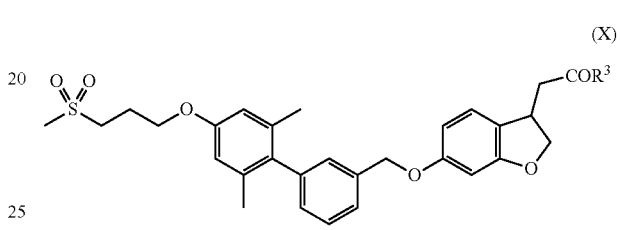
(X)

wherein $R^3$ is a hydroxy group or a $C_{1-6}$ alkoxy group, or a salt thereof, comprising a step of reacting a compound represented by the formula:

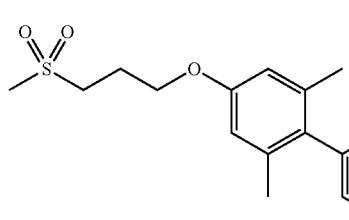
(XI)

or a salt thereof with an optically active form of a compound represented by the formula:

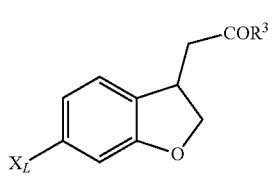
(VIIIb)

wherein $R^3$ is a hydroxy group or a $C_{1-6}$ alkoxy group; and $X_L$ is a leaving group,
or a salt thereof;
[24B] the production method according to any one of the aforementioned [1B] to [9B] and [13B], comprising the step of the aforementioned [14B];
[25B] the production method according to any one of the aforementioned [1B] to [9B] and [13B], comprising the step of the aforementioned [16B];
[26B] the production method according to any one of the aforementioned [1B] to [9B] and [13B], comprising the step of the aforementioned [17B];

[27B] the production method according to any one of the aforementioned [1B] to [9B] and [13B], comprising the steps of the aforementioned [14B] and [16B];

[28B] the production method according to any one of the aforementioned [1B] to [9B] and [13B], comprising the steps of the aforementioned [14B] and [17B];

[29B] the production method according to any one of the aforementioned [1B] to [9B] and [13B], comprising the steps of the aforementioned [16B] and [17B];

[30B] the production method according to the aforementioned [14B], comprising the step of the aforementioned [16B];

[31B] the production method according to the aforementioned [14B], comprising the step of the aforementioned [17B];

[32B] the production method according to the aforementioned [14B], comprising the steps of the aforementioned [16B] and [17B];

[33B] the production method according to the aforementioned [16B], comprising the step of the aforementioned [17B];

[34B] the production method according to any one of the aforementioned [24B] to [29B], wherein the ruthenium complex comprises an optically active form of a compound represented by the formula:

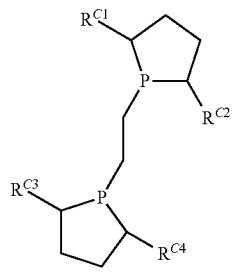

(IIIa)

wherein $R^{C1}$, $R^{C2}$, $R^{C3}$ and $R^{C4}$ are each independently a $C_{1-6}$ alkyl group or a $C_{6-14}$ aryl group, as a ligand;

[35B] the production method according to the aforementioned [34B], wherein $R^{C1}$, $R^{C2}$, $R^{C3}$ and $R^{C4}$ are each independently a methyl group;

[36B] a ruthenium complex represented by the formula:

$$RuCl_2(La)(dmf)_n \quad \quad (Va)$$

wherein La is an optically active form of 1,2-bis(2,5-diethylphosphorano)benzene, or an optically active form of 1,2-bis(2,5-dimethylphosphorano)ethane;

dmf is N,N-dimethylformamide; and, n is an integer of one or more;

and the like.

Furthermore, the present invention relates to

[1C] a method of producing an optically active form of a compound represented by the formula:

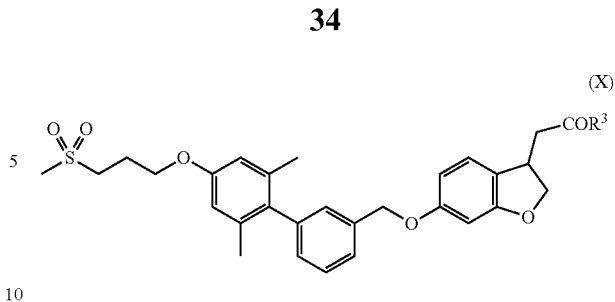

(X)

wherein $R^3$ is a hydroxy group, or a salt thereof, comprising a step of producing an optically active form of a compound represented by the formula:

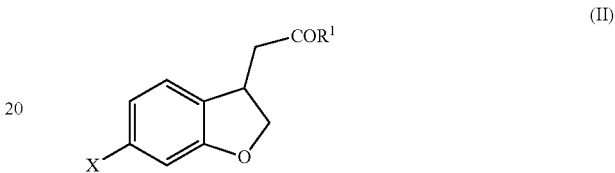

(II)

wherein $R^1$ is a hydroxy group; and

X is a hydroxy group, or a salt thereof, by subjecting a compound represented by the formula:

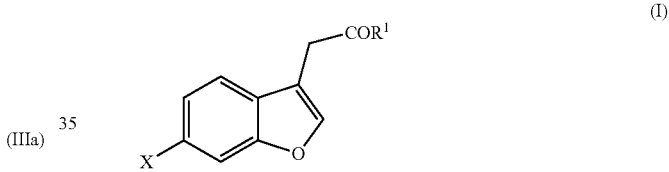

(I)

wherein $R^1$ is a hydroxy group; and

X is a hydroxy group, or a salt thereof to an asymmetric hydrogenation reaction in the presence of a ruthenium complex;

[2C] the production method according to the aforementioned [1C], wherein the ruthenium complex comprises a compound represented by the formula:

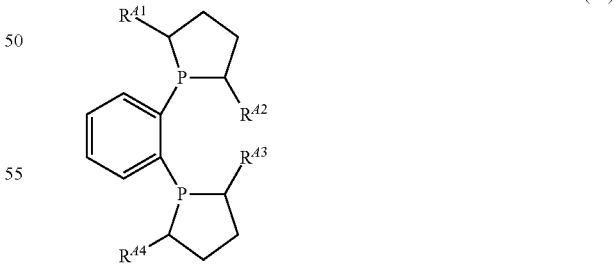

(III)

wherein $R^{A1}$, $R^{A2}$, $R^{A3}$ and $R^{A4}$ are each independently a $C_{1-6}$ alkyl group, as a ligand;

[3C] the production method according to the aforementioned [1C] or [2C], further comprising a step of adding (1) an optically active form of a compound represented by the formula:

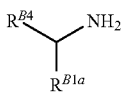

wherein $R^{B1a}$ is a $C_{6-14}$ aryl group; and $R^{B4}$ is a $C_{1-6}$ alkyl group, or a salt thereof, or (2) an optically active form of a compound represented by the formula:

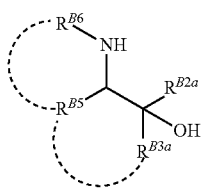

wherein $R^{B2a}$ is a hydrogen atom or a $C_{6-14}$ aryl group;

$R^{B3a}$ is a $C_{6-14}$ aryl group;

$R^{B5}$ is a $C_{1-6}$ alkyl group; and $R^{B6}$ is a hydrogen atom, or a salt thereof;

[4C] the production method according to any one of the aforementioned [1C] to [3C], wherein an organic base of a salt of a compound represented by the formula:

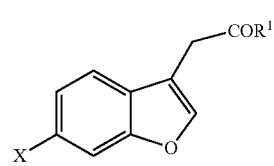

wherein $R^1$ is a hydroxy group; and

X is a hydroxy group, is (1) an optically active form of a compound represented by the formula:

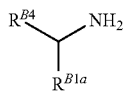

wherein $R^{B1a}$ is a $C_{6-14}$ aryl group; and $R^{B4}$ is a $C_{1-6}$ alkyl group, or (2) an optically active form of a compound represented by the formula:

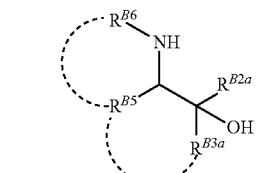

wherein $R^{B2a}$ is a hydrogen atom or a $C_{6-14}$ aryl group;

$R^{B3a}$ is a $C_{6-14}$ aryl group;

$R^{B5}$ is a $C_{1-6}$ alkyl group; and $R^{B6}$ is a hydrogen atom;

[5C] the production method according to any one of the aforementioned [2C] to [4C], wherein $R^{A1}$, $R^{A2}$, $R^{A3}$ and $R^{A4}$ are each an isopropyl group;

[6C] the production method according to any one of the aforementioned [1C] to [5C], wherein the ruthenium complex is a complex represented by the formula:

$$RuCl_2(L)(dmf)_n \quad (V)$$

wherein L is an optically active form of 1,2-bis(2,5-diisopropylphosphorano)benzene;

dmf is N,N-dimethylformamide; and, n is an integer of one or more;

[7C] the production method according to the aforementioned [3C] or [4C], wherein $R^{B1a}$, $R^{B2a}$ and $R^{B3a}$ are each a phenyl group;

[8C] a salt of an optically active form of a compound represented by the formula:

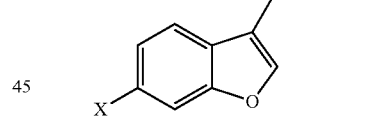

wherein X is a hydroxy group, wherein an organic base of the salt is (1) an optically active form of a compound represented by the formula:

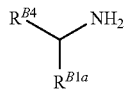

wherein $R^{B1a}$ is a $C_{6-14}$ aryl group; and $R^{B4}$ is a $C_{1-6}$ alkyl group, or (2) an optically active form of a compound represented by the formula:

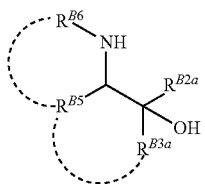

(IVb1)

wherein $R^{B2a}$ is a hydrogen atom or a $C_{6-14}$ aryl group;
$R^{B3a}$ is a $C_{6-14}$ aryl group;
$R^{B5}$ is a $C_{1-6}$ alkyl group; and
$R^{B6}$ is a hydrogen atom;
[9C] the salt according to the aforementioned [8C], which is represented by the formula:

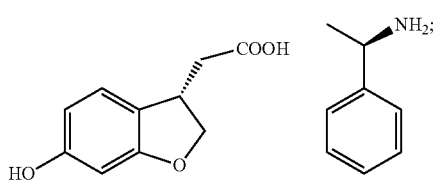

(VIIa)

[10C] the salt according to the aforementioned [8C], which is represented by the formula:

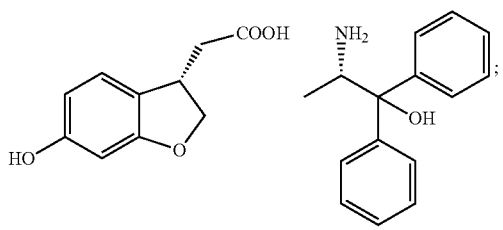

(VIIb)

[11C] a ruthenium complex represented by the formula:

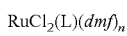

(V)

wherein L is an optically active form of 1,2-bis(2,5-diisopropylphosphorano)benzene;
dmf is N,N-dimethylformamide; and
n is an integer of one or more;
[12C] a method of producing an optically active form of a compound represented by the formula:

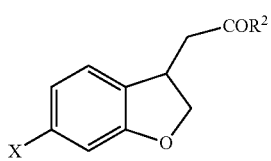

(VIII)

wherein $R^2$ is a $C_{1-6}$ alkoxy group; and
X is a hydroxy group,
or a salt thereof, comprising a step of esterifying the salt according to the aforementioned [8C];

[13C] a method of producing an optically active form of a compound represented by the formula:

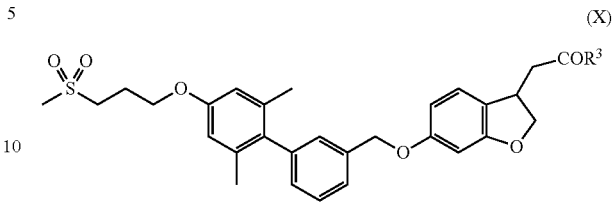

(X)

wherein $R^3$ is a hydroxy group,
or a salt thereof, comprising a step of reacting a compound represented by the formula:

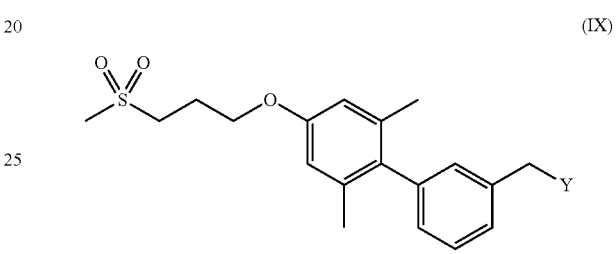

(IX)

wherein Y is a leaving group (preferably, a halogen atom or an optionally halogenated $C_{1-6}$ alkylsulfonyloxy group),
or a salt thereof with an optically active form of a compound represented by the formula:

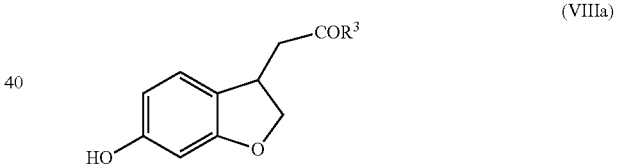

(VIIIa)

wherein $R^3$ is a hydroxy group,
or a salt thereof;
[14C] a compound represented by the formula:

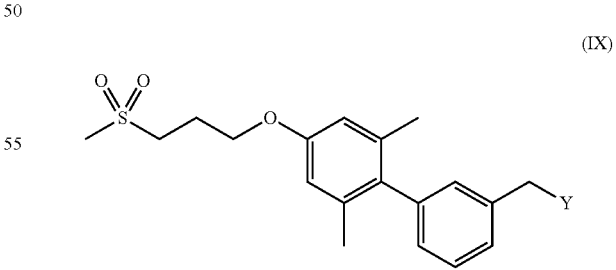

(IX)

wherein Y is a leaving group (preferably, a halogen atom, or an optionally halogenated $C_{1-6}$ alkylsulfonyloxy group),
or a salt thereof;

[15C] a method of producing an optically active form of a compound represented by the formula:

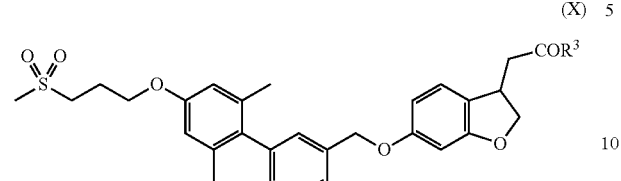
(X)

wherein $R^3$ is a hydroxy group,
or a salt thereof, comprising a step of producing a compound represented by the formula:

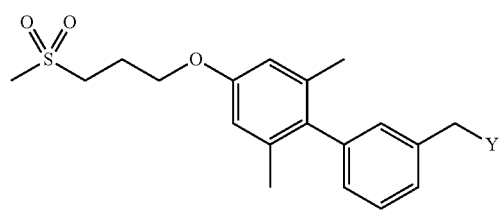
(IX)

wherein Y is a leaving group (preferably, a halogen atom, or an optionally halogenated $C_{1-6}$ alkylsulfonyloxy group),
or a salt thereof, by converting a compound represented by the formula:

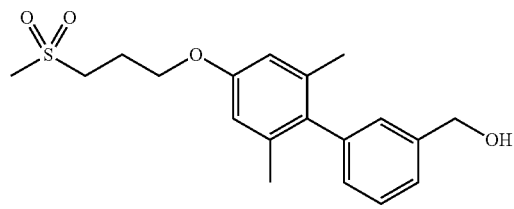
(XI)

or a salt thereof;

[16C] a method of producing an optically active form of a compound represented by the formula:

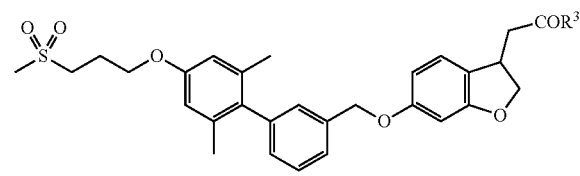
(X)

wherein $R^3$ is a hydroxy group,
or a salt thereof, including a step of producing a compound represented by the formula:

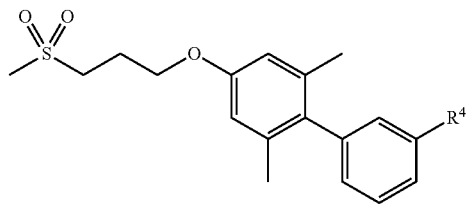
(XIV)

wherein $R^4$ is a formyl group,
or a salt thereof, by reacting a compound represented by the formula:

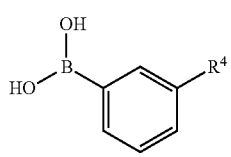
(XII)

wherein $R^4$ is a formyl group,
or a salt thereof, with a compound represented by the formula:

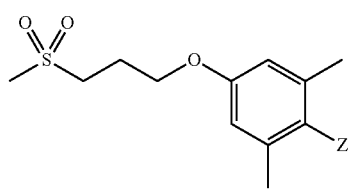
(XIII)

wherein Z is a halogen atom,
or a salt thereof, in the presence of a palladium catalyst;

[17C] a compound represented by the formula:

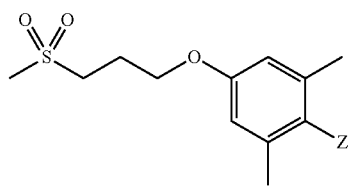
(XIII)

wherein Z is a halogen atom,
or a salt thereof;

[18C] the production method according to the aforementioned [13C], comprising
(1) a step of producing an optically active form of a compound represented by the formula:

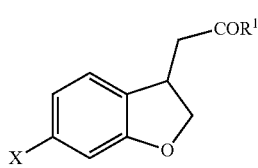
(II)

wherein $R^1$ is a hydroxy group; and

X is a hydroxy group, or a salt thereof, by subjecting a compound represented by the formula:

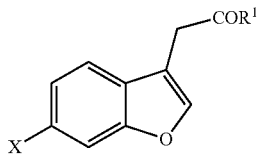

(I)

wherein $R^1$ is a hydroxy group; and

X is a hydroxy group, or a salt thereof, to an asymmetric hydrogenation reaction in the presence of a ruthenium complex;

(2) a step of producing a compound represented by the formula:

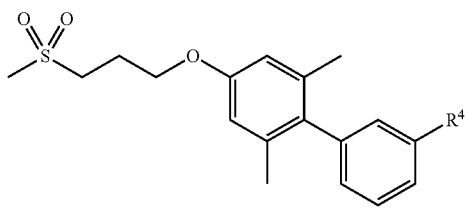

(XIV)

wherein $R^4$ is a formyl group, or a salt thereof, by reacting a compound represented by the formula:

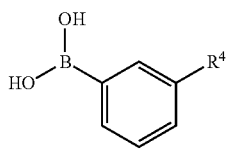

(XII)

wherein $R^4$ is a formyl group, or a salt thereof, with a compound represented by the formula:

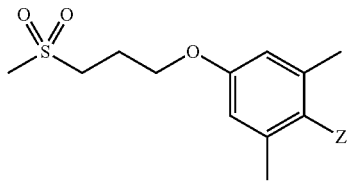

(XIII)

wherein Z is a halogen atom, or a salt thereof, in the presence of a palladium catalyst; and (3) a step of producing a compound represented by the formula:

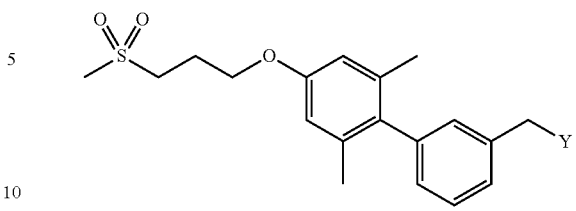

(IX)

wherein Y is a leaving group (preferably, a halogen atom, or an optionally halogenated $C_{1-6}$ alkylsulfonyloxy group), or a salt thereof, by converting a compound represented by the formula:

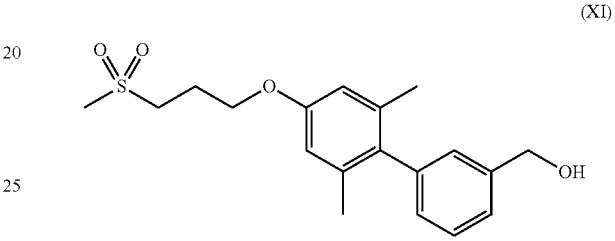

(XI)

or a salt thereof;

[19C] a method of producing an optically active form of a compound represented by the formula:

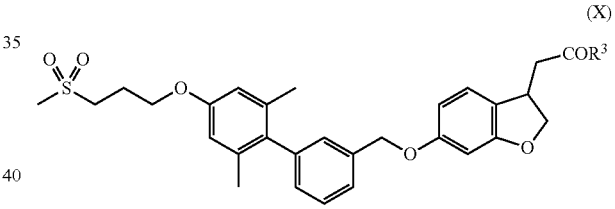

(X)

wherein $R^3$ is a hydroxy group, or a salt thereof, comprising a step of subjecting a compound represented by the formula:

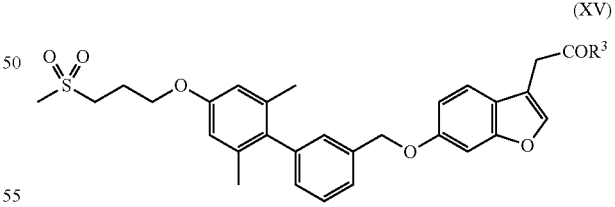

(XV)

wherein $R^3$ is a hydroxy group, or a salt thereof, to an asymmetric hydrogenation reaction in the presence of a transition metal complex;

[20C] a crystal of [(3S)-6-({2',6'-dimethyl-4'-[3-(methylsulfonyl)propoxy]biphenyl-3-yl}methoxy)-2,3-dihydro-1-benzofuran-3-yl]acetic acid, which shows a powder X-ray diffraction pattern having characteristic peaks at lattice spacing (d) of about 19.24±0.2, 18.79±0.2, 6.35±0.2, 5.37±0.2, 4.91±0.2, 4.83±0.2, 4.56±0.2, 4.49±0.2, 4.12±0.2, 3.84±0.2, 3.80±0.2 and 3.74±0.2 angstroms by powder X-ray diffraction;

[21C] a method of producing an optically active form of a compound represented by the formula:

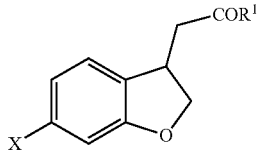

(II)

wherein R¹ is a hydroxy group; and
X is a hydroxy group,
or a salt thereof, comprising a step of subjecting a compound represented by the formula:

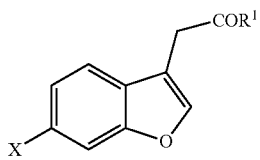

(I)

wherein R¹ is a hydroxy group; and
X is a hydroxy group,
or a salt thereof, to an asymmetric hydrogenation reaction in the presence of a ruthenium complex;

[22C] a method of producing an optically active form of a compound represented by the formula:

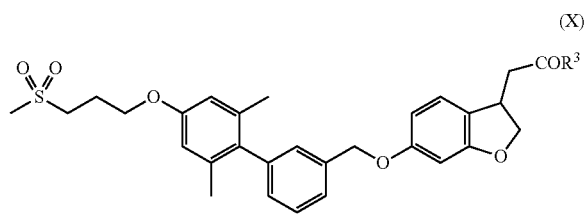

(X)

wherein R³ is a hydroxy group or a $C_{1-6}$ alkoxy group, or a salt thereof, comprising a step of reacting a compound represented by the formula:

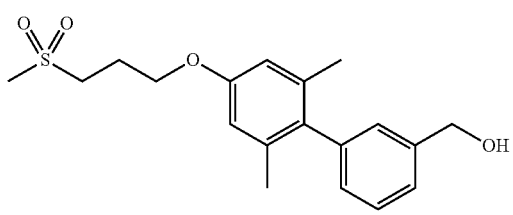

(XI)

or a salt thereof, with an optically active form of a compound represented by the formula:

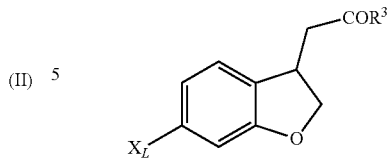

(VIIIb)

wherein R³ is a hydroxy group or a $C_{1-6}$ alkoxy group; and
$X_L$ is a leaving group (preferably, an optionally halogenated $C_{1-6}$ alkylsulfonyloxy group),
or a salt thereof;

[23C] the production method according to any one of the aforementioned [1C] to [8C] and [12C], comprising the step of the aforementioned [13C];

[24C] the production method according to any one of the aforementioned [1C] to [8C] and [12C], comprising the step of the aforementioned [15C];

[25C] the production method according to any one of the aforementioned [1C] to [8C] and [12C], comprising the step of the aforementioned [16C];

[26C] the production method according to any one of the aforementioned [1C] to [8C] and [12C], comprising the steps of the aforementioned [13C] and [15C];

[27C] the production method according to any one of the aforementioned [1C] to [8C] and [12C], comprising the steps of the aforementioned [13C] and [16C];

[28C] the production method according to any one of the aforementioned [1C] to [8C] and [12C], comprising the steps of the aforementioned [15C] and [16C];

[29C] the production method according to the aforementioned [13C], comprising the step of the aforementioned [15C];

[30C] the production method according to the aforementioned [13C], comprising the step of the aforementioned [16C];

[31C] the production method according to the aforementioned [13C], comprising the steps of the aforementioned [15C] and [16C];

[32C] the production method according to the aforementioned [15C], comprising the step of the aforementioned [16C];

[33C] the production method according to any one of the aforementioned [23C] to [28C], wherein the ruthenium complex comprises an optically active form of a compound represented by the formula:

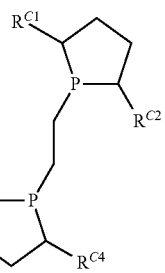

(IIIa)

wherein $R^{C1}$, $R^{C2}$, $R^{C3}$ and $R^{C4}$ are each independently a $C_{1-6}$ alkyl group or a $C_{6-14}$ aryl group,
as a ligand;

[34C] the production method according to the aforementioned [33C], wherein $R^{C1}$, $R^{C2}$, $R^{C3}$ and $R^{C4}$ are each independently a methyl group;

[35C] a ruthenium complex represented by the formula:

$$RuCl_2(La)(dmf)_n \qquad (Va)$$

wherein La is an optically active form of 1,2-bis(2,5-diethylphosphorano)benzene, or an optically active form of 1,2-bis(2,5-dimethylphosphorano)ethane;
dmf is N,N-dimethylformamide; and,
n is an integer of one or more; and the like.

Effect of the Invention

The production method of the present invention can produce an optically active dihydrobenzofuran derivative conveniently and with high stereoselectivity.

DETAILED DESCRIPTION OF THE INVENTION

Figure 1:
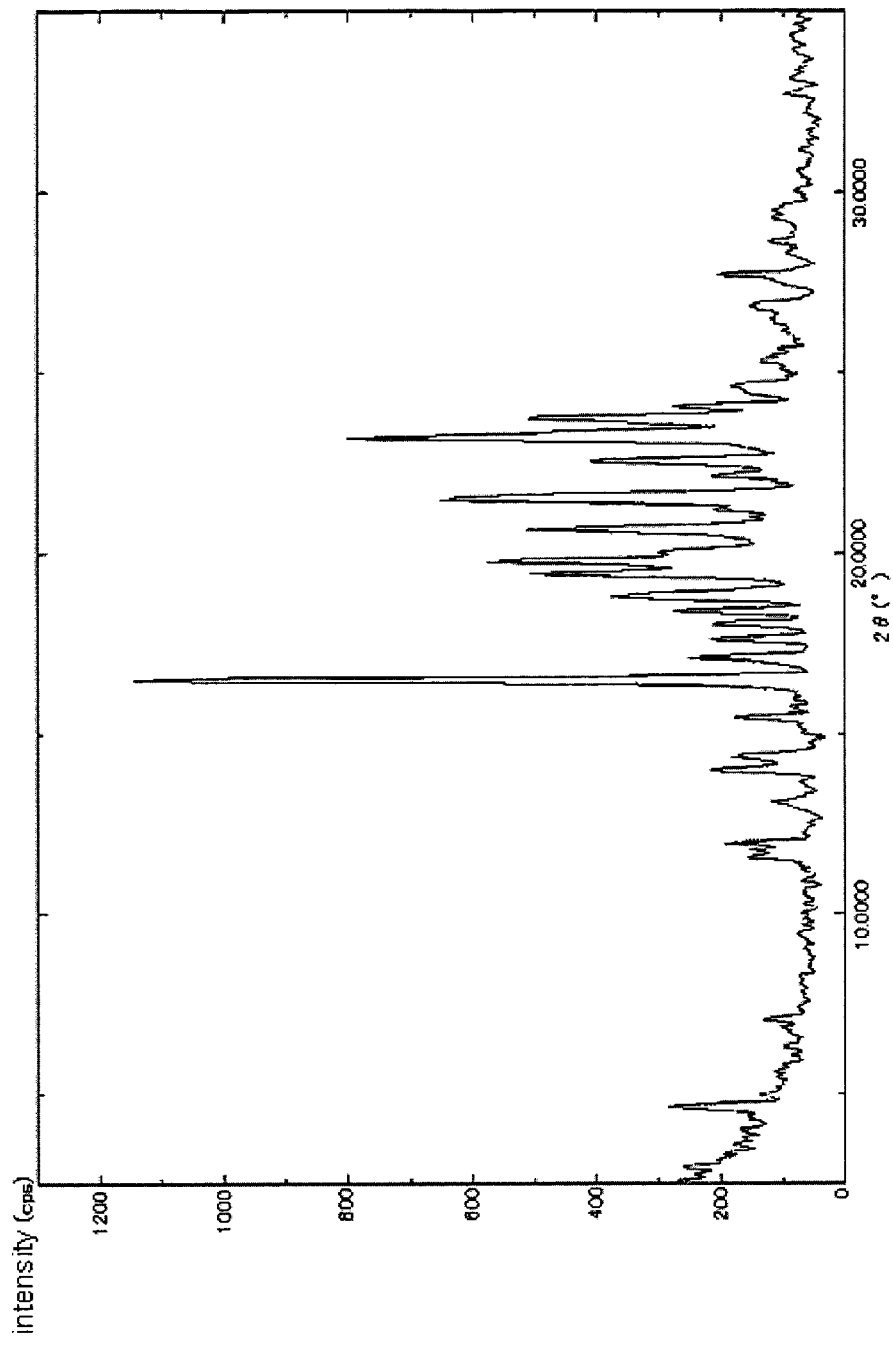
FIG. 1 shows a powder X-ray diffraction pattern of Example 21.
Figure 2:
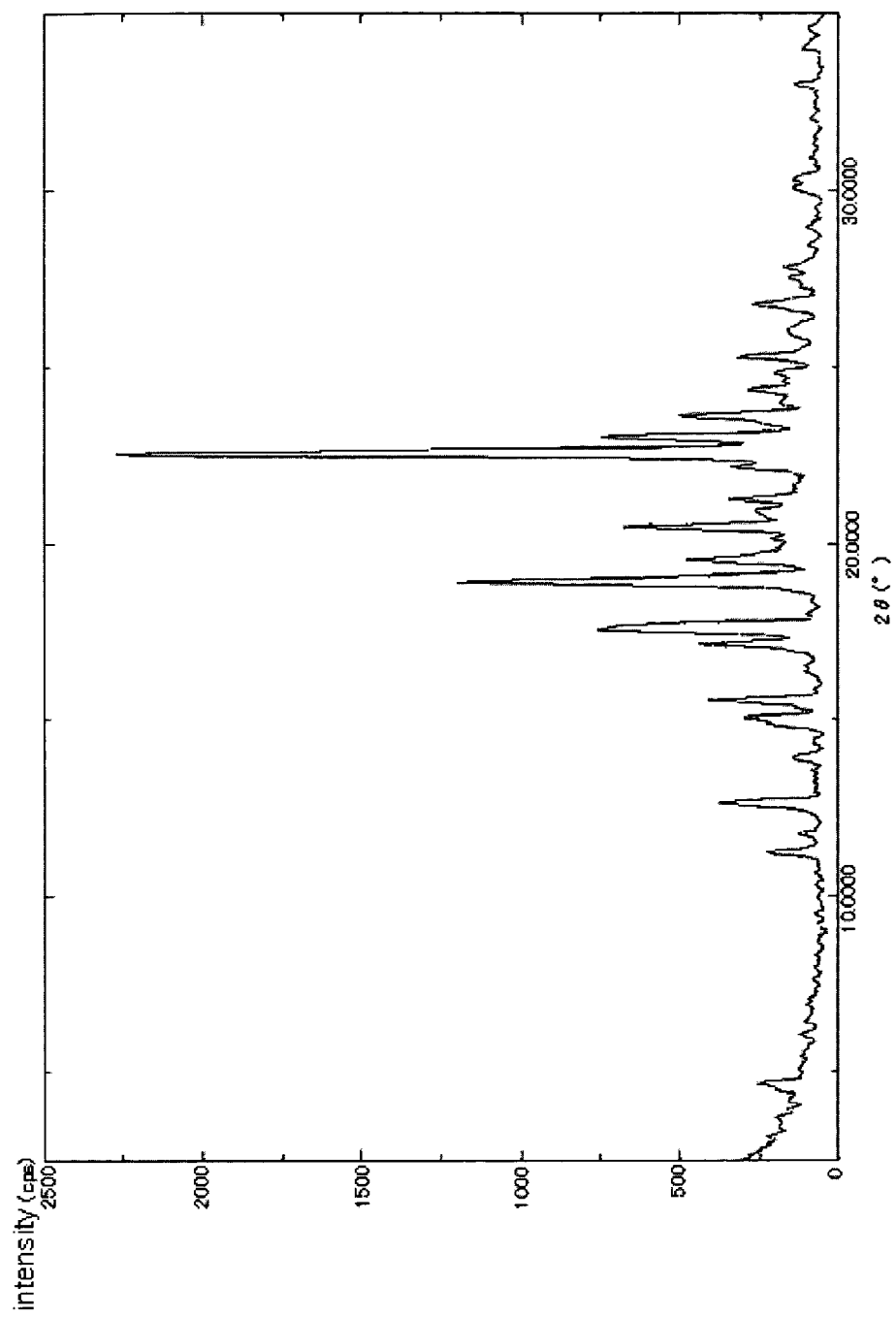
FIG. 2 shows a powder X-ray diffraction pattern of Reference Example 11.
Figure 3:
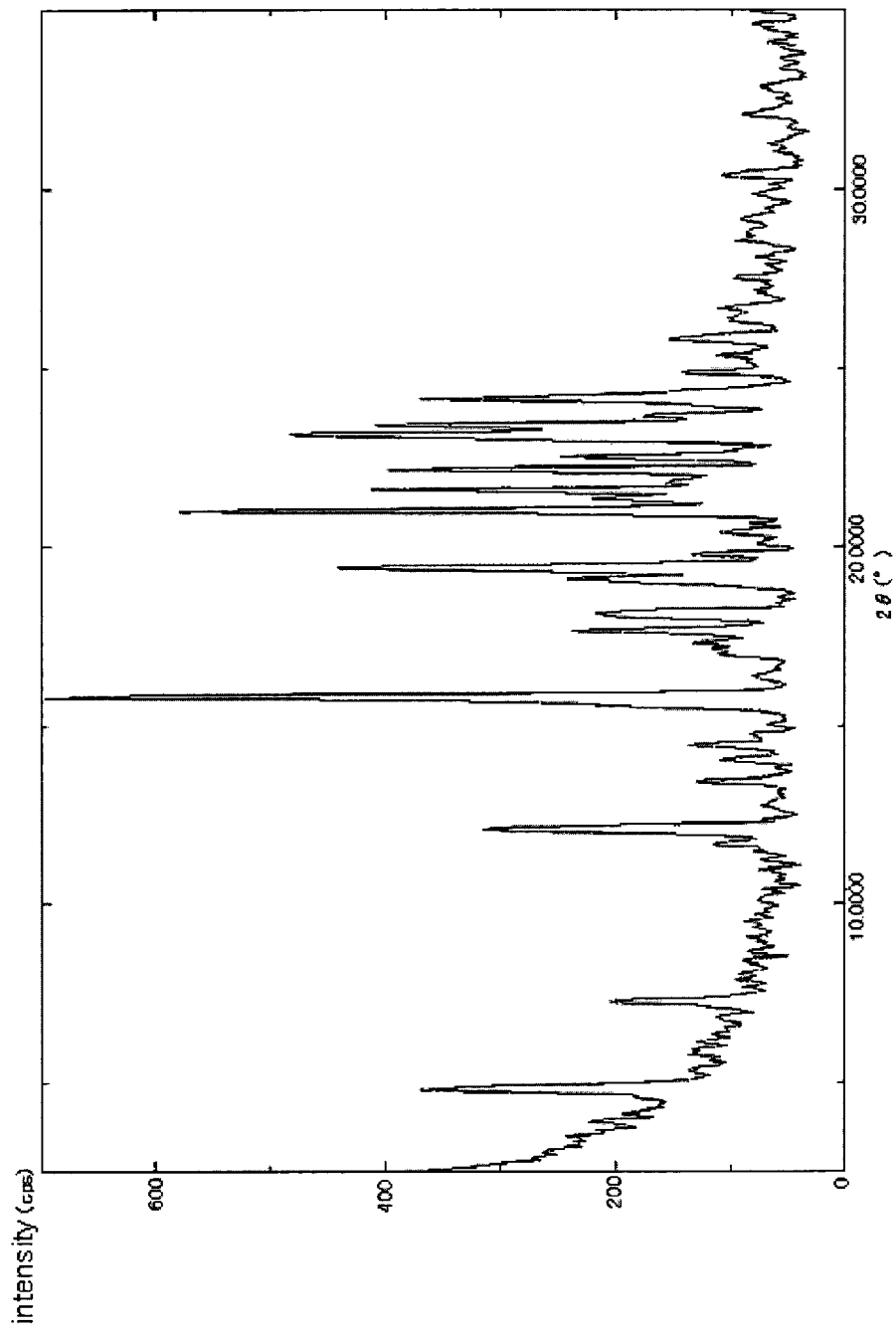
FIG. 3 shows a powder X-ray diffraction pattern of Reference Example 12.

The definition of each symbol in the formulas (I) to (XV) is explained in detail in the following.

In the present specification, the "halogen atom" means, unless otherwise specified, a fluorine atom, a chlorine atom, a bromine atom or an iodine atom.

In the present specification, the "$C_{1-3}$ alkylenedioxy group" means, unless otherwise specified, methylenedioxy, ethylenedioxy and the like.

In the present specification, the "$C_{1-6}$ alkyl group" means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

In the present specification, the "$C_{1-6}$ alkoxy group" means, unless otherwise specified, methoxy, ethoxy, propoxy, isopropoxy, butoxy, isobutoxy, sec-butoxy, tert-butoxy and the like.

In the present specification, the "$C_{6-14}$ aryl group" means, unless otherwise specified, phenyl, naphthyl, anthryl, phenanthryl, acenaphthyl, biphenylyl and the like.

$R^{41}$, $R^{42}$, $R^{43}$ and $R^{44}$ are each independently an optionally substituted hydrocarbon group.

Examples of the "hydrocarbon group" of the "optionally substituted hydrocarbon group" for $R^{41}$, $R^{42}$, $R^{43}$ or $R^{44}$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group and the like.

Examples of the $C_{1-10}$ alkyl group include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Of these, a $C_{1-6}$ alkyl group is preferable.

Examples of the $C_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Of these, $C_{2-6}$ alkenyl group is preferable.

Examples of the $C_{2-10}$ alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Of these, $C_{2-6}$ alkynyl group is preferable.

Examples of the $C_{3-10}$ cycloalkyl group include cyclopropyl, cyclobutyl, cyclopentyl, cyclohexyl, cycloheptyl, cyclooctyl and the like. Of these, $C_{3-6}$ cycloalkyl group is preferable.

Examples of the $C_{3-10}$ cycloalkenyl group include 2-cyclopenten-1-yl, 3-cyclopenten-1-yl, 2-cyclohexen-1-yl, 3-cyclohexen-1-yl and the like. Of these, $C_{3-6}$ cycloalkenyl group is preferable.

Examples of the $C_{4-10}$ cycloalkadienyl group include 2,4-cyclopentadien-1-yl, 2,4-cyclohexadien-1-yl, 2,5-cyclohexadien-1-yl and the like. Of these, $C_{4-6}$ cycloalkadienyl group is preferable.

Each of the above-mentioned $C_{3-10}$ cycloalkyl group, $C_{3-10}$ cycloalkenyl group and $C_{4-10}$ cycloalkadienyl group may be fused with a benzene ring to form a fused ring group. Examples of the fused ring group include indanyl, dihydronaphthyl, tetrahydronaphthyl, fluorenyl and the like.

The above-mentioned $C_{3-10}$ cycloalkyl group, $C_{3-10}$ cycloalkenyl group and $C_{4-10}$ cycloalkadienyl group each may be a $C_{7-10}$ bridged hydrocarbon group. Examples of the $C_{7-10}$ bridged hydrocarbon group include bicyclo[2.2.1]heptyl(norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Moreover, the above-mentioned $C_{3-10}$ cycloalkyl group, $C_{3-10}$ cycloalkenyl group and $C_{4-10}$ cycloalkadienyl group each may form a spiro ring group with $C_{3-10}$ cycloalkane, $C_{3-10}$ cycloalkene or $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the spiro ring group include spiro[4.5]decan-8-yl and the like.

Examples of the $C_{6-14}$ aryl group include phenyl, naphthyl, anthryl, phenanthryl, acenaphthyl, biphenylyl and the like. Of these, $C_{6-12}$ aryl group is preferable.

Examples of the $C_{7-13}$ aralkyl group include benzyl, phenethyl, naphthylmethyl, biphenylylmethyl and the like.

Examples of the $C_{8-13}$ arylalkenyl group include styryl and the like.

The $C_{1-10}$ alkyl group, $C_{2-10}$ alkenyl group and $C_{2-10}$ alkynyl group exemplified as the aforementioned "hydrocarbon group" optionally have 1 to 7 (preferably, 1 to 3) substituents at substitutable position(s).

Examples of Such Substituent Include (1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group, (c) a $C_{1-6}$ alkoxy group optionally substituted by 1 to 3 halogen atoms, and
(d) a halogen atom;
(4) a nonaromatic heterocyclic group (e.g., tetrahydrofuryl, morpholinyl, thiomorpholinyl, piperidinyl, pyrrolidinyl, piperazinyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms,
   (d) a halogen atom, and
   (e) an oxo group;
(5) an amino group optionally mono- or di-substituted by substituent(s) selected from
   (a) a $C_{1-6}$ alkyl group optionally substituted by 1 to 3 halogen atoms,
   (b) a $C_{1-6}$ alkyl-carbonyl group optionally substituted by 1 to 3 halogen atoms,
   (c) a $C_{1-6}$ alkoxy-carbonyl group optionally substituted by 1 to 3 halogen atoms,
   (d) a $C_{1-6}$ alkylsulfonyl group (e.g., methylsulfonyl) optionally substituted by 1 to 3 halogen atoms,
   (e) a carbamoyl group optionally mono- or di-substituted by a $C_{1-6}$ alkyl group optionally substituted by 1 to 3 halogen atoms, and
   (f) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
   (a) a halogen atom,
   (b) a $C_{1-6}$ alkoxy group,
   (c) a $C_{6-14}$ aryl group (e.g., phenyl), and
   (d) a heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by a $C_{1-6}$ alkyl group optionally substituted by 1 to 3 halogen atoms;
(10) a thiocarbamoyl group optionally mono- or di-substituted by a $C_{1-6}$ alkyl group optionally substituted by 1 to 3 halogen atoms;
(11) a sulfamoyl group optionally mono- or di-substituted by a $C_{1-6}$ alkyl group optionally substituted by 1 to 3 halogen atoms;
(12) a carboxy group;
(13) a hydroxy group;
(14) a $C_{1-6}$ alkoxy group optionally substituted by 1 to 3 substituents selected from
   (a) a halogen atom,
   (b) a carboxy group,
   (c) a $C_{1-6}$ alkoxy group,
   (d) a $C_{1-6}$ alkoxy-carbonyl group optionally substituted by 1 to 3 $C_{6-14}$ aryl groups (e.g., phenyl),
   (e) an amino group optionally mono- or di-substituted by substituent(s) selected from a $C_{1-6}$ alkyl group and a $C_{1-6}$ alkoxy-carbonyl group,
   (f) a heterocyclic group (e.g., tetrahydrofuryl), and
   (g) a $C_{3-10}$ cycloalkyl group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
   (a) a halogen atom, and
   (b) a $C_{1-6}$ alkyl group optionally substituted by 1 to 3 halogen atoms;
(20) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
   (a) a halogen atom, and
   (b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom;
(28) a $C_{1-3}$ alkylenedioxy group;
(29) a $C_{1-3}$ alkyleneoxy group (e.g., methyleneoxy, ethyleneoxy);
(30) aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-10}$ cycloalkoxy group (e.g., cyclopropoxy, cyclopentyloxy) optionally substituted by 1 to 3 substituents selected from
   (a) a halogen atom (e.g., fluorine atom), and
   (b) a $C_{1-6}$ alkoxy group (e.g., methoxy) and the like. When the number of the substituents is two or more, the respective substituents may be the same or different.

In addition, the $C_{3-10}$ cycloalkyl group, $C_{3-10}$ cycloalkenyl group, $C_{4-10}$ cycloalkadienyl group, $C_{6-14}$ aryl group, $C_{7-13}$ aralkyl group and $C_{8-13}$ arylalkenyl group, exemplified as the aforementioned "hydrocarbon group", optionally having 1 to 3 substituents at substitutable position(s).

Examples of Such Substituent Include
(1) the groups exemplified as the substituents for the aforementioned $C_{1-10}$ alkyl group and the like;
(2) a $C_{1-6}$ alkyl group optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by a $C_{1-6}$ alkyl group;
(3) a $C_{2-6}$ alkenyl group (e.g., ethenyl, 1-propenyl) optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by a $C_{1-6}$ alkyl group;
(4) a $C_{7-13}$ aralkyl group (e.g., benzyl) optionally substituted by 1 to 3 substituents selected from
   (a) a $C_{1-6}$ alkyl group optionally substituted by 1 to 3 halogen atoms, (b) a hydroxy group,
(c) a $C_{1-6}$ alkoxy group, and
(d) a halogen atom;
and the like. When the number of the substituents is two or more, the respective substituents may be the same or different.

$R^{A1}$, $R^{A2}$, $R^{A3}$ and $R^{A4}$ are preferably each independently a $C_{1-6}$ alkyl group, more preferably, independently methyl, ethyl or isopropyl, still more preferably, isopropyl.

$R^1$ is a hydroxy group or an optionally substituted $C_{1-6}$ alkoxy group.

The "$C_{1-6}$ alkoxy group" of the "optionally substituted $C_{1-6}$ alkoxy group" for $R^1$ optionally has 1 to 3 substituents at substitutable position(s). Examples of such substituent include those similar to the substituents that the $C_{1-10}$ alkyl group and the like exemplified as the "hydrocarbon group" of the "optionally substituted hydrocarbon group" for $R^{A1}$, $R^{A2}$, $R^{A3}$ or $R^{A4}$ optionally has.

$R^1$ is preferably a hydroxy group or a $C_{1-6}$ alkoxy group, more preferably, a hydroxy group or methoxy, still more preferably, a hydroxy group.

X is a halogen atom, a hydroxy group or an optionally substituted $C_{1-6}$ alkoxy group.

Examples of the "optionally substituted $C_{1-6}$ alkoxy group" for X include those similar to the "optionally substituted $C_{1-6}$ alkoxy group" for $R^1$.

X is preferably a halogen atom, a hydroxy group or a $C_{1-6}$ alkoxy group, more preferably, a hydroxy group.

$R^{B1}$ is an optionally substituted $C_{6-14}$ aryl group.

$R^{B2}$ and $R^{B3}$ are each independently an optionally substituted $C_{6-14}$ aryl group.

The "$C_{6-14}$ aryl group" of the "optionally substituted $C_{6-14}$ aryl group" for $R^{B1}$, $R^{B2}$ or $R^{B3}$ optionally has 1 to 3 substituents at substitutable position(s). Examples of such substituent include those similar to the substituents that the $C_{3-10}$ cycloalkyl group and the like exemplified as the "hydrocarbon group" of the "optionally substituted hydrocarbon group" for $R^{A1}$, $R^{A2}$, $R^{A3}$ or $R^{A4}$ optionally has.

$R^{B1}$, $R^{B2}$ and $R^{B3}$ are each preferably phenyl.

L is an optically active form of 1,2-bis(2,5-diisopropylphosphorano)benzene.

La is an optically active form of 1,2-bis(2,5-diethylphosphorano)benzene, or an optically active form of 1,2-bis(2,5-dimethylphosphorano)ethane.

dmf is N,N-dimethylformamide.

n is an integer of one or more.

$R^2$ is a $C_{1-6}$ alkoxy group.

$R^2$ is preferably methoxy.

Y is a leaving group.

Examples of the aforementioned leaving group for Y include a halogen atom, an optionally halogenated $C_{1-6}$ alkylsulfonyloxy group (e.g., methanesulfonyloxy, ethanesulfonyloxy, trichloromethanesulfonyloxy, trifluoromethanesulfonyloxy), a $C_{6-10}$ arylsulfonyloxy group optionally having substituent(s) [for example, a $C_{6-10}$ arylsulfonyloxy group (e.g., phenylsulfonyloxy, naphthylsulfonyloxy) optionally having 1 to 3 substituents selected from $C_{1-6}$ alkyl group, $C_{1-6}$ alkoxy group and nitro group and the like; specific examples include phenylsulfonyloxy, m-nitrophenylsulfonyloxy, p-toluenesulfonyloxy and the like], an acyloxy group (e.g., trichloroacetoxy, trifluoroacetoxy) and the like.

Y is preferably a halogen atom, or an optionally halogenated $C_{1-6}$ alkylsulfonyloxy group, more preferably a halogen atom, methanesulfonyloxy or trifluoromethanesulfonyloxy.

Y is more preferably a halogen atom.

Y is most preferably a chlorine atom.

$R^3$ is a hydroxy group or an optionally substituted $C_{1-6}$ alkoxy group.

Examples of the "optionally substituted $C_{1-6}$ alkoxy group" for $R^3$ include those similar to the "optionally substituted $C_{1-6}$ alkoxy group" for $R^1$.

$R^3$ is preferably a hydroxy group or a $C_{1-6}$ alkoxy group, more preferably, a hydroxy group or methoxy.

$R^4$ is a formyl group or a hydroxymethyl group.

Z is a halogen atom.

Z is preferably bromine atom.

Preferable embodiments in the present invention are as follows.

[Production Method (A-1)]

A method of producing an optically active form of a compound represented by the formula:

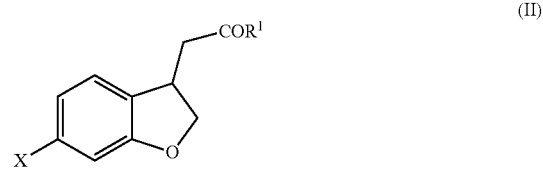

wherein $R^1$ is a hydroxy group or a $C_{1-6}$ alkoxy group (preferably, a hydroxy group); and
X is a halogen atom, a hydroxy group or a $C_{1-6}$ alkoxy group (preferably, a hydroxy group),
or a salt thereof, comprising a step of subjecting a compound represented by the formula:

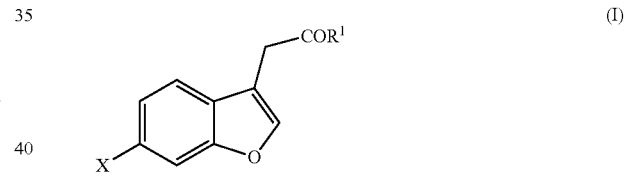

wherein $R^1$ is a hydroxy group or a $C_{1-6}$ alkoxy group (preferably, a hydroxy group); and
X is a halogen atom, a hydroxy group or a $C_{1-6}$ alkoxy group (preferably, a hydroxy group),
or a salt thereof, to an asymmetric hydrogenation reaction in the presence of a ruthenium complex.

[Production Method (A-2)]

A method of producing an optically active form of a compound represented by the formula:

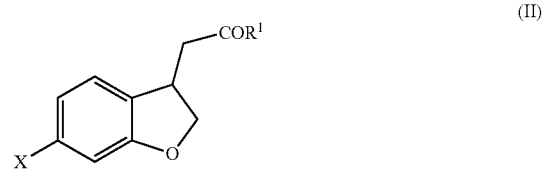

wherein $R^1$ is a hydroxy group or a $C_{1-6}$ alkoxy group (preferably, a hydroxy group); and
X is a halogen atom, a hydroxy group or a $C_{1-6}$ alkoxy group (preferably, a hydroxy group),
or a salt thereof, comprising a step of subjecting a compound represented by the formula:

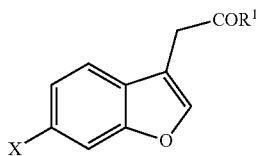

(I)

wherein R$^1$ is a hydroxy group or a C$_{1-6}$ alkoxy group (preferably, a hydroxy group); and
X is a halogen atom, a hydroxy group or a C$_{1-6}$ alkoxy group (preferably, a hydroxy group),
or a salt thereof, to an asymmetric hydrogenation reaction in the presence of a ruthenium complex,
wherein the aforementioned ruthenium complex comprises a compound represented by the formula:

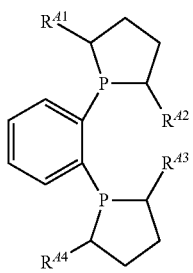

(III)

wherein R$^{A1}$, R$^{A2}$, R$^{A3}$ and R$^{A4}$ are each an isopropyl group, as a ligand.

[Production Method (A-3)]

A method of producing an optically active form of a compound represented by the formula:

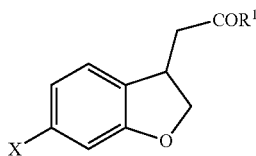

(II)

wherein R$^1$ is a hydroxy group or a C$_{1-6}$ alkoxy group (preferably, a hydroxy group); and
X is a halogen atom, a hydroxy group or a C$_{1-6}$ alkoxy group (preferably, a hydroxy group),
or a salt thereof, comprising a step of subjecting a compound represented by the formula:

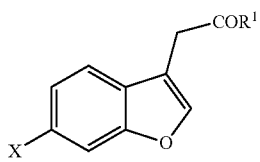

(I)

wherein R$^1$ is a hydroxy group or a C$_{1-6}$ alkoxy group (preferably, a hydroxy group); and
X is a halogen atom, a hydroxy group or a C$_{1-6}$ alkoxy group (preferably, a hydroxy group),
or a salt thereof, to an asymmetric hydrogenation reaction in the presence of a ruthenium complex,
wherein the aforementioned ruthenium complex is a complex represented by the formula:

$$RuCl_2(L)(dmf)_n \qquad (V)$$

wherein L is an optically active form of 1,2-bis(2,5-diisopropylphosphorano)benzene;
dmf is N,N-dimethylformamide; and,
n is an integer of one or more.

[Production Method (B-1)]

A method of producing an optically active form of a compound represented by the formula:

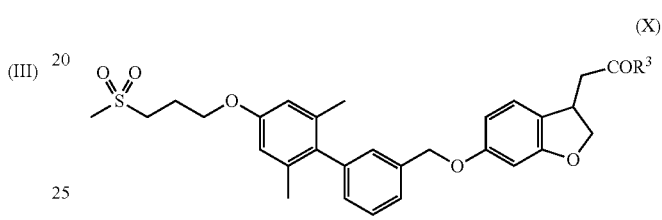

(X)

wherein R$^3$ is a hydroxy group or a C$_{1-6}$ alkoxy group (preferably, a C$_{1-6}$ alkoxy group),
or a salt thereof, comprising (1) a step of producing an optically active form of a compound represented by the formula:

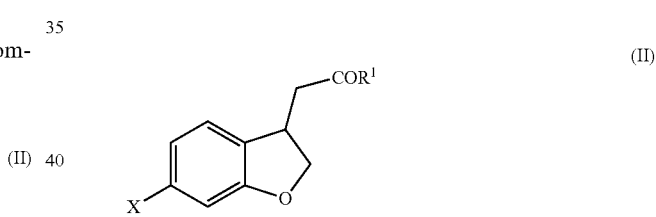

(II)

wherein R$^1$ is a hydroxy group or a C$_{1-6}$ alkoxy group (preferably, a hydroxy group); and
X is a halogen atom, a hydroxy group or a C$_{1-6}$ alkoxy group (preferably, a hydroxy group),
or a salt thereof, by subjecting a compound represented by the formula:

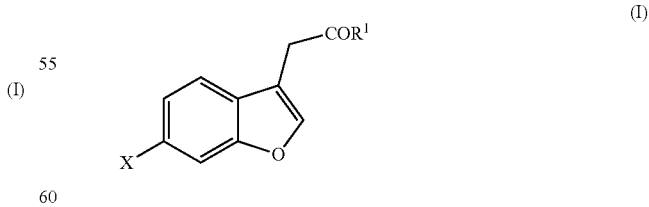

(I)

wherein R$^1$ is a hydroxy group or a C$_{1-6}$ alkoxy group (preferably, a hydroxy group); and
X is a halogen atom, a hydroxy group or a C$_{1-6}$ alkoxy group (preferably, a hydroxy group),
or a salt thereof, to an asymmetric hydrogenation reaction in the presence of a ruthenium complex; and (2) a step of reacting a compound represented by the formula:

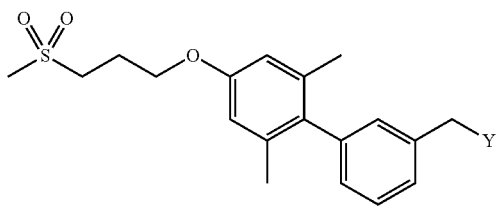
(IX)

wherein Y is a leaving group,
or a salt thereof, with an optically active form of a compound represented by the formula:

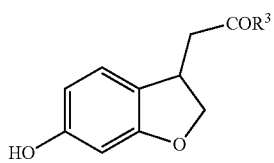
(VIIIa)

wherein $R^3$ is a hydroxy group or a $C_{1-6}$ alkoxy group (preferably, $C_{1-6}$ alkoxy group),
or a salt thereof.

[Production Method (B-2)]

A method of producing an optically active form of a compound represented by the formula:

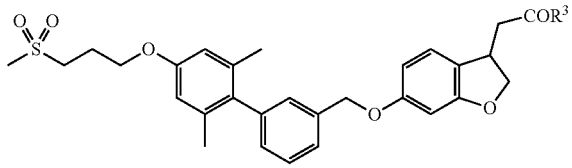
(X)

wherein $R^3$ is a hydroxy group or a $C_{1-6}$ alkoxy group (preferably, a $C_{1-6}$ alkoxy group),
or a salt thereof, comprising
(1) a step of producing an optically active form of a compound represented by the formula:

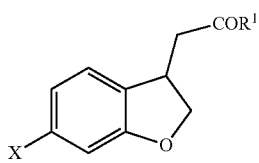
(II)

wherein $R^1$ is a hydroxy group or a $C_{1-6}$ alkoxy group (preferably, a hydroxy group); and
X is a halogen atom, a hydroxy group or a $C_{1-6}$ alkoxy group (preferably, a hydroxy group),
or a salt thereof, by subjecting a compound represented by the formula:

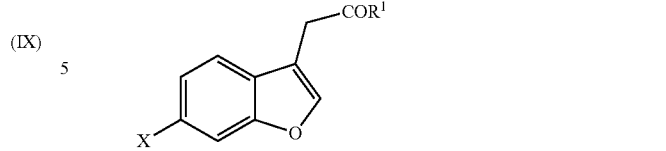
(I)

wherein $R^1$ is a hydroxy group or a $C_{1-6}$ alkoxy group (preferably, a hydroxy group); and
X is a halogen atom, a hydroxy group or a $C_{1-6}$ alkoxy group (preferably, a hydroxy group),
or a salt thereof, to an asymmetric hydrogenation reaction in the presence of a ruthenium complex; and
(2) a step of reacting a compound represented by the formula:

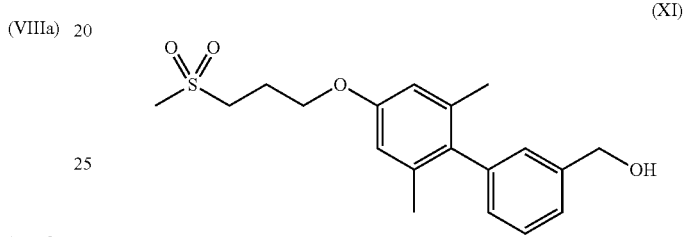
(XI)

or a salt thereof, with an optically active form of a compound represented by the formula:

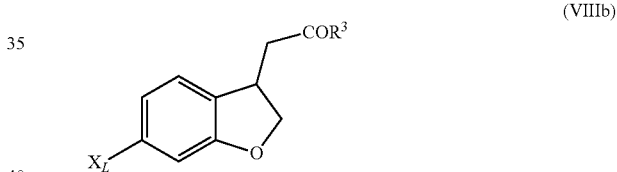
(VIIIb)

wherein $R^3$ is a hydroxy group or an optionally substituted $C_{1-6}$ alkoxy group (preferably, a $C_{1-6}$ alkoxy group); and
$X_L$ is a leaving group (preferably, an optionally halogenated $C_{1-6}$ alkylsulfonyloxy group),
or a salt thereof.

Examples of salts of compounds represented by the formulas (I), (II), (IVa1), (IVb1), (IVa), (IVb), (VIII), (VIIIa), (VIIIb), (IX), (X), (XI), (XII), (XIII), (XIV) and (XV) include metal salt, ammonium salt, salt with organic base, salt with inorganic acid, salt with organic acid, salt with basic or acidic amino acid and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with inorganic acid include salt with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like, and preferable examples of the salt with acidic amino acid include salts with aspartic acid, glutamic acid and the like.

Among the above-mentioned salts, a pharmaceutically acceptable salt is preferable.

In the following, a production method of an optically active form of a compound represented by the formula:

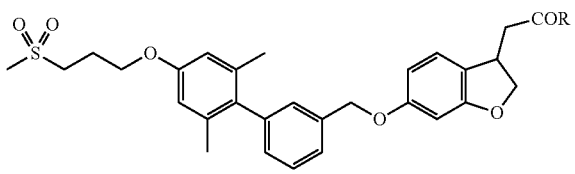

(XVI)

wherein R is a hydroxy group or an optionally substituted $C_{1-6}$ alkoxy group, or a salt thereof (hereinafter to be also referred to as compound (XVI)) is explained.

Examples of the above-mentioned "optionally substituted $C_{1-6}$ alkoxy group" for R include those similar to the aforementioned "optionally substituted $C_{1-6}$ alkoxy group" for $R^1$.

Unless otherwise specified, each symbol in the compounds in the following reaction schemes is as defined above. Each compound in the reaction schemes may form a salt as long as it does not inhibit the reaction. Examples of such salt are those similar to the aforementioned salts.

The compound obtained in each step can also be used for the next reaction as a crude product in a reaction mixture. It can also be isolated from the reaction mixture according to a conventional method, and easily purified by a separation means such as recrystallization, distillation, chromatography and the like.

Compound (XVI) is produced by reacting an optically active form of a compound represented by the formula:

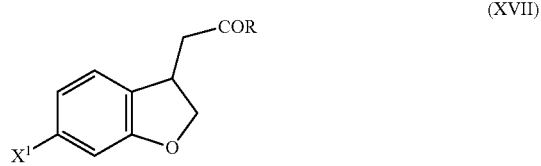

(XVII)

wherein R is a hydroxy group or an optionally substituted $C_{1-6}$ alkoxy group, $X^1$ is a leaving group, or a hydroxy group, or a salt thereof (hereinafter to be also referred to as compound (XVII)), with a compound represented by the formula:

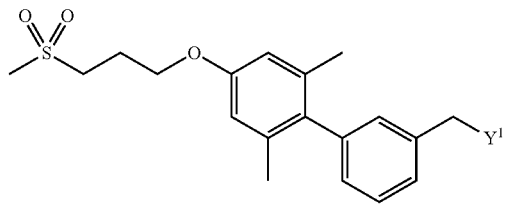

(XVIII)

wherein $Y^1$ is a leaving group, or a hydroxy group, or a salt thereof (hereinafter to be also referred to as compound (XVIII)). When $X^1$ is a leaving group, $Y^1$ is a hydroxy group, and when $X^1$ is a hydroxy group, $Y^1$ is a leaving group.

Examples of the leaving group for the aforementioned $X^1$ include a halogen atom, an optionally halogenated $C_{1-6}$ alkylsulfonyloxy group (e.g., methanesulfonyloxy, ethanesulfonyloxy, trichloromethanesulfonyloxy, trifluoromethanesulfonyloxy), a $C_{6-10}$ arylsulfonyloxy group optionally having substituent(s) [for example, a $C_{6-10}$ arylsulfonyloxy group (e.g., phenylsulfonyloxy, naphthylsulfonyloxy) optionally having 1 to 3 substituents selected from a $C_{1-6}$ alkyl group, a $C_{1-6}$ alkoxy group and a nitro group and the like; specific examples include phenylsulfonyloxy, m-nitrophenylsulfonyloxy, p-toluenesulfonyloxy and the like], an acyloxy group (e.g., trichloroacetoxy, trifluoroacetoxy) and the like.

When $X^1$ is used as a leaving group, trifluoromethanesulfonyloxy is preferable, which can be produced, for example, by reacting an optically active form of a compound represented by the formula:

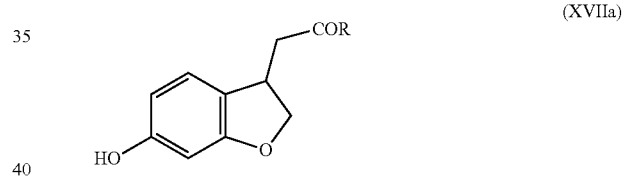

(XVIIa)

wherein R is a hydroxy group or an optionally substituted $C_{1-6}$ alkoxy group, or a salt thereof (hereinafter to be also referred to as compound (XVIIa)) with trifluoromethanesulfonic anhydride.

This reaction is generally performed in a solvent, and a base convenient for promoting the reaction may be added. Examples of the solvent include hydrocarbons such as benzene, toluene and the like; ethers such as ethylether, dioxane, tetrahydrofuran and the like; esters such as ethyl acetate and the like; halogenated hydrocarbons such as chloroform, dichloromethane and the like; amides such as N,N-dimethylformamide and the like; aromatic amines such as pyridine and the like; water and the like, which may be used in an appropriate mixture.

Examples of the above-mentioned base include alkali metal hydroxide such as sodium hydroxide, potassium hydroxide and the like; hydrogencarbonates such as sodium hydrogen carbonate, potassium hydrogen carbonate and the like; carbonate such as sodium carbonate, potassium carbonate and the like; acetate such as sodium acetate and the like; tertiary amines such as trimethylamine, triethylamine, N-methylmorpholine and the like; aromatic amines such as pyridine, picoline, N,N-dimethylaniline and the like; and the like. The amount of the base to be used is, for example, about 0.5-about 100 mol, preferably about 1-about 10 mol, per 1 mol of compound (XVIIa).

The amount of trifluoromethanesulfonic anhydride to be used is generally about 0.5-about 10 mol, preferably about 1-about 3 mol, per 1 mol of compound (XVIIa).

The reaction temperature is generally about −20° C.-about 150° C., preferably about −10° C.-about 50° C. and the reaction time is generally about 1 min-about 24 hr, preferably about 30 min-about 16 hr.

Examples of the leaving group for the aforementioned $Y^1$ include those similar to the above-mentioned leaving group for $X^1$.

$Y^1$ is preferably used as a leaving group, and a halogen atom, methanesulfonyloxy or trifluoromethanesulfonyloxy is more preferable. $Y^1$ is more preferably a halogen atom, and most preferably a chlorine atom.

$Y^1$ is most preferably a chlorine atom, and $X^1$ is most preferably a hydroxy group.

The production of compound (XVII) is explained in the following.

An optically active form of a compound represented by the formula:

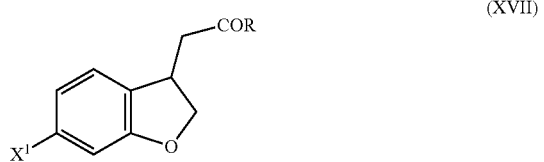

wherein each symbol is as defined above,
or a salt thereof.

As shown in reaction scheme 1, compound (II) can be produced by subjecting compound (I) to an asymmetric hydrogenation reaction.

reaction scheme 1

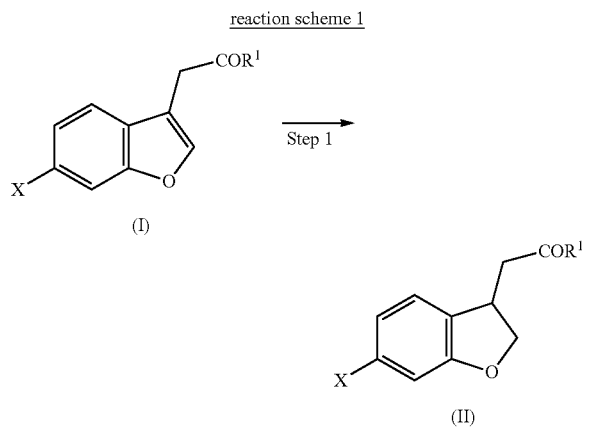

wherein each symbol is as defined above.

The asymmetric hydrogenation reaction is desirably performed in the presence of a ruthenium complex as an asymmetric catalyst. More preferably, it is desirably performed in the presence of a base.

Specific examples of the ruthenium complex include those recited below (in the following complexes, L is an optically active diphosphine ligand, Ar is benzene optionally having substituent(s), Tf is trifluoromethanesulfonyl, nbd is norbornadiene, Ph is phenyl, Ac is acetyl, Et is ethyl, dmf is N,N-dimethylformamide, and 2-methylallyl is $\eta^3$-2-methylallyl, n is one or more integers).

[RuCl$_2$(L)]$_n$, [RuBr$_2$(L)]$_n$, [RuI$_2$(L)]$_n$, [Ru(OAc)$_2$(L)], [Ru(O$_2$CCF$_3$)$_2$(L)], (NH$_2$Me$_2$) [{RuCl(L)}$_2$(μ-Cl)$_3$], (NH$_2$Et$_2$) [{RuCl(L)}$_2$(μ-Cl)$_3$], (NH$_2$Me$_2$) [{RuBr(L)}$_2$(μ-Br)$_3$], (NH$_2$Et$_2$) [{RuBr(L)}$_2$(μ-Br)$_3$], (NH$_2$Me$_2$) [{RuI(L)}$_2$(μ-I)$_3$], (NH$_2$Et$_2$) [{RuI(L)}$_2$(μ-I)$_3$], [Ru$_2$Cl$_4$(L)$_2$(NEt$_3$)], [RuCl$_2$(L)(dmf)$_n$], [Ru(2-methylallyl)$_2$(L)], [RuCl(Ar)(L)]Cl, [RuCl(Ar)(L)]Br, [RuCl(Ar)(L)]I, [RuCl(Ar)(L)]OTf, [RuCl(Ar)(L)]ClO$_4$, [RuCl(Ar)(L)]PF$_6$, [RuCl(Ar)(L)]BF$_4$, [RuCl(Ar)(L)]BPh$_4$, [RuBr(Ar)(L)]Cl, [RuBr(Ar)(L)]Br, [RuBr(Ar)(L)]I, [RuI(Ar)(L)]Cl, [RuI(Ar)(L)]Br, [RuI(Ar)(L)]I, [Ru(L)](OTf)$_2$, [Ru(L)](BF$_4$)$_2$, [Ru(L)](ClO$_4$)$_2$, [Ru(L)](PF$_6$)$_2$, [Ru(L)](BPh$_4$)$_2$, [RuH(L)$_2$]Cl, [RuH(L)$_2$]OTf, [RuH(L)$_2$]BF$_4$, [RuH(L)$_2$]ClO$_4$, [RuH(L)$_2$]PF$_6$, [RuH(L)$_2$]BPh$_4$, [RuH(CH$_3$CN)(L)]Cl, [RuH(CH$_3$CN)(L)]OTf, [RuH(CH$_3$CN)(L)]BF$_4$, [RuH(CH$_3$CN)(L)]ClO$_4$, [RuH(CH$_3$CN)(L)]PF$_6$, [RuH(CH$_3$CN)(L)]BPh$_4$, [RuCl(L)]OTf, [RuCl(L)]BF$_4$, [RuCl(L)]ClO$_4$, [RuCl(L)]PF$_6$, [RuCl(L)]BPh$_4$, [RuBr(L)]OTf, [RuBr(L)]BF$_4$, [RuBr(L)]ClO$_4$, [RuBr(L)]PF$_6$, [RuBr(L)]BPh$_4$, [RuI(L)]OTf, [RuI(L)]BF$_4$, [RuI(L)]ClO$_4$, [RuI(L)]PF$_6$, [RuI(L)]BPh$_4$ Among these, [RuCl$_2$(L)(dmf)$_n$] is preferable.

Examples of the above-mentioned optically active diphosphine include 2,2'-bis-(diphenylphosphino)-1,1'-binaphthyl (hereinafter sometimes to be abbreviated as BINAP); a BINAP derivative having a substituent such as a $C_{1-6}$ alkyl group, a $C_{6-14}$ aryl group and the like on the naphthyl ring of BINAP, for example, 2,2'-bis-(diphenylphosphino)-6,6'-dimethyl-1,1'-binaphthyl; a BINAP derivative having a partially hydrogenated naphthyl ring of BINAP, for example, 2,2'-bis-(diphenylphosphino)-5,6,7,8,5',6',7',8'-octahydro-1,1'-binaphthyl (H8 BINAP); a BINAP derivative having 1 to 5 substituents such as a $C_{1-6}$ alkyl group and the like on one benzene ring on the phosphorus atom of BINAP, for example, 2,2'-bis-(di-p-tolylphosphino)-1,1'-binaphthyl (tol-BINAP), 2,2'-bis[bis(3,5-dimethylphenyl)phosphino]-1,1'-binaphthyl (xyl-BINAP); 2,2'-bis(dicyclohexylphosphino)-6,6'-dimethyl-1,1'-biphenyl (BICHEP), 2,2'-bis(diphenylphosphino)-6,6'-dimethoxybiphenyl (MeO-BIPHEP), 2,3-bis(diphenylphosphino)butane (CHIRAPHOS), 1-cyclohexyl-1,2-bis(diphenylphosphino)ethane (CYCPHOS), 1,2-bis[(2-methoxyphenyl)phenylphosphino]ethane (DIPAMP), 1,2-bis(diphenylphosphino)propane (PROPHOS), 2,4-bis(diphenylphosphino)pentane (SKEWPHOS), 1-[1',2-bis(diphenylphosphino)ferrocenyl]ethylenediamine (BPPFA), 1-substituted-3,4-bis(diphenylphosphino)pyrrolidine (DEGPHOS), 2,3-O-isopropylidene-2,3-dihydroxy-1,4-bis(diphenylphosphino)butane (DIOP), substituted-1,2-bisphosphoranobenzene (DuPHOS), substituted-1,2-bisphosphoranoethane (BPE), 5,6-bis-(diphenylphosphino)-2-norbornene (NORPHOS), N,N'-bis(diphenylphosphino)-N,N'-bis(1-phenylethyl)ethylenediamine (PNNP), 2,2'-diphenylphosphino-1,1'-bicyclopentyl (BICP), 4,12-bis(diphenylphosphino)-[2,2]-paracyclophane (PhanePHOS), N-substituted-N-diphenylphosphino-1-[2-(diphenylphosphino)ferrocenyl]ethylamine (BoPhoz), 1-[2-(2-substituted phosphino)ferrocenyl]ethyl-2-substituted phosphine (Josiphos), 1-[2-(2'-2-substituted phosphinophenyl)ferrocenyl]ethyl-2-substituted phosphine (Walphos), 2,2'-bis(α-N,N-dimethylaminophenylmethyl)-1,1'-bis(2-substituted phosphino)ferrocene (Mandyphos), 2-substituted phosphino-2-[α-(N,N-dimethylamino)-o-2-substituted phosphinophenyl-methyl]ferrocene (Taniaphos), 1,1-bis(2-substituted-phosphotano)ferrocene (FerroTANE), 7,7'-bis(diphenylphosphino)-3,3',4,4'-tetrahydro-4,4'-dimethyl-8,8'-bi(2H-1,4-benzoxazin) (Solphos) and the like. Among the above-mentioned optically active ligand, substituted-1,2-bisphosphoranobenzene (DuPHOS), substituted-1,2-bisphosphoranoethane (BPE) and the like are preferable.

Among the substituted-1,2-bisphosphoranoethane (BPE), an optically active form of a compound represented by the formula:

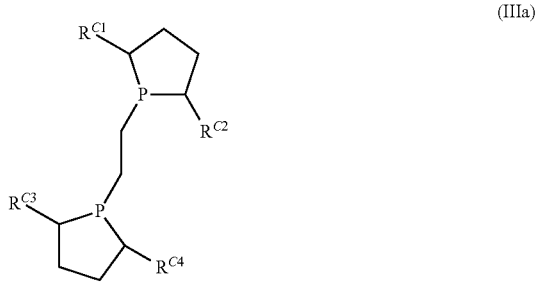

(IIIa)

wherein $R^{C1}$, $R^{C2}$, $R^{C3}$ and $R^{C4}$ are each independently an optionally substituted hydrocarbon group,
(hereinafter to be also referred to as compound (IIIa)) is preferable.

Examples of the "optionally substituted hydrocarbon group" for $R^{C1}$, $R^{C2}$, $R^{C3}$ or $R^{C4}$ include those similar to the aforementioned "optionally substituted hydrocarbon group" for $R^{A1}$, $R^{A2}$, $R^{A3}$ or $R^{A4}$. $R^{C1}$, $R^{C2}$, $R^{C3}$ and $R^{C4}$ are each independently preferably a methyl group or a phenyl group. Of these, a methyl group is most preferable.

Substituted-1,2-bisphosphoranobenzene (DuPHOS) is more preferable. Of the substituted-1,2-bisphosphoranobenzene (DuPHOS), an optically active form of compound (III) is more preferable.

An optically active form of a compound represented by the formula:

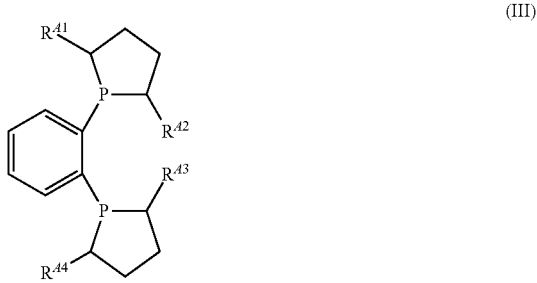

(III)

wherein each symbol is as defined above.

$R^{A1}$, $R^{A2}$, $R^{A3}$ and $R^{A4}$ are each independently preferably a methyl group, an ethyl group or an isopropyl group. Of these, an ethyl group or an isopropyl group is preferable, and an isopropyl group is most preferable. Most preferable example of an optically active form of compound (III) is an optically active form of 1,2-bis(2,5-diisopropylphosphorano)benzene.

Most preferable examples of the ruthenium complex include compound (V).

A complex represented by the formula: $[RuCl_2(L)(dmf)_n]$ (V)
wherein L is an optically active form of 1,2-bis(2,5-diisopropylphosphorano)benzene;
dmf is N,N-dimethylformamide; and,
n is an integer of one or more.

n is preferably 1 to 4.

When compound (V) is used as a catalyst, compounds (V) different in n may be used in the form of a mixture.

For production of an S form of compound (II), when an optically active form of compound (III) wherein $R^{A1}$, $R^{A2}$, $R^{A3}$ and $R^{A4}$ are methyl groups or ethyl groups is an optically active diphosphine ligand, an optically active form of compound (III) is preferably an S form, when an optically active form of compound (III) wherein $R^{A1}$, $R^{A2}$, $R^{A3}$ and $R^{A4}$ are isopropyl groups is an optically active diphosphine ligand, an optically active form of compound (III) is preferably an R form. For production of an S form of compound (II), when compound (IIIa) wherein $R^{C1}$, $R^{C2}$, $R^{C3}$ and $R^{C4}$ are methyl groups is an optically active diphosphine ligand, an optically active form of compound (IIIa) is preferably an S form; when an optically active form of compound (IIIa) wherein $R^{C1}$, $R^{C2}$, $R^{C3}$ and $R^{C4}$ are phenyl groups is an optically active diphosphine ligand, an optically active form of compound (IIIa) is preferably an R form.

For production of an R form of compound (II), when an optically active form of compound (III) wherein $R^{A1}$, $R^{A2}$, $R^{A3}$ and $R^{A4}$ are methyl groups or ethyl groups is an optically active diphosphine ligand, an optically active form of compound (III) is preferably an R form, when an optically active form of compound (III) wherein $R^{A1}$, $R^{A2}$, $R^{A3}$ and $R^{A4}$ are isopropyl groups is an optically active diphosphine ligand, an optically active form of compound (III) is preferably an S form. For production of an R form of compound (II), when compound (IIIa) wherein $R^{C1}$, $R^{C2}$, $R^{C3}$ and $R^{C4}$ are methyl groups is an optically active diphosphine ligand, an optically active form of compound (IIIa) is preferably an R form; when an optically active form of compound (IIIa) wherein $R^{C1}$, $R^{C2}$, $R^{C3}$ and $R^{C4}$ are phenyl groups is an optically active diphosphine ligand, an optically active form of compound (IIIa) is preferably an S form.

A ruthenium complex produced from an optically active diphosphine and a ruthenium complex to be a metal source by a known means, and isolated or purified by a known means (e.g., concentration, solvent extraction, fractionation, crystallization, recrystallization, chromatography) can be used.

In addition, a ruthenium complex can also be prepared by adding optically active diphosphine and a ruthenium complex to be a metal source to the reaction system.

While the amount of the ruthenium complex to be used varies depending on the reaction container, form of reaction and the like, it is, for example, about 0.1-about 0.00001 mol per 1 mol of compound (I).

As the base to be used for this reaction, an inorganic base or an organic base can be used.

Examples of the inorganic base include alkali metal hydroxides such as lithium hydroxide, potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like; carbonates such as sodium carbonate, potassium carbonate, cesium carbonate and the like; hydrogencarbonates such as sodium hydrogen carbonate, potassium hydrogen carbonate and the like; acetates such as sodium acetate, potassium acetate and the like; phosphates such as tripotassium phosphate, sodium phosphate and the like; monohydrogen phosphates such as potassium monohydrogen phosphate, sodium monohydrogen phosphate and the like; and the like.

Examples of the organic base include aliphatic amines such as trimethylamine, triethylamine, N-methylmorpholine, N,N-diisopropylethylamine, diethylamine, diisopropylamine, cyclohexylamine, ethylenediamine and the like; aromatic amines such as pyridine, picoline, N,N-dimethylaniline and the like; and the like.

As a specific inorganic base, lithium hydroxide, potassium hydroxide, sodium hydroxide, potassium tert-butoxide, sodium methoxide, sodium carbonate, potassium carbonate, cesium carbonate, sodium monohydrogen phosphate, and tripotassium phosphate are preferable; as an organic base, aliphatic amine is more preferable.

The amount of the base to be used is about 0.01 to about 100 mol, preferably about 0.1 to about 10 mol, per 1 mol of compound (I).

This reaction is generally carried out in a solvent. While the solvent is not particularly limited as long as it is inert to the reaction and can solubilize the starting compound and the catalyst, for example, aromatic hydrocarbons such as toluene, xylene and the like; aliphatic hydrocarbons such as heptane, hexane and the like; halogenated hydrocarbons such as methylene chloride and the like; ethers such as diethyl ether, tetrahydrofuran and the like; alcohols such as methanol, ethanol, 2-propanol, butanol, benzyl alcohol and the like; nitriles such as acetonitrile and the like; amides such as N,N-dimethylformamide and the like; sulfoxides such as dimethyl sulfoxide and the like, and the like can be used. These solvents may be used in a mixture at an appropriate ratio. The solvent is preferably alcohol, and methanol is particularly preferable.

The above-mentioned solvents are preferably used for the reaction after drying and deaeration.

The amount of the solvent to be used is appropriately determined according to the solubility of compound (I) and the like. For example, when alcohol (preferably methanol) is used as a solvent, the reaction can be performed almost without solvent or in a solvent in a 100-fold or more weight relative to compound (I). Generally, a solvent in about 2- to about 50-fold weight relative to compound (I) is preferably used.

Hydrogenation can also be performed by any of a batch type and continuous type reactions. The hydrogenation is performed in the presence of hydrogen, and the hydrogen pressure is, for example, 0.01-200 atm, preferably 1-15 atm.

The reaction temperature is generally −30° C.-100° C., preferably 0-80° C., more preferably 10-50° C. The reaction time is generally 0.1-72 hr, preferably 1-48 hr.

Compound (II) obtained by an asymmetric reduction reaction may be purified by a known means (e.g., fractional recrystallization, chiral column method, diastereomer salt method). To obtain a salt of a compound represented by the formula (II), which has high optical purity, purification by crystallization by a diastereomer salt method is preferable.

As a base for formation of a diastereomer salt of a compound represented by the formula (II), for example, an optically active organic base compound can be used. Among the optically active organic bases,
(1) an optically active amine compound represented by the formula:

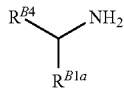

(IVa1)

wherein $R^{B1a}$ is an optionally substituted $C_{6-14}$ aryl group or an optionally substituted $C_{7-13}$ aralkyl group; and $R^{B4}$ is an optionally substituted $C_{1-6}$ alkyl group,
(hereinafter to be also referred to as compound (IVa1)); or
(2) an optically active aminoalcohol compound represented by the formula:

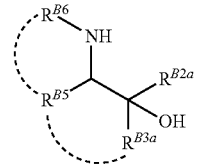

(IVb1)

wherein $R^{B2a}$ is a hydrogen atom or an optionally substituted $C_{6-14}$ aryl group; $R^{B3a}$ is an optionally substituted $C_{6-14}$ aryl group or an optionally substituted $C_{1-6}$ alkyl group; $R^{B5}$ is an optionally substituted $C_{1-6}$ alkyl group or an optionally substituted $C_{6-14}$ aryl group; $R^{B6}$ is a hydrogen atom or an optionally substituted $C_{1-6}$ alkyl group; or $R^{B3a}$ and $R^{B5}$ optionally form, together with the adjacent carbon atom, an optionally substituted 4- to 6-membered ring (said 4- to 6-membered ring is optionally fused with an optionally substituted benzene ring); or $R^{B5}$ and $R^{B6}$ optionally form, together with the adjacent nitrogen atom and carbon atom, an optionally substituted 4- to 6-membered ring (hereinafter to be also referred to as compound (IVb1)) is preferable.

Examples of the above-mentioned "optionally substituted $C_{6-14}$ aryl group" for $R^{B1a}$ include those similar to the aforementioned "optionally substituted $C_{6-14}$ aryl group" for $R^{B1}$.

Examples of the $C_{7-13}$ aralkyl group of the above-mentioned "optionally substituted $C_{7-13}$ aralkyl group" for $R^{B1a}$ include those similar to the "$C_{7-13}$ aralkyl group" exemplified as the "optionally substituted hydrocarbon group" for $R^{A1}$, $R^{A2}$, $R^{A3}$ or $R^{A4}$. The "optionally substituted $C_{7-13}$ aralkyl group" for $R^{B1a}$ may have 1 to 3 substituents at substitutable position(s). Examples of such substituent include those similar to the substituents that the aforementioned $C_{7-13}$ aralkyl group and the like exemplified as the "optionally substituted hydrocarbon group" for $R^{A1}$, $R^{A2}$, $R^{A3}$ or $R^{A4}$ may have.

Examples of the substituent of the above-mentioned "optionally substituted $C_{1-6}$ alkyl group" for $R^{B4}$ include those similar to the substituents that the aforementioned $C_{1-10}$ alkyl group and the like exemplified as the "optionally substituted hydrocarbon group" for $R^{A1}$, $R^{A2}$, $R^{A3}$ or $R^{A4}$ may have.

Examples of the above-mentioned "optionally substituted $C_{6-14}$ aryl group" for $R^{B3a}$ include those similar to the aforementioned "optionally substituted $C_{6-14}$ aryl group" for $R^{B1}$.

Examples of the substituent of the above-mentioned "optionally substituted $C_{1-6}$ alkyl group" for $R^{B3a}$ include those similar to the substituents that the aforementioned $C_{1-10}$ alkyl group and the like exemplified as the "optionally substituted hydrocarbon group" for $R^{A1}$, $R^{A2}$, $R^{A3}$ or $R^{A4}$ may have.

Examples of the above-mentioned "optionally substituted $C_{6-14}$ aryl group" for $R^{B2a}$ include those similar to the aforementioned "optionally substituted $C_{6-14}$ aryl group" for $R^{B1}$.

Examples of the substituent of the above-mentioned "optionally substituted $C_{1-6}$ alkyl group" for $R^{B5}$ include those similar to the substituents that the aforementioned $C_{1-10}$ alkyl group and the like exemplified as the "optionally substituted hydrocarbon group" for $R^{A1}$, $R^{A2}$, $R^{A3}$ or $R^{A4}$ may have.

Examples of the above-mentioned "optionally substituted $C_{6-14}$ aryl group" for $R^{B5}$ include those similar to the aforementioned "optionally substituted $C_{6-14}$ aryl group" for $R^{B1}$.

Examples of the substituent of the above-mentioned "optionally substituted $C_{1-6}$ alkyl group" for $R^{B6}$ include those similar to the substituents that the aforementioned $C_{1-10}$ alkyl group and the like exemplified as the "optionally substituted hydrocarbon group" for $R^{A1}$, $R^{A2}$, $R^{A3}$ or $R^{A4}$ may have.

When the above-mentioned $R^{B3a}$ and $R^{B5}$ form, together with the adjacent carbon atom, an optionally substituted 4- to 6-membered ring, compound (IVb1) is, for example, a compound represented by the formula:

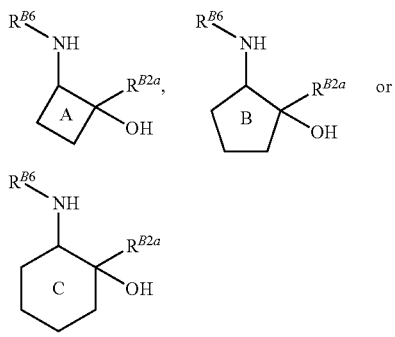

wherein ring A, ring B and ring C are optionally substituted; and other symbols are as defined above.

Examples of the substituents that the ring A, ring B and ring C optionally have include those similar to the substituents that the aforementioned $C_{1-10}$ alkyl group and the like exemplified as the "optionally substituted hydrocarbon group" for $R^{A1}$, $R^{A2}$, $R^{A3}$ or $R^{A4}$ optionally have.

When the above-mentioned optionally substituted 4- to 6-membered ring optionally formed by $R^{B3a}$ and $R^{B5}$ together with the adjacent carbon atom is further fused with an optionally substituted benzene ring to form a fused ring, compound (IVb1) is, for example, a compound represented by the formula:

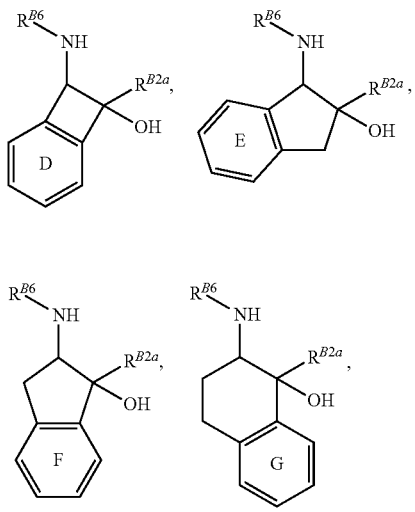

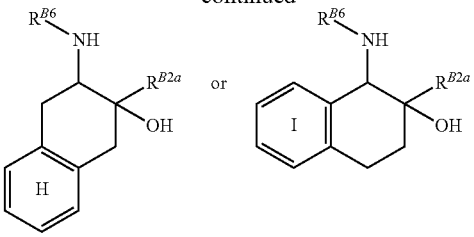

wherein ring D, ring E, ring F, ring G, ring H and ring I each independently optionally have substituent(s); and other symbols are as defined above.

Examples of the substituents that the ring D, ring E, ring F, ring G, ring H and ring I optionally have include those similar to the substituents that the aforementioned $C_{1-10}$ alkyl group and the like exemplified as the "optionally substituted hydrocarbon group" for $R^{A1}$, $R^{A2}$, $R^{A3}$ or $R^{A4}$ optionally have.

As the 4- to 6-membered ring formed by the above-mentioned $R^{B3a}$ and $R^{B5}$ together with the adjacent carbon atom, ring B and ring C are preferable and, as the fused polycycle formed by the above-mentioned $R^{B3a}$ and $R^{B5}$ together with the adjacent carbon atom, ring E, ring F, ring H and ring I are preferable.

When $R^{B5}$ and $R^{B6}$ form, together with the adjacent nitrogen atom and carbon atom, an optionally substituted 4- to 6-membered ring, compound (IVb1) is, for example, a compound represented by the formula:

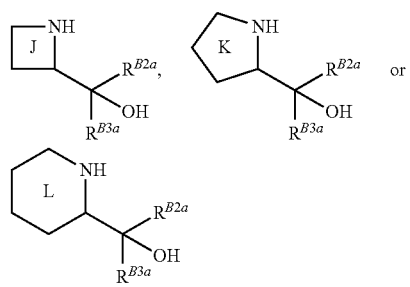

wherein ring J, ring K, and ring L optionally have substituent(s); and other symbols are as defined above.

Examples of the substituents that the ring J, ring K and ring L optionally have include those similar to the substituents that the aforementioned $C_{1-10}$ alkyl group and the like exemplified as the "optionally substituted hydrocarbon group" for $R^{A1}$, $R^{A2}$, $R^{A3}$ or $R^{A4}$ optionally have.

As the 4- to 6-membered ring formed by $R^{B5}$ and $R^{B6}$ together with the adjacent nitrogen atom and carbon atom, ring K and ring L are preferable.

Preferable examples of compound (IVa1) include 1-phenylpropylamine, 1-methyl-3-phenylpropylamine and compound (IVa).

An optically active form of a compound represented by the formula:

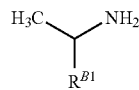

(IVa)

wherein each symbol is as defined above, or a salt thereof.

As $R^{B1}$, a phenyl group and a p-tolyl group are preferable, and a phenyl group is more preferable.

Preferable examples of compound (IVb1) include 2-amino-1,2-diphenylethanol, cis-1-aminoindan-2-ol, α,α-diphenyl-2-pyrrolidine methanol and compound (IVb).

An optically active form of a compound represented by the formula:

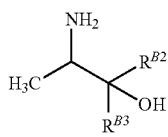

(IVb)

wherein each symbol is as defined above,
or a salt thereof.

$R^{B2}$ and $R^{B3}$ are each preferably a phenyl group.

As an optically active amine compound for producing S form of compound (II), preferable specific examples of compound (IVa1) include (R)-1-phenylethylamine, (R)-1-(p-tolyl)ethylamine, (R)-1-phenylpropylamine, and (S)-1-methyl-3-phenylpropylamine. Of these, most preferred is (R)-1-phenylethylamine.

As an optically active aminoalcohol compound for producing S form of compound (II), preferable specific examples of compound (IVb1) include (1R,2S)-2-amino-1,2-diphenylethanol, (S)-2-amino-1,1-diphenyl-1-propanol, (1S,2R)-cis-1-aminoindan-2-ol and (R)-α,α-diphenyl-2-pyrrolidine methanol. Of these, most preferred is (S)-2-amino-1,1-diphenyl-1-propanol.

As an optically active amine compound for producing R form of compound (II), preferable specific examples of compound (IVa1) include (S)-1-phenylethylamine, (S)-1-(p-tolyl)ethylamine, (S)-1-phenylpropylamine, and (R)-1-methyl-3-phenylpropylamine. Of these, most preferred is (S)-1-phenylethylamine.

As an optically active aminoalcohol compound for producing R form of compound (II), preferable specific examples of compound (IVb1) include (1S,2R)-2-amino-1,2-diphenylethanol, (R)-2-amino-1,1-diphenyl-1-propanol, (1R,2S)-cis-1-aminoindan-2-ol and (S)-α,α-diphenyl-2-pyrrolidine methanol. Of these, most preferred is (R)-2-amino-1,1-diphenyl-1-propanol.

Crystallization of compound (II) by a diastereomer salt method is generally performed in a solvent. While such solvent is not particularly limited, for example, aromatic hydrocarbons such as toluene, xylene and the like; aliphatic hydrocarbons such as heptane, hexane and the like; halogenated hydrocarbons such as methylene chloride and the like; ethers such as diethyl ether, isopropyl ether, tetrahydrofuran and the like; alcohols such as methanol, ethanol, 2-propanol, butanol, benzyl alcohol and the like; nitriles such as acetonitrile and the like; amides such as N,N-dimethylformamide and the like; sulfoxides such as dimethyl sulfoxide and the like, water and the like are used. These solvents may be used in a mixture at an appropriate ratio. As a mixed solvent, methanol-dimethyl sulfoxide-toluene, methanol-water-toluene or methanol-water-isopropyl ether is preferable.

Crystallization by a diastereomer salt method may be performed repeatedly as necessary.

As a diastereomer salt of a compound represented by the formula (II), [(3S)-6-hydroxy-2,3-dihydro-1-benzofuran-3-yl]acetic acid (1R)-1-phenylethylamine salt is preferable, a salt represented by the formula:

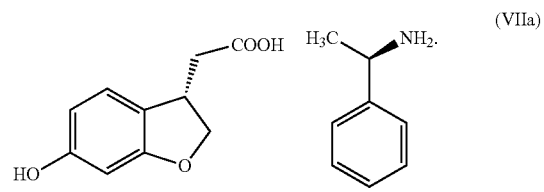

(VIIa)

Another preferable example of the diastereomer salt of the compound represented by the formula (II) is [(3S)-6-hydroxy-2,3-dihydro-1-benzofuran-3-yl]acetic acid (S)-2-amino-1,1-diphenylpropan-1-ol salt,
a salt represented by the formula:

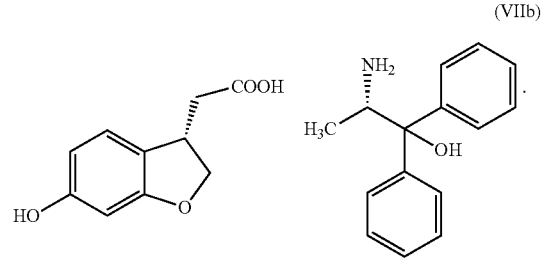 [SMILES: O=C(O)C[C@@H]1COc2cc(O)ccc21 ; C[C@H](N)C(O)(c1ccccc1)c1ccccc1]

(VIIb)

A salt of the above-mentioned compound represented by the formula (I) may be a salt with an optically active organic base used for crystallization of a diastereomer salt, and the salt is isolated and subjected to an asymmetric hydrogenation of reaction scheme 1.

Preferable optically active organic bases of a salt of a compound represented by the formula (I) are compound (IVa) and compound (IVb).

An optically active organic base to be used for the crystallization of a diastereomer salt may be added to the reaction system before the asymmetric hydrogenation reaction of reaction scheme 1. In this case, it can also be used as a base substituting the base necessary for the asymmetric hydrogenation reaction. The optically active compound (II) obtained by the asymmetric hydrogenation reaction can be isolated by direct crystallization as an optically active diastereomer salt.

When $R^1$ of compound (II) is a hydroxy group, it can be converted to compound (VIII) by an esterification reaction. An optically active form of a compound represented by the formula:

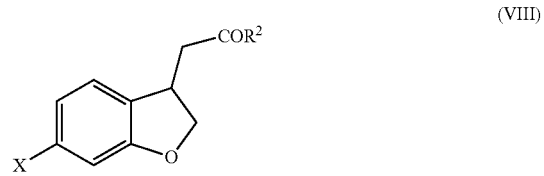

(VIII)

wherein each symbol is as defined above,
or a salt thereof.

The esterification reaction can be performed by a known means, for example, by reacting compound (II) with $C_{1-6}$ alcohol in the presence of an acid.

This reaction is often performed without solvent. When a solvent is used, for example, hydrocarbons such as benzene, toluene and the like; ethers such as ethylether, dioxane, tetrahydrofuran and the like; halogenated hydrocarbons such as chloroform, dichloromethane and the like; and the like can be used. They may be used in an appropriate mixture. Preferred are hydrocarbons such as benzene, toluene and the like.

Examples of the acid used for the above reaction include mineral acids (e.g., hydrochloric acid, hydrobromic acid, sulfuric acid etc.), phosphoric acid, sulfonic acids (e.g., methanesulfonic acid, toluenesulfonic acid etc.), Lewis acids (e.g., aluminum chloride, tin chloride, zinc bromide etc.) and the like. Where necessary, two or more kinds thereof may be used in a mixture. The amount of the acid to be used varies depending on the kind of the solvent, and other reaction conditions. It is generally not less than about 0.1 mol per 1 mol of compound (II), and the acid can also be used as a solvent. Particularly preferred is sulfuric acid.

The reaction temperature is generally about −20° C.-about 150° C., preferably about 30° C.-about 100° C. and the reaction time generally about 5 min-about 24 hr, preferably about 30 min-about 4 hr.

This reaction can be easily performed even when compound (II) is a salt.

Compound (VIII) wherein X is hydroxy and $R^2$ is methoxy is most preferable.

Most preferable production example of compound (VIII) is shown in reaction scheme 2.

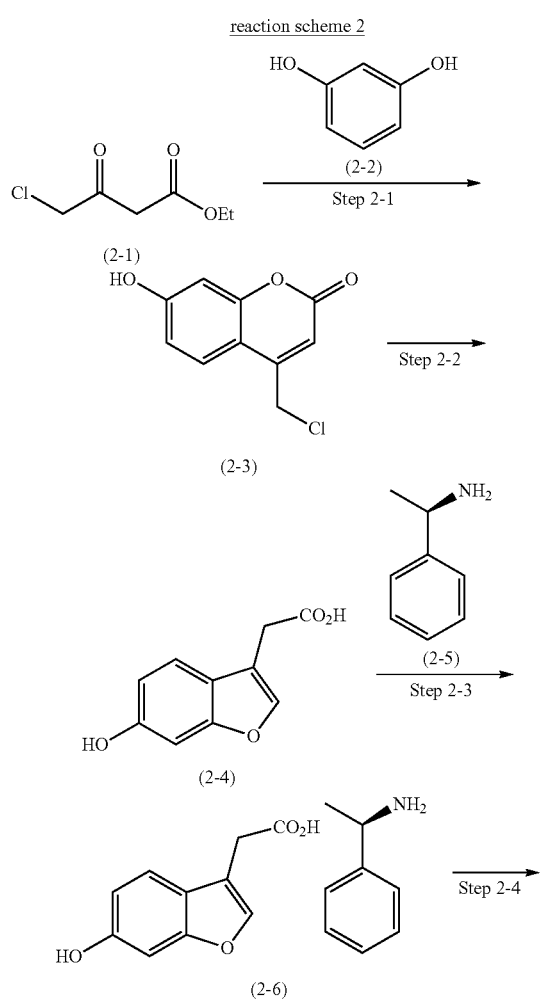

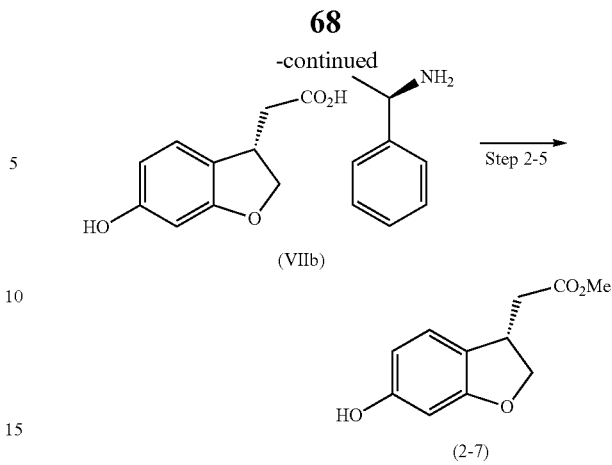

As explained in detail in the below-mentioned Examples, compound (2-4) can be synthesized, for example, by the method described in Heterocycles, No. 41, page 647-650, 1995, from compound (2-1) and compound (2-2) via compound (2-3).

The production methods of the compound (XVIII) are explained in the following.

A compound represented by the formula:

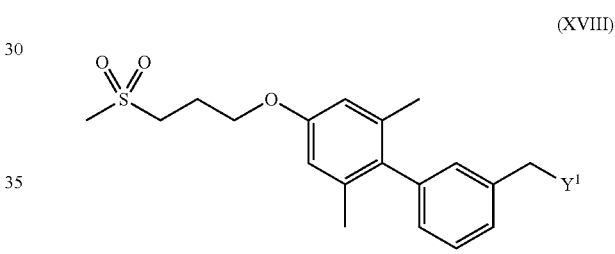

wherein each symbol is as defined above, or a salt thereof.

Compound (XIV) can be synthesized by the method shown in the following reaction scheme 3.

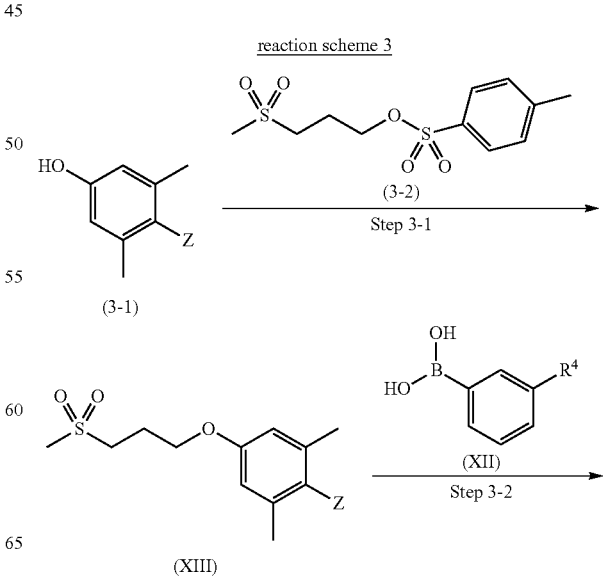

-continued (XIV)

wherein each symbol is as defined above.
Step 3-1

Compound (3-1) reacted with compound (3-2) in the presence of a base to give compound (XIII).

The solvent to be used for this reaction is not particularly limited as long as it does not influence the reaction. For example, amides such as N,N-dimethylformamide, N,N-dimethylacetamide, N-methylpiperidone and the like, dimethyl sulfoxide, hexamethylphosphoric amide, dimethylimidazolidinone and the like can be used. Of these, the above-mentioned amides are preferable. One or more kinds of these may be mixed at an appropriate ratio and used.

The amount of the solvent to be used for this reaction is 1- to 100-fold weight, preferably 3- to 50-fold weight, more preferably 5- to 20-fold weight, relative to compound (3-1).

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate, cesium carbonate and the like; alkali metal hydrogencarbonates such as sodium hydrogen carbonate and the like; alkali metal phosphates such as tripotassium phosphate and the like; acetates such as sodium acetate, ammonium acetate and the like; aromatic amines such as pyridine, lutidine and the like; tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like; alkali metal hydrides such as sodium hydride, potassium hydride and the like; metal amides such as sodium amide, lithium diisopropylamide, lithium hexamethyldisilazide and the like; alkali metal alkoxides having 1 to 6 carbon atoms such as sodium methoxide, sodium ethoxide, sodium tert-butoxide, potassium tert-butoxide and the like; organic lithiums such as methyllithium, n-butyllithium, sec-butyllithium, tert-butyllithium and the like, and the like can be mentioned. Of these, alkali metal carbonate is particularly preferable.

The amount of the base to be used is generally about 1 to about 10 mol, preferably about 1 to about 3 mol, per 1 mol of compound (3-1).

The amount of compound (3-2) to be used is generally about 0.5 to about 10 mol, preferably about 1 to about 3 mol, per 1 mol of compound (3-1).

The reaction temperature is generally −20-200° C., preferably 0-150° C., more preferably 50-100° C. The reaction time is generally 5 min-100 hr, preferably 30 min-120 hr.

Z is preferably a bromine atom.
Step 3-2

Compound (XIV) can be obtained by subjecting compound (XIII) and compound (XII) to a coupling reaction.

The coupling reaction is generally carried out in the presence of a base. As the base, for example, alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide, barium hydroxide and the like; alkali metal carbonates such as sodium carbonate, potassium carbonate, cesium carbonate and the like; alkali metal hydrogencarbonates such as sodium hydrogen carbonate, potassium hydrogencarbonate and the like; alkali metal phosphates such as tripotassium phosphate and the like; alkali metal alkoxides having 1 to 6 carbon atoms such as sodium methoxide, sodium ethoxide, sodium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; metal amides such as sodium amide, lithium diisopropylamide, lithium hexamethyldisilazide and the like, and the like can be mentioned. Of these, alkaline earth metal hydroxide, alkali metal carbonate, alkali metal phosphate, and organic bases are particularly preferable.

The amount of the base to be used is generally about 1 to about 10 mol, preferably about 1 to about 3 mol, per 1 mol of compound (XIII).

The amount of compound (XII) to be used is generally about 0.9 to about 10 mol, preferably about 1 to about 3 mol, relative to compound (XIII).

The coupling reaction is advantageously performed by using a solvent inert to the reaction. Such solvent is not particularly limited as long as the reaction proceeds. For example, alcohols such as methanol, ethanol, propanol, isopropanol, butanol, tert-butanol and the like; ethers such as 1,4-dioxane, tetrahydrofuran, diethyl ether, tert-butyl methyl ether, diisopropyl ether, 1,2-dimethoxyethane and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; water and the like can be mentioned. Of these, the above-mentioned amides and sulfoxides are preferable. One or more kinds of these may be mixed at an appropriate ratio and used. As a mixed solvent, amides-water and sulfoxides-water are particularly preferable.

The amount of the solvent to be used for this reaction is 1- to 100-fold weight, preferably 3- to 50-fold weight, particularly 5- to 20-fold weight, relative to compound (XIII).

As the palladium catalyst to be used for the coupling reaction, a palladium-phosphine complex can be mentioned. Examples thereof include (2'-di-tert-butylphosphino-1,1'-biphenyl-2-yl)palladium (II) acetate, allylchloro[1,3-bis(2,6-diisopropylphenyl)-4,5-dihydroimidazol-2-ylidene]palladium (II), allylchloro[1,3-bis(2,6-diisopropylphenyl) imidazol-2-ylidene]palladium (II), allylchloro[1,3-bis(2,4,6-trimethylphenyl)imidazol-2-ylidene]palladium (II), bis(acetato)triphenylphosphine palladium (II), bis[1,2-bis(diphenylphosphino)ethane]palladium (0), bis(dibenzylideneacetone)palladium (0), 1,3-bis(2,6-diisopropylphenyl)imidazol-2-ylidene (1,4-naphthoquinone)palladium (0) dimer, [P,P-1,3-bis(diisopropylphosphino)propane][P-1,3-bis(diisopropylphosphino)propane]palladium (0), bis(2-methylallyl)palladium chloride dimer, 1,2-bis(phenylsulfinyl)ethane palladium (II) acetate, bis(2,2,6,6- tetramethyl-3,5-heptanedionato)palladium (II), bis(tri-tert-butylphosphine)palladium (0), bis(tricyclohexylbutylphosphine)palladium (0), 1,3-bis(2,4,6-trimethylphenyl)imidazol-2-ylidene(1,4-naphthoquinone)palladium (0) dimer, bis(tri-o-tolylphosphine)palladium (0), chloro(2-di-tert-butylphosphino-2',4',6'-triisopropyl-1,1'-biphenyl) [2-(2-aminoethyl)phenyl]palladium (II), chloro(2-dicyclohexylphosphino-2',6'-dimethoxy-1,1'-biphenyl) [2-(2-aminoethyl)phenyl]palladium (II), chloro[2-(dicyclohexylphosphino)-3,6-dimethoxy-2',4',6'-triisopropyl-1,1'-biphenyl][2-(2-aminoethyl)phenyl]palladium (II), chloro(2-dicyclohexylphosphino-2',6'-diisopropyl-1,1'-biphenyl)[2-(2-aminoethyl)phenyl]palladium (II), chloro(2-dicyclohexylphosphino-2',4',6'-triisopropyl-1,1'-biphenyl) [2-(2-aminoethyl)phenyl]palladium (II), chloro(di-2-norbornylphosphino) (2'-dimethylamino-1,1'-biphenyl-2-yl)palladium (II), chloro(di-2-norbornyl-phosphino) (2-dimethylaminomethylferrocen-1-yl)palladium (II), chloro[(1,2,3η)-3-phenyl-2-propenyl][1,3-bis(2,6-diisopropylphenyl)-4,5-dihydroimidazol-2-ylidene]palladium (II), chloro[(1,2,3η)-3-phenyl-2-propenyl][1,3-bis(2,6-diisopropylphenyl)imidazol-2-ylidene]palladium (II), crotylpalladium chloride dimer, trans-di(µ-acetato)bis[o-(di-o-tolyl-phosphino)benzyl]dipalladium (II), di(acetato)dicyclohexylphenylphosphine palladium (II), diacetatobis(triphenylphosphine)palladium (II), diamine palladium (II), dibenzylideneacetone palladium (0) phosphoadamantane ethyl silica, di-µ-bromobis(tri-tert-butylphosphino)dipalladium (I), dichloro[1,1'-bis(di-tert-butylphosphino)ferrocene]palladium, dichloro [, 1'-bis(dicyclohexylphosphino)ferrocene]palladium, dichloro[(R)-(+)-2,2'-bis(diphenylphosphino)-1,1'-binaphthyl]palladium (II), dichloro[(S)-(−)-2,2'-bis(diphenylphosphino)-1,1'-binaphthyl]palladium (II), dichloro[2,2'-bis(diphenylphosphino)-1,1'-binaphthyl]palladium (II), dichloro(1,2-bis(diphenylphosphino)ethane)palladium (II), dichloro(1,1'-bis(diphenylphosphino)ferrocene)palladium (II), dichloro(1,3-bis(diphenylphosphino)propane)palladium (II), dichloro(1,1'-bis(diisopropylphosphino) ferrocene)palladium (II), dichlorobis(tricyclohexylphosphino)palladium (II), trans-dichlorobis(triphenylphosphino)palladium (II), trans-dichlorobis(tri-o-toluoylphosphino)palladium (II), dichloro[9,9-dimethyl-4,5-bis(diphenylphosphino)xanthene]palladium (II), tetrakis(triphenylphosphine)palladium (0), dichlorobis(triethylphosphine)palladium (II) and the like.

In addition, a palladium source and a phosphine compound in co-presence may be used as a palladium catalyst to perform the reaction. As the palladium source, palladium on a carrier or a palladium complex can be used.

As the carrier to support palladium, activated carbon, alumina, calcium carbonate and the like can be mentioned. Of these, activated carbon is preferable.

As the palladium supported on a carrier, palladium metal, palladium hydroxide and the like can be mentioned.

When palladium on a carrier and a phosphine compound are co-present, as the phosphine compound, dichloro(1,2-bis(diphenylphosphino)ethane), dichloro(1,1'-bis(diphenylphosphino)ferrocene), 2-(dicyclohexylphosphino)biphenyl, 2,2'-bis(diphenylphosphino)-1,1'-binaphthyl and the like can be mentioned. Of these, the above-mentioned dichloro(1,1'-bis(diphenylphosphino)ferrocene), 2,2'-bis(diphenylphosphino)-1,1'-binaphthyl is preferable.

As the palladium complex, palladium chloride, palladium acetate, dibenzylideneacetone palladium and the like can be mentioned. Of these, palladium chloride is particularly preferable.

When a palladium complex and a phosphine compound are co-present, as the phosphine compound, triphenylphosphine, tri(o-tolyl)phosphine, tricyclohexylphosphine, tri-tert-butylphosphonium tetrafluoroborate, di-tert-butyl(methyl)phosphonium tetrafluoroborate, benzyl-di-1-adamantylphosphine, 1-(2-methoxyphenyl)-2-(di-tert-butylphosphino)-1H-pyrrole, 1-(2-methoxyphenyl)-2-(dicyclohexylphosphino)-1H-pyrrole, 1-phenyl-2-(dicyclohexylphosphino)-1H-pyrrole, 1-phenyl-2-(di-tert-butylphosphino)-1H-indole, 1-phenyl-2-(dicyclohexylphosphino)-1H-indole, 1-phenyl-2-(di-tert-butylphosphino)-1H-pyrrole, 1,2-bis(diphenylphosphino)ethane, 1,3-bis(diphenylphosphino)propane, 1,4-bis(diphenylphosphino)butane, 1,1'-bis(diphenylphosphino)ferrocene, 2-(dicyclohexylphosphino)biphenyl, sodium 2'-(dicyclohexylphosphino)-2,6-dimethoxybiphenyl-3-sulfonate, 2-(dicyclohexylphosphino)-2',6'-dimethoxybiphenyl, 2-(dicyclohexylphosphino)-2'-(N,N-dimethylamino)biphenyl, 2-(dicyclohexylphosphino)-2',6'-diisopropoxybiphenyl, 2-(dicyclohexylphosphino)-2'-methylbiphenyl, 2-(dicyclohexylphosphino)-2',4',6'-triisopropylbiphenyl, 2-(diphenylphosphino)-2'-(N,N-dimethylamino)biphenyl, 2,2'-bis(di-p-tolylphosphino)-1,1'-binaphthyl, 2,2'-bis[bis(3,5-dimethylphosphino)-1,1'-binaphthyl, 2,2'-bis(diphenylphosphino)-1,1'-binaphthyl, bis[2-(diphenylphosphino)phenyl]ether and the like can be mentioned. Of these, the above-mentioned 2-(dicyclohexylphosphino)biphenyl, sodium 2'-(dicyclohexylphosphino)-2,6-dimethoxybiphenyl-3-sulfonate, 2-(dicyclohexylphosphino)-2',6'-dimethoxybiphenyl, 2-(dicyclohexylphosphino)-2'-(N,N-dimethylamino)biphenyl, 2-(dicyclohexylphosphino)-2',6'-diisopropoxybiphenyl, 2-(dicyclohexylphosphino)-2'-methylbiphenyl, and 2,2'-bis(diphenylphosphino)-1,1'-binaphthyl are preferable.

The amount of the metal catalyst to be used is generally about 0.000001 to about 5 mol, preferably about 0.0001 to about 0.2 mol, per 1 mol of compound (XIII). When a metal catalyst unstable to oxygen is used for this reaction, the reaction is preferably performed in an inert gas (e.g., argon gas or nitrogen gas) stream.

The reaction temperature is generally -10-250° C., preferably 0-150° C., more preferably 40° C.-100° C. While the reaction time varies depending on the kind of the metal catalyst, base and solvent, reaction temperature and the like, it is generally 1 min-200 hr, preferably 30 min-100 hr, more preferably 1 hr-20 hr.

$R^4$ is preferably a formyl group.

When $R^4$ is a formyl group, compound (XI) can be produced by subjecting compound (XIV) to a reduction reaction.

A compound represented by the formula:

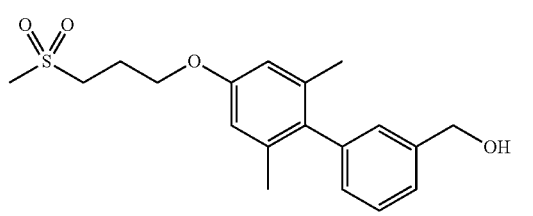

(XI)

wherein each symbol is as defined above,
or a salt thereof.

The reduction reaction is generally carried out using a reducing agent according to a conventional method. As the reducing agent, for example, metal hydrides such as aluminum hydride, diisobutylaluminum hydride, tributyltin hydride and the like; metal hydride complex compounds such as sodium cyanoborohydride, sodium triacetoxyborohydride, sodium borohydride, lithium aluminum hydride and the like; borane complexes such as borane tetrahydrofuran complex, borane dimethylsulfide complex and the like; alkyl boranes such as thexylborane, disiamylborane and the like; diborane; metals such as zinc, aluminum, tin, iron and the like; alkali metals such as sodium, lithium and the like/liquid ammonia (Birch reduction) and the like can be mentioned. Of these, the above-mentioned metal hydride complex compound is preferable.

The amount of the reducing agent to be used is appropriately determined according to the kind of the reducing agent. For example, the amount of the metal hydride, metal hydride complex compound, borane complex, alkyl boran or diborane to be used is generally about 0.1 to about 10 mol, preferably about 0.2 to about 5 mol, more preferably about 0.3 to about 3 mol, per 1 mol of compound (XIV). The amount of the metal (containing alkali metal used for Birch reduction) to be used is generally about 1 to about 20 mol, preferably about 1 to about 5 mol, per 1 mol of compound (XIV).

The reduction reaction is advantageously carried out using a solvent inert to the reaction. While the solvent is not particularly limited as long as the reaction proceeds, for example, alcohols such as methanol, ethanol, 1-propanol, 2-propanol, tert-butanol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid and the like; water, a mixed solvent thereof and the like are preferable. Of these, the above-mentioned alcohol is preferable. One or more kinds of these may be mixed at an appropriate ratio and used.

The amount of the solvent to be used for this reaction is 1- to 100-fold weight, preferably 2- to 50-fold weight, more preferably 3- to 20-fold weight, relative to compound (XIV).

The reaction temperature is generally −20-100° C., preferably 0-80° C., more preferably 10-40° C. While the reaction time varies depending on the reagent or solvent to be used, it is generally 1 min to 20 hr, preferably 10 min to 5 hr.

Compound (IX) wherein the leaving group Y is a halogen atom can be produced by reacting compound (XI) with a halogenating agent.

A compound represented by the formula:

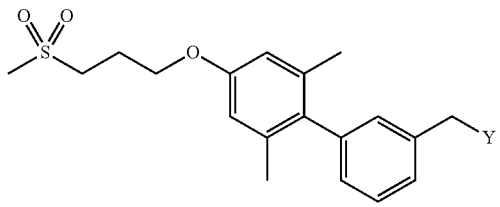

(IX)

wherein each symbol is as defined above,
or a salt thereof.

Examples of the halogenating agent include thionyl chloride, phosphorus oxychloride, phosphorus tribromide and the like.

The amount of the halogenating agent to be used is generally about 1 to about 10 mol, preferably about 1 to about 5 mol, more preferably about 1 to about 3 mol, per 1 mol of compound (XI).

The reaction of compound (XI) with a halogenating agent is carried out in a solvent inert to the reaction. Examples of the solvent inert to the reaction include halogenated hydrocarbons such as dichloromethane, chloroform, carbon tetrachloride and the like; aromatic hydrocarbons such as benzene, toluene, xylene and the like; ethers such as diethyl ether, diisopropyl ether, tert-butyl methyl ether, tetrahydrofuran, 1,4-dioxane, 1,2-dimethoxyethane and the like; esters such as methyl acetate, ethyl acetate, n-butyl acetate, tert-butyl acetate and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid and the like; and the like. Of these, the above-mentioned amide is preferable. One or more kinds of these may be mixed at an appropriate ratio and used. Alternatively, the halogenating agent may be used in an excess amount to replace a solvent.

The reaction temperature is generally −20-100° C., preferably 0-80° C., more preferably 10-40° C. While the reaction time varies depending on the reagent or solvent to be used, it is generally 1 min-20 hr, preferably 10 min-5 hr.

When the leaving group Y of compound (IX) is a methanesulfonyloxy group, a reagent such as methanesulfonyl chloride can be used; when it is a p-toluenesulfonyloxy group, a reagent such as p-toluenesulfonyl chloride can be used; and when it is a trifluoroacetoxy group, a reagent such as trifluoroacetic anhydride and the like can be used.

The reaction can be performed in the presence of a base.

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate, cesium carbonate and the like; alkali metal hydrogencarbonates such as sodium hydrogen carbonate and the like; alkali metal phosphates such as tripotassium phosphate and the like; acetates such as sodium acetate, ammonium acetate and the like; aromatic amines such as pyridine, lutidine and the like; tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like; alkali metal hydrides such as sodium hydride, potassium hydride and the like; metal amides such as sodium amide, lithium diisopropylamide, lithium hexamethyldisilazide and the like; alkali metal alkoxides having 1 to 6 carbon atoms such as sodium methoxide, sodium ethoxide, sodium tert-butoxide, potassium tert-butoxide and the like; organic lithiums such as methyllithium, n-butyllithium, sec-butyllithium, tert-butyllithium and the like, and the like can be mentioned. Of these, tertiary amines such as triethylamine and the like are preferable.

The amount of the reagent to be used is generally about 1 to about 10 mol, preferably about 1 to about 5 mol, more preferably about 1 to about 3 mol, per 1 mol of compound (XI).

The amount of the base to be used is generally about 1 to about 10 mol, preferably about 1 to about 5 mol, more preferably about 1 to about 3 mol, per 1 mol of compound (XI).

The reaction of compound (XI) and a reagent is performed in a solvent inert to the reaction. Examples of the solvent inert to the reaction include halogenated hydrocarbons such as dichloromethane, chloroform, carbon tetrachloride and the like; aromatic hydrocarbons such as benzene, toluene, xylene and the like; ethers such as diethyl ether, diisopropyl ether, tert-butyl methyl ether, tetrahydrofuran, 1,4-dioxane, 1,2-dimethoxyethane and the like; esters such as methyl acetate, ethyl acetate, n-butyl acetate, tert-butyl acetate and the like; amides such as N,N-dimethylformamide, N,N-dimethylacetamide, hexamethylphosphoramide and the like; organic acids such as formic acid, acetic acid, propionic acid, trifluoroacetic acid, methanesulfonic acid and the like; and the like. Of these, the above-mentioned ether is preferable. One or more kinds of these may be mixed at an appropriate ratio and used. An excess amount of a reagent may also be used as a solvent.

The reaction temperature is generally −20-100° C., preferably 0-80° C. While the reaction time varies depending on the reagent or solvent to be used, it is generally 1 min-20 hr, preferably 10 min-5 hr.

As shown in the following reaction scheme 4, compound (X) can be produced by reacting compound (IX) with compound (VIIIa).

$R^3$ is preferably a methoxy group, and Y is preferably a chlorine atom.

reaction scheme 4

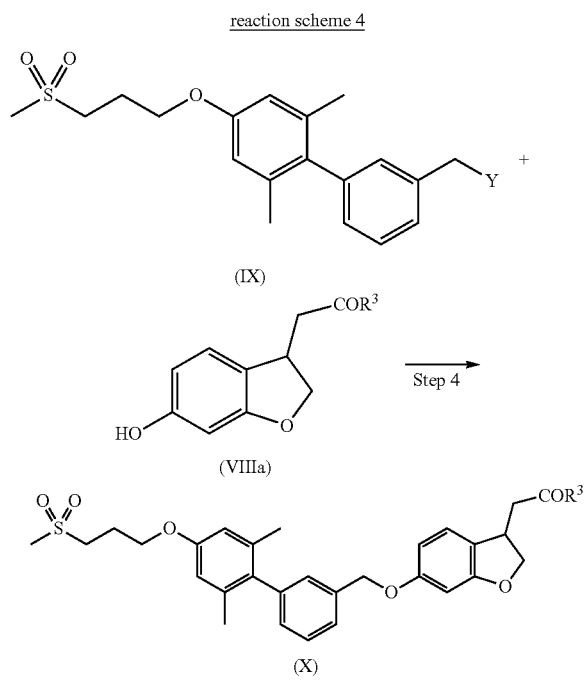

wherein each symbol is as defined above.

The reaction can be performed in the presence of a base.

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate, cesium carbonate and the like; alkali metal hydrogencarbonates such as sodium hydrogen carbonate and the like; alkali metal phosphates such as tripotassium phosphate and the like; acetates such as sodium acetate, ammonium acetate and the like; aromatic amines such as pyridine, lutidine and the like; tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like; alkali metal hydrides such as sodium hydride, potassium hydride and the like; metal amides such as sodium amide, lithium diisopropylamide, lithium hexamethyldisilazide and the like; alkali metal alkoxides having 1 to 6 carbon atoms such as sodium methoxide, sodium ethoxide, sodium tert-butoxide, potassium tert-butoxide and the like; organic lithiums such as methyllithium, n-butyllithium, sec-butyllithium, tert-butyllithium and the like, and the like can be mentioned. Of these, the above-mentioned alkali metal carbonate and alkali metal phosphate are preferable The amount of compound (VIIIa) to be used is generally about 0.2 to about 10 mol, preferably about 0.5 to about 3 mol, more preferably about 0.9 to about 2 mol, relative to compound (IX).

The amount of the base to be used is generally about 0.2 to about 10 mol, preferably about 0.5 to about 3 mol, more preferably about 1 to about 2 mol, per 1 mol of compound (XI).

The reaction is advantageously carried out using a solvent inert to the reaction. While the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; halogenated hydrocarbons such as dichloromethane, chloroform, carbon tetrachloride, 1,2-dichloroethane and the like; nitriles such as acetonitrile, propionitrile and the like; ketones such as acetone, ethyl methyl ketone and the like; sulfoxides such as dimethyl sulfoxide and the like. Of these, the above-mentioned ethers, amides and nitriles are preferable. One or more kinds of these may be mixed at an appropriate ratio and used.

The amount of the solvent to be used for this reaction is 1- to 100-fold weight, preferably 2- to 50-fold weight, relative to compound (IX).

The reaction temperature is generally 0-200° C., preferably 20-150° C., more preferably 40-80° C. While the reaction time varies depending on the reagent or solvent to be used, it is generally 30 min-20 hr, preferably 1 hr-5 hr.

When $R^3$ in the formula (X) is an optionally substituted $C_{1-6}$ alkoxy group, the compound is subjected to hydrolysis to convert to an optically active form of a compound represented by the formula:

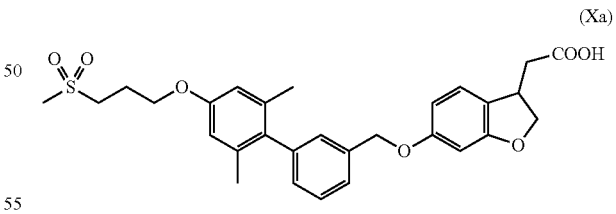

(hereinafter to be also referred to as compound (Xa)).

The hydrolysis is carried out using an acid or a base according to a conventional method, with preference given to a base.

As the acid, for example, mineral acids such as hydrochloric acid, sulfuric acid and the like; Lewis acids such as boron trichloride, boron tribromide and the like; organic acids such as trifluoroacetic acid, p-toluenesulfonic acid and the like, and the like can be mentioned. Lewis acid can be used concurrently with a thiol or a sulfide.

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate and the like; alkali metal alkoxides having 1 to 6 carbon atoms such as sodium methoxide, sodium ethoxide, potassium tert-butoxide and the like; organic bases (including hydrates) such as triethylamine, imidazole, formamidine and the like, and the like can be mentioned. Of these, the above-mentioned alkali metal hydroxide is preferable.

The amount of the acid or base to be used is generally about 0.5 to about 10 mol, preferably about 0.5 to about 6 mol, more preferably about 1 to about 2 mol, per 1 mol of compound (X).

The hydrolysis reaction is carried out without solvent, or using a solvent inert to the reaction. While the solvent is not particularly limited as long as the reaction proceeds, for example, alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, ethyl methyl ketone and the like; sulfoxides such as dimethyl sulfoxide and the like; water; and the like are used. Of these, the above-mentioned amides and sulfoxides are preferable. One or more kinds of these may be mixed at an appropriate ratio and used.

The reaction temperature is generally −10-200° C., preferably 0-120° C., more preferably 40-100° C. The reaction time is generally 10 min-100 hr, preferably 10 min-24 hr, more preferably 30 min-10 hr.

Compound (Xa) can be purified according to a conventional method. As the purification method, chromatography, suspending by stirring, recrystallization and the like can be mentioned, and recrystallization is particularly preferable.

The purification is generally performed in a solvent. While the solvent is not particularly limited, for example, alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, ethyl methyl ketone and the like; sulfoxides such as dimethyl sulfoxide and the like; and water are used. These solvents may be used in a mixture at an appropriate ratio. As a mixed solvent, ethanol-water and acetone-water are particularly preferable.

The crystal of compound (Xa) obtained by recrystallization can be obtained as a hydrate crystal by solid-liquid separation, followed by vacuum drying performed at a low vacuum (not less than 1.5 KPa) at low temperature (not more than 40° C.) or ventilation drying with a gas containing water.

As shown in the following reaction scheme 5, compound (X) can also be produced by subjecting compound (XV) to an asymmetric reduction.

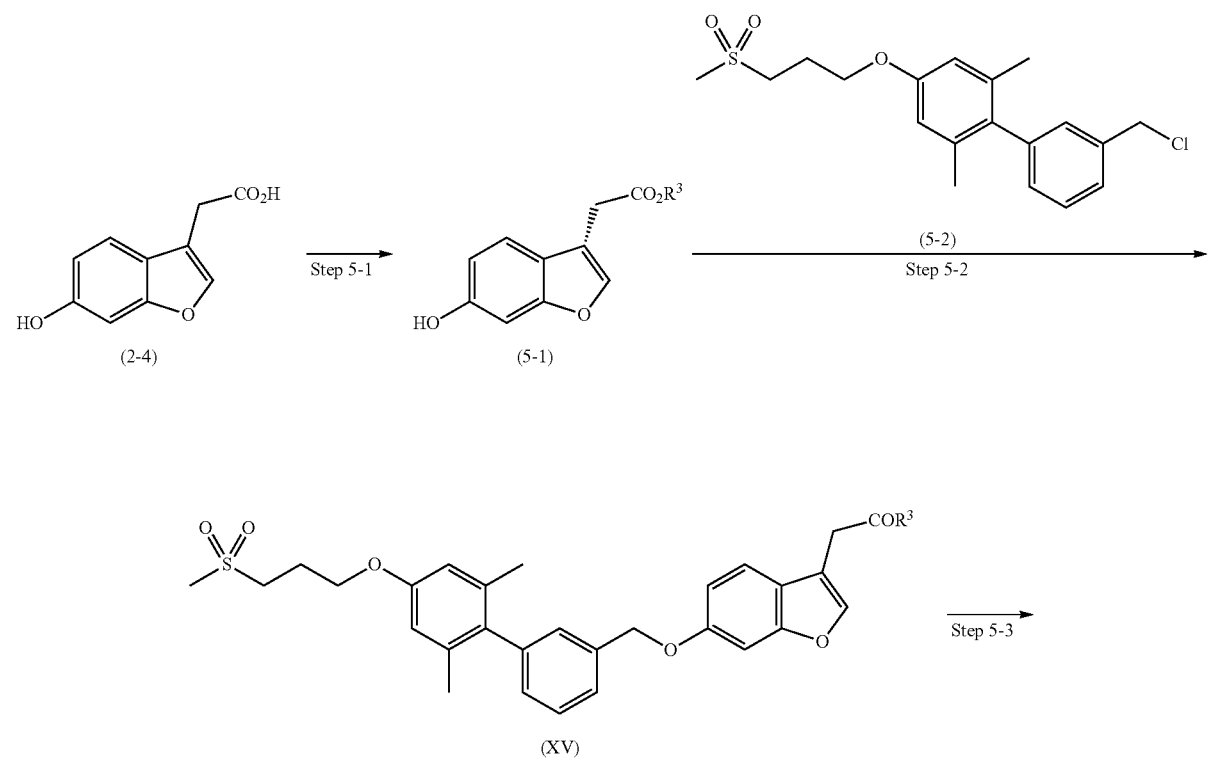

-continued

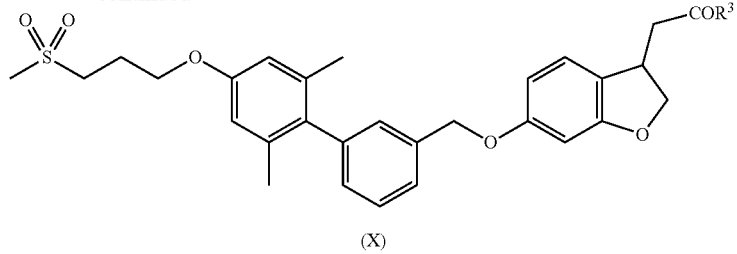

(X)

wherein each symbol is as defined above.

<Step 5-1>

Compound (2-4) is esterified to convert to compound (5-1). The esterification reaction can be performed by a method similar to the aforementioned step 2-5.

<Step 5-2> compound (XV) can be produced by reacting compound (5-1) with compound (5-2) in the presence of a base. The reaction can be performed by a method similar to the aforementioned step 4.

<Step 5-3>

Optically active compound (X) can be produced by subjecting compound (XV) to an asymmetric hydrogenation reaction.

The asymmetric hydrogenation reaction is desirably performed in the presence of a transition metal complex.

As the transition metal complex, rhodium complex, ruthenium complex, iridium complex, palladium complex and the like can be mentioned. Of these, the ruthenium complex is most preferable. As the ruthenium complex, those similar to the ruthenium complex used for step 1 can be used.

As the optically active diphosphine ligand in the above-mentioned ruthenium complex, those similar to the diphosphine ligand used in step 1 can be used. As the optically active diphosphine ligand, 1-[2-(2-substituted phosphino)ferrocenyl]ethyl-2-substituted phosphine (Josiphos) and substituted-1,2-bisphosphoranobenzene (DuPHOS) and the like are preferable.

A ruthenium complex produced from an optically active diphosphine and a ruthenium complex to be a metal source by a known means, and isolated or purified by a known means (e.g., concentration, solvent extraction, fractionation, crystallization, recrystallization, chromatography) can be used.

In addition, a ruthenium complex can also be prepared by adding optically active diphosphine and a ruthenium complex to be a metal source to the reaction system.

While the amount of the ruthenium complex to be used varies depending on the reaction container, form of reaction and the like, it is, for example, about 0.1-about 0.00001 mol per 1 mol of compound (XV).

As the base to be used for this reaction, an inorganic base or an organic base can be used.

Examples of the inorganic base include alkali metal hydroxides such as lithium hydroxide, potassium hydroxide, sodium hydroxide, cesium hydroxide and the like; alkali metal alkoxides having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxides having 1 to 6 carbon atoms such as sodium thiomethoxide and the like; carbonates such as sodium carbonate, potassium carbonate, cesium carbonate and the like; hydrogencarbonates such as sodium hydrogen carbonate, potassium hydrogen carbonate and the like; acetates such as sodium acetate, potassium acetate and the like; phosphates such as tripotassium phosphate, sodium phosphate and the like; monohydrogen phosphates such as potassium monohydrogen phosphate, sodium monohydrogen phosphate and the like; and the like.

Examples of the organic base include tertiary aliphatic amines such as trimethylamine, triethylamine, N-methylmorpholine, N,N-diisopropylethylamine, diethylamine, diisopropylamine, cyclohexylamine, ethylenediamine and the like; aromatic amines such as pyridine, picoline, N,N-dimethylaniline and the like; and the like.

The amount of the base to be used is about 0.01 to about 100 mol, preferably about 0.1 to about 10 mol, per 1 mol of compound (XV).

This reaction is generally carried out in a solvent. While the solvent is not particularly limited as long as it is inert to the reaction and can solubilize the starting compound and the catalyst, for example, aromatic hydrocarbons such as toluene, xylene and the like; aliphatic hydrocarbons such as heptane, hexane and the like; halogenated hydrocarbons such as methylene chloride and the like; ethers such as diethyl ether, tetrahydrofuran and the like; alcohols such as methanol, ethanol, 2-propanol, butanol, benzyl alcohol and the like; nitriles such as acetonitrile and the like; amides such as N,N-dimethylformamide and the like; sulfoxides such as dimethyl sulfoxide and the like, and the like can be used. These solvents may be used in a mixture at an appropriate ratio. The solvent is preferably alcohol.

The above-mentioned solvents are preferably used for the reaction after drying and deaeration.

The amount of the solvent to be used is appropriately determined according to the solubility of compound (XV) and the like. For example, the reaction proceeds in a condition ranging from a near solventless system to a system wherein not less than 100-fold weight of the solvent is used relative to compound (XV). Generally, the solvent is preferably used in about 2- to about 50-fold weight relative to compound (XV).

The hydrogenation can be carried out by any of a batch reaction and a continuous reaction. In addition, the hydrogenation is carried out in the presence of hydrogen, where the hydrogen pressure is for example, 0.01 to 200 atm, preferably 1 to 15 atm.

The reaction temperature is generally −30° C. to 100° C., preferably 0° C. to 80° C. The reaction time is generally 0.1 to 72 hr, preferably 1 to 48 hr.

As shown in the following reaction scheme 6, compound (X) can also be produced by reacting compound (XI) with compound (VIIIb).

reaction scheme 6

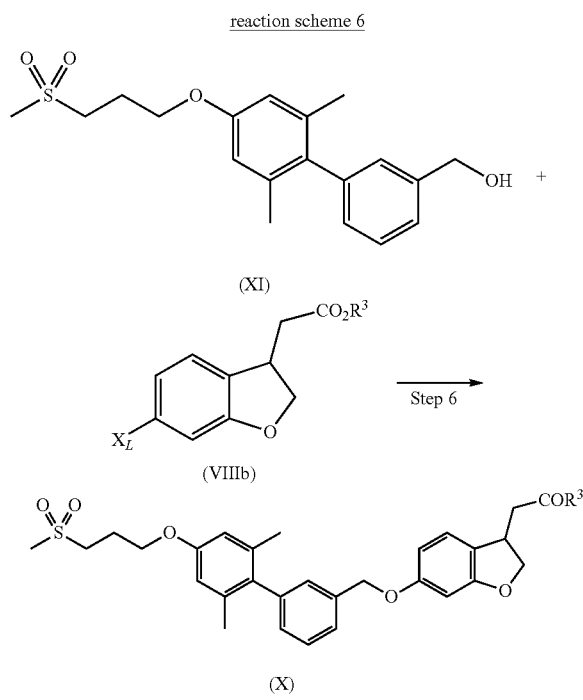

wherein $X_L$ is a leaving group, and other symbols are as defined above.

As the leaving group for $X_L$, those similar to the leaving group for $X^1$ can be mentioned, and an optionally halogenated $C_{1-6}$ alkylsulfonyloxy group (e.g., methanesulfonyloxy, ethanesulfonyloxy, trichloromethanesulfonyloxy, trifluoromethanesulfonyloxy) is preferable, and trifluoromethanesulfonyloxy is particularly preferable.

Compound (VIIIb) wherein $X_L$ is trifluoromethanesulfonyloxy can be produced by reacting compound (VIIIa) with trifluoromethanesulfonic anhydride.

The reaction of compound (XI) and compound (VIIIb) can be performed in the presence of a base.

As the base, for example, alkali metal hydroxides such as lithium hydroxide, sodium hydroxide, potassium hydroxide and the like; alkaline earth metal hydroxides such as barium hydroxide and the like; alkali metal carbonates such as sodium carbonate, potassium carbonate, cesium carbonate and the like; alkali metal hydrogencarbonates such as sodium hydrogen carbonate and the like; alkali metal phosphates such as tripotassium phosphate and the like; acetates such as sodium acetate, ammonium acetate and the like; aromatic amines such as pyridine, lutidine and the like; tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like; alkali metal hydrides such as sodium hydride, potassium hydride and the like; metal amides such as sodium amide, lithium diisopropylamide, lithium hexamethyldisilazide and the like; alkali metal alkoxides having 1 to 6 carbon atoms such as sodium methoxide, sodium ethoxide, sodium tert-butoxide, potassium tert-butoxide and the like; organic lithiums such as methyllithium, n-butyllithium, sec-butyllithium, tert-butyllithium and the like, and the like can be mentioned. Of these, the above-mentioned alkali metal hydroxide, alkali metal carbonate and alkali metal phosphate and the like are particularly preferable.

The amount of compound (VIIIb) to be used is generally about 0.2 to about 10 mol, preferably about 0.5 to about 3 mol, more preferably about 0.9 to about 2 mol, relative to compound (XI).

The amount of the base to be used is generally about 0.2 to about 10 mol, preferably about 0.5 to about 3 mol, more preferably about 1 to about 2 mol, per 1 mol of compound (XI).

The reaction is advantageously carried out using a solvent inert to the reaction. While the solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; halogenated hydrocarbons such as dichloromethane, chloroform, carbon tetrachloride, 1,2-dichloroethane and the like; nitriles such as acetonitrile, propionitrile and the like; ketones such as acetone, ethyl methyl ketone and the like; sulfoxides such as dimethyl sulfoxide and the like; and the like are used. Of these, the above-mentioned ethers, amides and nitriles are preferable. One or more kinds of these may be mixed at an appropriate ratio and used.

The amount of the solvent to be used for this reaction is 1- to 100-fold weight, preferably 2- to 50-fold weight, relative to compound (XI).

The reaction temperature is generally 0-200° C., preferably 20-150° C., more preferably 40-80° C. While the reaction time varies depending on the reagent or solvent to be used, it is generally 30 min-20 hr, preferably 1 hr-5 hr.

In each of the aforementioned reactions, when the starting compound has an amino group, a carboxy group, a hydroxy group, a carbonyl group or a mercapto group as a substituent, a protecting group generally used in the peptide chemistry and the like may be introduced into these groups, and the object compound can be obtained by eliminating the protecting group as necessary after the reaction.

Examples of the amino-protecting group include a formyl group; a $C_{1-6}$ alkyl-carbonyl group, a $C_{1-6}$ alkoxy-carbonyl group, a benzoyl group, a $C_{7-13}$ aralkyl-carbonyl group (e.g., benzylcarbonyl), a $C_{7-13}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-11}$ aralkyl group (e.g., benzyl), a phenyl group, a trityl, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-13}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), and the like. These groups are optionally substituted by 1 to 3 substituents selected from a halogen atom, a $C_{1-6}$ alkyl group, a $C_{1-6}$ alkoxy group and a nitro group.

Examples of the carbonyl-protecting group include a cyclic acetal (e.g., 1,3-dioxane), a non-cyclic acetal (e.g., a di-$C_{1-6}$ alkylacetal) and the like.

Examples of the mercapto-protecting group include a $C_{1-6}$ alkyl group, a phenyl group, a trityl group, a $C_{7-13}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The above-mentioned protecting groups can be removed by a method known per se, for example, the method described in Protective Groups in Organic Synthesis, John Wiley and Sons (1980) and the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like can be mentioned.

The compounds of the formulas (II), (VI), (VIIa), (VIIb), (IX), (X), (XIII) and (XIV) and salts thereof obtained by each of the above-mentioned production methods can be isolated and purified by a known means such as concentration, concentration under reduced pressure, solvent extraction, crystallization, recrystallization, phase transfer, chromatography and the like. In addition, the starting compounds used for each of the above-mentioned production methods can be isolated and purified by a known means similar to the aforementioned methods. These starting compounds may be used in the form of a reaction mixture without isolation, as a starting material for the next step.

An optically active form of a compound represented by the formula (II), (III), (IVa1), (IVb1), (IVa), (IVb), (VI), (VIIa), (VIIb), (VIII), (VIIIa), (VIIIb) or (X) or a salt thereof in the present invention only need to be an optically active compound or a salt thereof. It is preferably not less than 80% ee, more preferably not less than 90% ee, still more preferably not less than 95% ee, and most preferably not less than 98% ee.

The present invention also relates to a crystal of [(3S)-6-({2',6'-dimethyl-4'-[3-(methylsulfonyl)propoxy]biphenyl-3-yl}methoxy)-2,3-dihydro-1-benzofuran-3-yl]acetic acid (hereinafter to be also referred to as the crystal of the present invention), which shows a powder X-ray diffraction pattern having characteristic peaks at lattice spacing (d) of about 19.24±0.2, 18.79±0.2, 6.35±0.2, 5.37±0.2, 4.91±0.2 and 4.83±0.2 angstroms by powder X-ray diffraction.

The crystal of the present invention can be obtained by drying [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate crystal or preserving said crystal at a high temperature for a predetermined period. For example, it can be obtained by preserving [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate crystal at 20% RH or below for 2 to 3 hr or heating at 50-65° C. for 30 min-2 hr.

As an analysis method of the obtained crystal, a crystal analysis method by X ray diffraction is generally used. As a method for determining the crystal orientation, a mechanical method or an optical method (e.g., FT-Raman spectrum, solid-state NMR spectrum) and the like can also be used.

The spectrum peaks obtained by the above-mentioned analysis method inevitably contain a given measurement error in the properties. The numerical values of the spectrum peaks, which are within such error range, are also encompassed in the crystal of the present invention. For example, "±0.2" in the lattice spacing (d) of powder X-ray diffraction means that the error is acceptable.

The crystal of the present invention is preferably a crystal of [(3S)-6-({2',6'-dimethyl-4'-[3-(methylsulfonyl)propoxy]biphenyl-3-yl}methoxy)-2,3-dihydro-1-benzofuran-3-yl] acetic acid, which shows a powder X-ray diffraction pattern having characteristic peaks at lattice spacing (d) of about 19.24±0.2, 18.79±0.2, 6.35±0.2, 5.37±0.2, 4.91±0.2, 4.83±0.2, 4.49±0.2, 3.84±0.2 and 3.74±0.2 angstroms by powder X-ray diffraction, more preferably, a crystal of [(3S)-6-({2',6'-dimethyl-4'-[3-(methylsulfonyl)propoxy]biphenyl-3-yl}methoxy)-2,3-dihydro-1-benzofuran-3-yl]acetic acid, which shows a powder X-ray diffraction pattern having characteristic peaks at lattice spacing (d) of about 19.24±0.2, 18.79±0.2, 6.35±0.2, 5.37±0.2, 4.91±0.2, 4.83±0.2, 4.56±0.2, 4.49±0.2, 4.12±0.2, 3.84±0.2, 3.80±0.2 and 3.74±0.2 angstroms by powder X-ray diffraction, still more preferably, a crystal of [(3S)-6-({2',6'-dimethyl-4'-[3-(methylsulfonyl)propoxy]biphenyl-3-yl}methoxy)-2,3-dihydro-1-benzofuran-3-yl]acetic acid, which shows the peaks shown in the below-mentioned Table 1.

Compound (X) may be a crystal, and the crystal form may be single or a mixture of crystal forms. The crystal can be produced by a crystallization method known per se.

Compound (X) may be labeled with an isotope (e.g., $^3H$, $^{13}C$, $^{14}C$, $^{18}F$, $^{35}S$, $^{125}I$) and the like.

Compound (X) may be a solvate or a non-solvate, or anhydride or hydrate.

Moreover, a deuterium converter wherein $^1H$ has been converted to $^2H(D)$ is also encompassed in compound (X).

Compound (X) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Since compound (X), a salt thereof and a prodrug thereof (hereinafter, these are collectively abbreviated as the compound of the present invention) have a GPR40 receptor function modulating action, particularly, a GPR40 receptor agonist activity, and high dissolution property, and are low in toxicity (e.g., influence on hematological parameters such as red blood cell number, hamatocrit value, hemoglobin concentration, MCH, MCHC, MCV, platelet count, leukocyte count, blood reticulocyte count, leukocyte classification and the like; blood biochemical parameters such as total protein, albumin, A/G ratio, glucose, total cholesterol, triglyceride, urea nitrogen, creatinine, total bilirubin, AST, ALT, LDH, ALP, CK, Na, K, Cl, calcium, inorganic phosphorus, retinol (vitamin A) and the like) and a fewer side effects (e.g., acute toxicity, chronic toxicity, genetic toxicity, reproductive toxicity, cardiotoxicity, drug interaction (CYP inhibitory action), carcinogenicity), they are useful as safe GPR40 receptor function modulators, preferably GPR40 agonists.

A prodrug of the compound (X) means a compound which is converted to the compound (X) with a reaction due to an enzyme, an gastric acid, etc. under the physiological condition in the living body, that is, a compound which is converted to the compound (X) with enzymatic oxidation, reduction, hydrolysis and the like; a compound which is converted to the compound (X) by hydrolysis and the like due to gastric acid and the like.

A prodrug of the compound (X) may be a compound obtained by subjecting an amino group in the compound (X) to an acylation, alkylation or phosphorylation (e.g., a compound obtained by subjecting an amino group in the compound (X) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in the compound (X) to an acylation, alkylation, phosphorylation or boration (e.g., a compound obtained by subjecting an hydroxy group in the compound (X) to an acetylation, palmitoylation, propanoylation, pivaloylation, succinylation, fumarylation, alanylation or dimethylaminomethylcarbonylation); a compound obtained by subjecting a carboxy group in the compound (X) to an esterification or amidation (e.g., a compound obtained by subjecting a carboxy group in the compound (X) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. These compounds can be produced from the compound (X) according to a method known per se.

The compound of the present invention shows a superior GPR40 receptor function modulating action in mammals (e.g., mouse, rat, hamster, rabbit, cat, dog, bovine, sheep, monkey, human), and is useful as modulators of physiological function in which GPR40 receptor is involved or as agents for the prophylaxis or treatment of pathology or disease in which GPR40 receptor is involved.

To be specific, the compound of the present invention is useful as insulin secretion modulators (preferably insulin secretagogues), hypoglycemic agents and pancreatic B cell protectors.

Particularly, the compound of the present invention is useful as blood glucose level-dependent insulin secretagogues based on the GPR40 receptor agonist activity thereof. That is different from sulfonylureas, the compound of the present invention is useful as insulin secretagogues that do not cause hypoglycemia.

Moreover, the compound of the present invention is useful as agents for the prophylaxis or treatment of diseases such as diabetes, impaired glucose tolerance, ketosis, acidosis, diabetic complications (e.g., diabetic neuropathy, diabetic nephropathy, diabetic retinopathy, macroangiopathy, diabetic gangrene), macular edema, hyperlipidemia, genital disorder, skin disease, arthropathy, osteopenia, arteriosclerosis, thrombotic disease, dyspepsia, memory and learning disorder, depression, depression and mania, schizophrenia, attention deficit hyperactivity disorder, visual disorder, appestat disorder (e.g., hyperorexia), obesity, hypoglycemia, hypertension, edema, insulin resistance, unstable diabetes, fatty atrophy, insulin allergy, insulinoma, lipotoxicity, hyperinsulinemia, cancers (e.g., breast cancer), metabolic syndrome, immune diseases (e.g., immunodeficiency), inflammatory disease (e.g., enteritis, arthritis, allergy), multiple sclerosis, acute kidney failure and the like. Here, diabetes includes type I diabetes, type II diabetes, gestational diabetes and obese diabetes. In addition, hyperlipidemia includes hypertriglyceridemia, hypercholesterolemia, hypo-high-density-lipoproteinemia, postprandial hyperlipidemia and the like.

For diagnostic criteria of diabetes, Japan Diabetes Society reported diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported diagnostic criteria of diabetes.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports by ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a fasting blood glucose level (glucose concentration of intravenous plasma) of not less than 110 mg/dl and less than 126 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention is also useful as a therapeutic agent for diabetes with sulfonylurea secondary failure and affords a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic B cell in the same manner as a sulfonylurea compound, though it does not have a sulfonylurea skeleton, such as glinide compounds (e.g., repaglinide, senaglinide, nateglinide, mitiglinide or a calcium salt hydrate thereof etc.), and the like, can be mentioned.

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The content of the compound of the present invention in a pharmaceutical preparation is about 0.01 to about 100% by weight relative to the whole preparation. While the dose varies depending on the administration subject, administration route, diseases, condition and the like, for example, the compound of the present invention (as an active ingredient) can be orally administered to a patient with diabetes (body weight about 60 kg) in about 0.01 to about 30 mg/kg body weight per day, preferably about 0.1 to about 20 mg/kg body weight per day, more preferably about 1 to about 20 mg/kg body weight per day, which may be given at once or in several portions (e.g., 1-3 portions) a day.

As the above-mentioned pharmacologically acceptable carrier, various organic or inorganic carrier substances conventionally used as a preparation material can be mentioned. For example, excipient, lubricant, binder and disintegrant for solid preparations; solvent, solubilizing agents, suspending agent, isotonicity agent, buffer and soothing agent for liquid preparations and the like can be mentioned. Where necessary, conventional additives such as preservatives, antioxidants, colorants, sweetening agents, adsorbing agents, wetting agents and the like can be used.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propylene glycol, macrogol, sesame oil, corn oil, olive oil and the like can be mentioned.

As the solubilizing agents, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl amino-propionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As the isotonicity agent, for example, glucose, D-sorbitol, sodium chloride, glycerin, D-mannitol and the like can be mentioned.

As the buffer, for example, buffers such as phosphates, acetates, carbonates, citrates and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfites, ascorbic acid, α-tocopherol and the like can be mentioned.

As the colorant, for example, water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment and the like), natural pigments (e.g., β-carotene, chlorophil, ferric oxide red etc.) and the like can be mentioned.

As the sweetening agent, for example, saccharin sodium, dipotassium glycyrrhizinate, aspartame, stevia and the like can be mentioned.

Moreover, the compound of the present invention can be used in combination with drugs other than the compound of the present invention.

As the drugs that can be used in combination with the compound of the present invention (preferably, [(3S)-6-({2', 6'-dimethyl-4'-[3-(methylsulfonyl)propoxy]biphenyl-3-yl}methoxy)-2,3-dihydro-1-benzofuran-3-yl]acetic acid 0.5 hydrate) (hereinafter sometimes to be abbreviated as a concomitant drug), for example, other therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antiinflammatory agents, antithrombotic agents, therapeutic agents for osteoporosis, vitamins, antidementia agents, therapeutic agents for pollakiuria or urinary incontinence, therapeutic agents for dysuria and the like can be mentioned. Specifically, the following agents can be mentioned.

Examples of other therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compounds described in WO2007/013694, WO2007/018314, WO2008/093639 and WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl-peptidase IV inhibitors (e.g., Alogliptin or a salt thereof (preferably benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compounds described in WO2004/041266, WO2004/106276, WO2005/063729, WO2005/063725, WO2005/087710, WO2005/095338, WO2007/013689 and WO2008/001931), GLP-1 receptor agonists (e.g., GLP-1, GLP-1MR agent, Liraglutide, Exenatide, AVE-0010, BIM-51077, Aib (8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitor, 11β-hydroxysteroid dehydrogenase inhibitors (e.g., BVT-3498, INCB-13739), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, compounds described in WO2006/112549, WO2007/028135, WO2008/047821, WO2008/050821, WO2008/136428 and WO2008/156757), GIP (Glucose-dependent insulinotropic peptide), GPR119 agonists (e.g., PSN821, MBX-2982, APD597), FGF21, FGF analogue and the like.

Examples of the therapeutic agents for diabetic complications include aldose reductase inhibitors (e.g., Tolrestat, Epalrestat, Zopolrestat, Fidarestat, CT-112, ranirestat (AS-3201), Lidorestat), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2 methylphenoxy) propyl]oxazole), compound described in WO2004/039365), PKC inhibitors (e.g., ruboxistaurin mesylate), AGE inhibitors (e.g., ALT-946, N-phenacylthiazolium bromide (ALT-766), EXO-226, Pyridorin, Pyridoxamine), GABA receptor agonists (e.g., gabapentin, Pregabalin), serotonin-noradrenaline reuptake inhibitors (e.g., duloxetine), sodium channel inhibitors (e.g., Lacosamide), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agent for hyperlipidemia include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, gamma oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril and the like), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil and the like), calcium antagonists (e.g., manidipine, nifedipine, amlodipine, efonidipine, nicardipine, amlodipine, cilnidipine and the like), β blockers (e.g., metoprolol, atenolol, propranolol, carvedilol, pindolol and the like), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using *Escherichia coli* or yeast; fragments or derivatives of FGF21)), anorexigenic agents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antiinflammatory agents include non-steroidal antiinflammatory agents such as aspirin, acetaminophen, indomethacin and the like.

Examples of the antithrombotic agents include heparin (e.g., heparin sodium, heparin calcium, enoxaparin sodium, dalteparin sodium), warfarins (e.g., warfarin potassium), anti-thrombin drugs (e.g., aragatroban, dabigatran)), FXa inhibitors (e.g., rivaroxaban, apixaban, edoxaban, YM150, compounds described in WO02/06234, WO2004/048363, WO2005/030740, WO2005/058823 and WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium, risedronate disodium and the like.

Examples of the vitamins include vitamin $B_1$, vitamin $B_{12}$ and the like.

Examples of the antidementia agents include tacrine, donepezil, rivastigmine, galanthamine and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

Furthermore, glycosylation inhibitors (e.g., ALT-711), nerve regeneration promoting drugs (e.g., Y-128, VX853, prosaptide), antidepressants (e.g., desipramine, amitriptyline, imipramine), antiepileptics (e.g., lamotrigine, Trileptal, Keppra, Zonegran, Pregabalin, Harkoseride, carbamazepine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR agent), $\alpha_2$ receptor agonists (e.g., clonidine), local analgesics (e.g., capsaicin), antianxiety drugs (e.g., benzothiazepines), phosphodiesterase inhibitors (e.g., sildenafil), dopamine receptor agonists (e.g., apomorphine), midazolam, Ketoconazole and the like can be also used in combination with the compound of the present invention.

The concomitant drug is preferably an insulin preparation, a PPAR function modulator (preferably pioglitazone or its hydrochloride), an α-glucosidase inhibitor (preferably voglibose), a biguanide (preferably metformin or hydrochloride thereof), a sulfonylurea (preferably glibenclamide, glimepiride), mitiglinide or calcium salt hydrate thereof, nateglinide, a dipeptidyl peptidase IV inhibitor (preferably alogliptin or benzoate thereof, 2-[[6-[(3R)-3-amino-1-piperidinyl]-3,4-dihydro-3-methyl-2,4-dioxo-1(2H)-pyrimidinyl]methyl]-4-fluorobenzonitrile or succinate thereof, 2-[2-(3-(R)-amino-piperidin-1-yl)-5-fluoro-6-oxo-6H-pyrimidin-1-ylmethyl]-benzonitrile or tartarate thereof) and the like.

Particularly Preferred Include (1) combined use of [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate and insulin preparation;

(2) combined use of [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate and pioglitazone or hydrochloride thereof;

(3) combined use of [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate and α-glucosidase inhibitor (preferably, voglibose);

(4) combined use of [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate and biguanide (preferably metformin or hydrochloride thereof);

(5) combined use of [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate and sulfonylurea (preferably, glibenclamide, glimepiride);

(6) combined use of [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate and mitiglinide or calcium salt hydrate thereof or nateglinide;

(7) combined use of [(3S)-6-({2',6'-dimethyl-4'-[3-(methylsulfonyl)propoxy]biphenyl-3-yl}methoxy)-2,3-dihydro-1-benzofuran-3-yl]acetic acid 0.5 hydrate and dipeptidyl peptidase IV inhibitor (preferably, alogliptin or benzoate thereof, 2-[[6-[(3R)-3-amino-1-piperidinyl]-3,4-dihydro-3-methyl-2,4-dioxo-1(2H)-pyrimidinyl]methyl]-4-fluorobenzonitrile or succinate thereof, 2-[2-(3-(R)-amino-piperidin-1-yl)-5-fluoro-6-oxo-6H-pyrimidin-1-ylmethyl]-benzonitrile or tartrate thereof);

and the like.

By combining the compound of the present invention with a concomitant drug, superior effects such as (1) decreased dose of the compound of the present invention or a concomitant drug as compared to single administration of the compound of the present invention or a concomitant drug, (2) possible setting of a long treatment period by selecting a concomitant drug having different action and mechanism from those of the compound of the present invention, (3) possible designing of a sustained treatment effect by selecting a concomitant drug having different action and mechanism from those of the compound of the present invention, (4) a synergistic effect afforded by a combined use of the compound of the present invention and a concomitant drug, and the like can be achieved.

When the compound of the present invention and a concomitant drug are used in combination, the administration time of the compound of the present invention and the concomitant drug is not restricted, and the compound of the present invention and the concomitant drug may be administered simultaneously, or may be administered at staggered times, to an administration subject. The dosage of the concomitant drug may be determined according to the dose clinically used, and can be appropriately selected depending on an administration subject, administration route, disease, combination and the like.

As the administration mode of the compound of the present invention and the concomitant drug, the following methods can be mentioned: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (e.g., the compound of the present invention and the concomitant drug are administered in this order, or in the reverse order), and the like.

EXAMPLES

The present invention is further explained in detail by referring to the following Reference Examples and Examples which are mere working examples not to be construed as limitative and may be changed without departing from the scope of the present invention.

The term "room temperature" in the following Reference Examples and Examples indicates the range of generally from about 10° C. to about 35° C. The chemical yield is an isolation yield (mol/mol %) or was obtained by high performance liquid chromatography. The optical purity (asymmetric yield) of optically active forms was evaluated according to enantiomeric excess (% e.e.). The enantiomeric excess was determined by the following the formula:

enantiomeric excess (% e.e.)=100×[(R)−(S)]/[(R)+(S)]
or 100×[(S)−(R)]/[(R)+(S)]

wherein (R) and (S) are each an area of each enantiomer in high performance liquid chromatography.

The solvent used for chromatography is in % by volume and other "%" is in % by weight.

OH proton, NH proton etc. that could not be confirmed due to broad peak by proton NMR spectrum are not included in the data.

The other symbols used herein mean the following:
s: singlet
d: doublet
t: triplet
q: quartet
m: multiplet
br: broad
J: coupling constant
Hz: Hertz
CDCl$_3$: deuterated chloroform
DMSO-d$_6$: deuterated dimethyl sulfoxide
CD$_3$OD: deuterated methanol
$^1$H NMR: proton nuclear magnetic resonance
$^{13}$C NMR: $^{13}$C nuclear magnetic resonance
$^{31}$P NMR: $^{31}$P nuclear magnetic resonance
RuCl$_2$[(R)-iPr-duphos](dmf)$_n$: dichloro[(+)-1,2-bis((2R,5R)-2,5-diisopropylphosphorano)benzene]ruthenium (II)-N,N-dimethylformamide complex In the following Reference Examples and Examples, nuclear magnetic resonance spectrum (NMR) was measured under the following conditions.

$^1$H nuclear magnetic resonance spectrum ($^1$H NMR): DPX300 (300 MHz) manufactured by Bruker or BRUKER AVANCE 500 (500 MHz) manufactured by Bruker, internal standard substance: tetramethylsilane $^{13}$C nuclear magnetic resonance spectrum ($^{13}$C NMR): DPX300 (300 MHz) manufactured by Bruker or BRUKER AVANCE 500 (500 MHz) manufactured by Bruker, internal standard substance: CDCl$_3$ or CD$_2$Cl$_2$ $^{31}$P nuclear magnetic resonance spectrum ($^{31}$P NMR): DPX300 (300 MHz) manufactured by Bruker or BRUKER AVANCE 500 (500 MHz) manufactured by Bruker, external standard substance: 85% H$_3$PO$_4$ aqueous solution powder X-ray diffraction was measured under the following conditions by using RINT ULTIMA IV (Rigaku Corporation).

Scan speed: 6°/min, scan range: 2°-35°, tube voltage: 40 kV, tube current: 50 mA Reference Example 1

Synthesis of 4-(chloromethyl)-7-hydroxy-2H-chromen-2-one

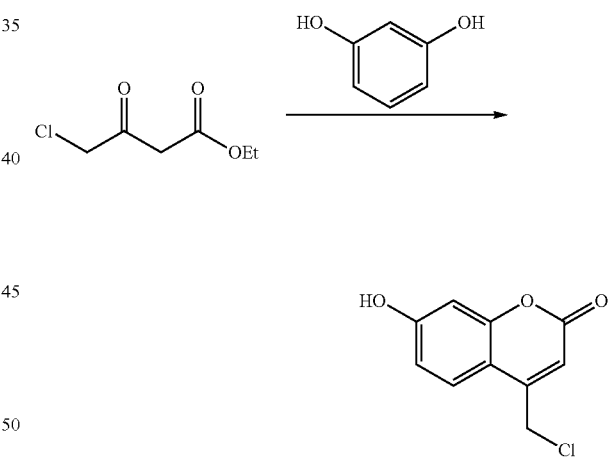

Resorcinol (275 g) was dissolved in acetic acid (560 mL) at 50° C. to prepare a solution. Separately, ethyl 4-chloroacetoacetate (205 g) was dissolved in acetic acid (187 ml), and concentrated sulfuric acid (100 mL) was added at 8° C. The solution was added at 8° C. to the resorcinol solution prepared in advance, and the mixture was stirred at 25° C. for 1 hr and at 60° C. for 3 hr. Warm water (3.24 L) was added at 40° C., and the mixture was stirred at 25° C. for 2 hr. The precipitated solid was collected by filtration. The solid was washed with water and air-dried to give the title compound (255 g) as a yellow solid.

$^1$H NMR (500 MHz, DMSO-d$_6$): δ 4.88-4.99 (m, 2H), 6.42 (s, 1H), 6.75 (d, 1H, J=2.2 Hz), 6.84 (dd, 1H, J=8.5, 2.2 Hz), 7.67 (d, 1H, J=8.5 Hz), 10.67 (s, 1H).

Reference Example 2

Synthesis of (6-hydroxy-1-benzofuran-3-yl)acetic acid (1R)-1-phenylethylamine salt

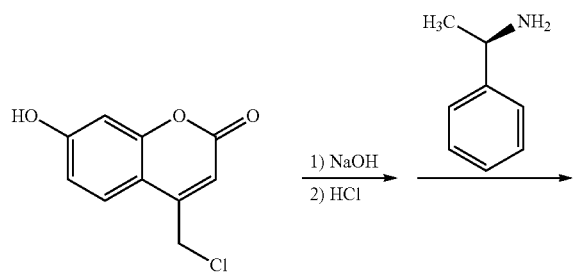

Sodium hydroxide (135 g) was dissolved in water (830 mL) to prepare a 14% aqueous sodium hydroxide solution. To a solution (623 mL) of 4-(chloromethyl)-7-hydroxy-2H-chromen-2-one (254 g) in water was added the above-mentioned 14% aqueous sodium hydroxide solution at 5° C., and the mixture was stirred at 25° C. for 1 hr and at 60° C. for 4 hr. The concentrated hydrochloric acid (270 mL) was added at 35° C., a seed crystal was added, and the reaction mixture was stirred at 35° C. for 1 hr and at 5° C. for 1 hr. The precipitated crystals were collected by filtration, washed with water (123 mL), and dried at 60° C. under reduced pressure. To the crystals was added ethyl acetate (1.9 L), and the mixture was stirred at room temperature for 1 hr. After filtration, the insoluble material was washed with ethyl acetate (144 mL). To the filtrate was added activated carbon (16.5 g), and the mixture was stirred at 25° C. for 1 hr and filtered again. The filtrate was concentrated and dried under reduced pressure to give (6-hydroxy-1-benzofuran-3-yl)acetic acid (146 g). (6-Hydroxy-1-benzofuran-3-yl)acetic acid (130 g) was dissolved in methanol (270 mL), a solution of (1R)-1-phenylethylamine (82 g) in methanol (90 mL) was added at 60° C., and diisopropyl ether (3.6 L) was added at 55° C. After stirring at 25° C. for 2 hr, the precipitated solid was collected by filtration. The obtained solid was washed with a mixed solvent (445 mL) of methanol-diisopropyl ether (1:9), and dried at 50° C. under reduced pressure to give the title compound (198 g) as white crystals.

$^1$H NMR (500 MHz, DMSO-$d_6$): δ 1.28-1.38 (m, 3H), 3.38-3.50 (m, 2H), 4.06-4.17 (m, 1H), 6.72 (dd, 1H, J=8.5, 2.2 Hz), 6.86 (d, 1H, J=1.9 Hz), 7.21-7.29 (m, 1H), 7.29-7.38 (m, 3H), 7.38-7.44 (m, 2H), 7.56-7.63 (m, 1H). (protons derived from NH, OH and COOH were not detected)

Example 1

Synthesis of dichloro[(+)-1,2-bis((2R,5R)-2,5-diisopropylphosphorano)benzene]ruthenium (II)-N,N-dimethylformamide complex

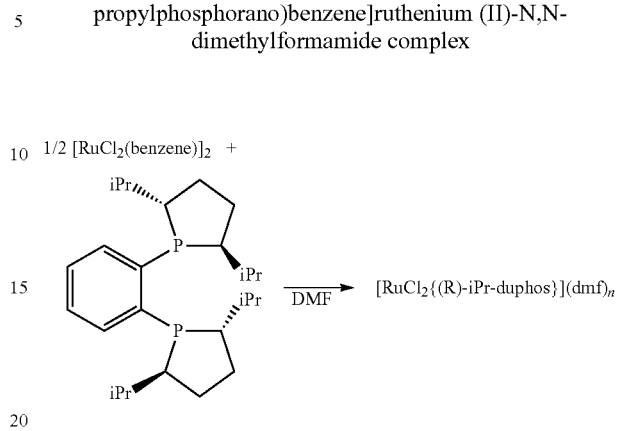

Dichlorobenzene ruthenium dimer (0.50 g) and (+)-1,2-bis((2R,5R)-2,5-diisopropylphosphorano)benzene (0.89 g) were weighted in a schlenk tube, and purged with argon. The deaerated N,N-dimethylformamide (5 mL) was added thereto, and the mixture was stirred at 100° C. for 2 hr. The mixture was concentrated at 50° C., and deaerated hexane (2.5 mL) was added to the residue (0.50 g). The mixture was suspended by stirring at 70° C. for 1.5 hr, and thereafter stirred at room temperature for 30 min. The solid was collected by filtration to give the title compound (0.45 g).

$^{31}$P(NMR) (121 MHz, CDCl$_3$, 85% H$_3$PO$_4$) δ: 92.4 (dd), 93.5 (dd), 94.7 (dd)

Example 2

Synthesis of [(3S)-6-hydroxy-2,3-dihydro-1-benzofuran-3-yl]acetic acid (1R)-1-phenylethylamine salt

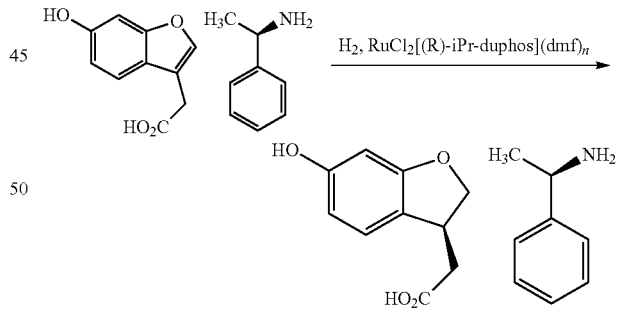

A solution of (6-hydroxy-1-benzofuran-3-yl)acetic acid (1R)-1-phenylethylamine salt (8.16 g) and dichloro[(+)-1,2-bis((2R,5R)-2,5-diisopropylphosphorano)benzene]ruthenium (II)—N,N-dimethylformamide complex (1.3 mg) in dehydrated methanol (50 ml) was stirred at 35° C. for 26 hr under a hydrogen atmosphere (1.1 MPa). After concentration, the residue was dissolved in a mixed solvent of methanol (25.0 mL)-water (3.7 mL) at around 55° C. After adding toluene (225 mL) at the same temperature, the mixture was stirred at 25° C. for 20 hr and at 0° C. for 1 hr. The precipitated crystals were collected by filtration, washed with toluene (25 mL), and dried at 50° C. under reduced pressure to give a crude product (6.65 g). The crude product was subjected to a similar recrystallization method using a mixed solvent of methanol (20.0 mL)-water (3.0 mL) and diisopropyl ether (180 mL) to give a crude product (6.16 g). The crude product was subjected to a similar recrystallization method using a mixed solvent of methanol (18.5 mL)-water (2.8 mL) and diisopropyl ether (166 mL) to give the title compound (5.81 g) as white crystals. 99.7% de.

$^1$H NMR (500 MHz, DMSO-d$_6$): δ 1.32 (d, 3H, J=7.0 Hz), 2.32 (dd, $^1$H, J=15.9, 9.3 Hz), 2.56 (dd, 1H, J=15.9, 5.7 Hz), 3.54-3.67 (m, 1H), 4.05-4.17 (m, 2H), 4.63 (t, 1H, J=9.0 Hz), 6.15 (1H, d, J=2.2 Hz), 6.22 (dd, 1H, J=8.2, 2.2 Hz), 6.97 (dd, 1H, J=8.0, 0.8 Hz), 7.20-7.29 (m, 1H), 7.29-7.38 (m, 2H), 7.38-7.44 (m, 2H). (protons derived from NH, OH and COOH were not detected)

(high performance liquid chromatography conditions) column: CHIRALPAK AD-H (manufactured by DAICEL CHEMICAL INDUSTRIES, LTD.)
mobile phase: normal hexane/ethanol/trifluoroacetic acid (volume ratio: 90/10/0.1)
flow rate: 1.0 mL/min
detection: UV 220 nm
temperature: 30° C.

Example 3

Synthesis of [(3S)-6-hydroxy-2,3-dihydro-1-benzofuran-3-yl]acetic acid (1R)-1-phenylethylamine salt

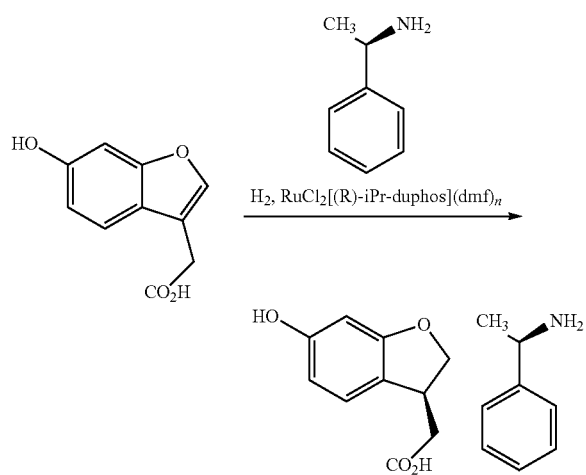

To (6-hydroxy-1-benzofuran-3-yl)acetic acid (2.80 g) and dichloro[(+)-1,2-bis((2R,5R)-2,5-diisopropylphosphorano)benzene]ruthenium (II)-N,N-dimethylformamide complex (2.1 mg) were added (1R)-1-phenylethylamine (1.77 g) and deaerated methanol (28 mL), and the mixture was stirred at 35° C. for 18 hr under a hydrogen atmosphere (0.85 MPa). The mixture was allowed to cool to room temperature, and concentrated under reduced pressure. To the concentrated residue were added ethanol (14 mL) and N,N-dimethylformamide (7.7 mL), and the mixture was dissolved by heating to 70° C. While maintaining the same temperature, diisopropyl ether (28 mL) was added dropwise. The mixture was cooled to 5° C. and stirred for 1 hr, and the solid was collected by filtration, washed with diisopropyl ether-methanol (4:1, 6 mL), and dried at 50° C. under reduced pressure to give a crude resultant product (3.58 g). To the crude product (3.00 g) were added ethanol (15 mL) and N,N-dimethylformamide (6 mL), and the mixture was dissolved by heating to 60° C. While maintaining the same temperature, diisopropyl ether (39 mL) was added dropwise, and the mixture was cooled to 5° C. The mixture was stirred at the same temperature for 2 hr, and the solid was collected by filtration, washed with diisopropyl ether-methanol (4:1, 6 mL), and dried at 50° C. under reduced pressure to give the title compound (2.66 g). 99.7% de. (high performance liquid chromatography conditions) column: CHIRALPAK AD-H (manufactured by DAICEL CHEMICAL INDUSTRIES, LTD.)
mobile phase: normal hexane/ethanol/trifluoroacetic acid (volume ratio: 90/10/0.1)
flow rate: 1.0 mL/min
detection: UV 220 nm
temperature: 30° C.

Example 4

Synthesis of methyl [(3S)-6-hydroxy-2,3-dihydro-1-benzofuran-3-yl]acetate

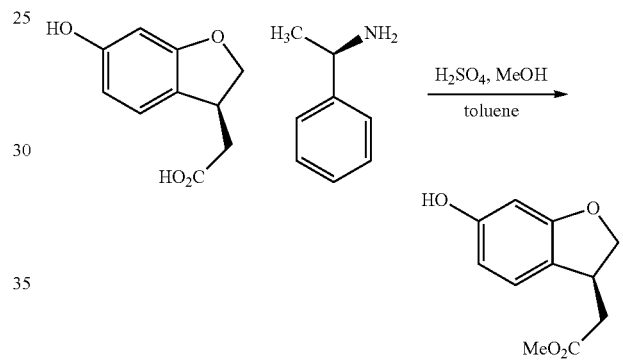

To a solution of [(3S)-6-hydroxy-2,3-dihydro-1-benzofuran-3-yl]acetic acid (1R)-1-phenylethylamine salt (1.0 g) in methanol (3 mL)-toluene (8 mL) was added concentrated sulfuric acid (0.412 mg), and the mixture was stirred at 60° C. for 2 hr. The mixture was concentrated, toluene (5 mL) was added, and the mixture was concentrated again. To the residue were added toluene (5 mL), tetrahydrofuran (8 mL) and 1N hydrochloric acid (5 mL) to perform an extraction operation. The organic layer was washed with water, 5% aqueous sodium bicarbonate and water, and concentrated, and the residue was dissolved in toluene (8 mL). The activated carbon (100 mg) was added, and the mixture was stirred at room temperature for 30 min. After filtration, the filtrate was concentrated. The obtained crude product was dissolved in toluene (2 mL), seed crystal was added, and the mixture was stirred at room temperature for 16 hr. n-Heptane (6 mL) was added, and the mixture was stirred at room temperature for 5 hr and at 0° C. for 1 hr. The precipitated crystals were collected by filtration, and dried at 50° C. to give the title compound (554 mg) as white crystals. 99.7% ee.

$^1$H NMR (500 MHz, CD$_3$OD): δ 2.53 (dd, 1H, J=16.2, 8.7 Hz), 2.71 (dd, 1H, J=16.2, 6.0 Hz), 3.63-3.75 (m, 1H), 3.68 (s, 3H), 4.19 (dd, 1H, J=9.0, 6.1 Hz), 4.65 (t, 1H, J=9.0 Hz), 4.84 (br s, 1H), 6.19 (d, 1H, J=2.2 Hz), 6.26 (dd, 1H, J=8.2, 2.2 Hz), 6.94 (d, 1H, J=7.3 Hz).

(high performance liquid chromatography conditions) column: CHIRALPAK AD-RH (manufactured by DAICEL CHEMICAL INDUSTRIES, LTD.)

mobile phase: water/acetonitrile (volume ratio: 77/23)
flow rate: 1.0 mL/min
detection: UV 220 nm
temperature: 30° C.

Example 5

Synthesis of [(3S)-6-hydroxy-2,3-dihydro-1-benzofuran-3-yl]acetic acid (S)-2-amino-1,1-diphenylpropan-1-ol salt

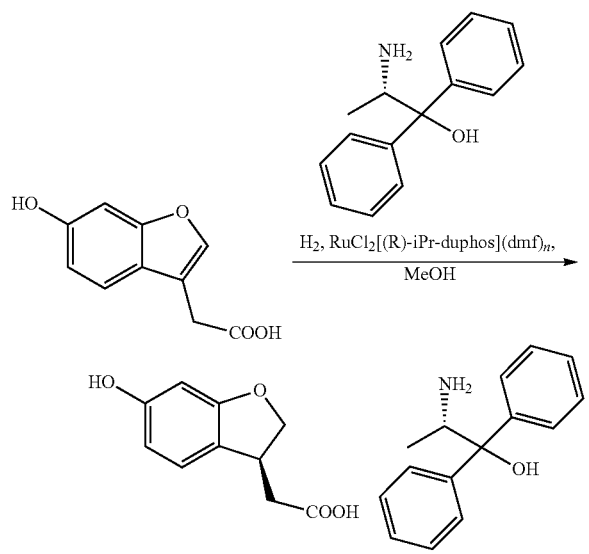

(6-Hydroxy-1-benzofuran-3-yl)acetic acid (25 g), dichloro[(+)-1,2-bis((2R,5R)-2,5-diisopropylphosphorano) benzene]ruthenium (II)-N,N-dimethylformamide complex (19.1 mg) and (S)-2-amino-1,1-diphenylpropan-1-ol (29.5 g) were weighted in an autoclave and substituted with argon. Dehydrated methanol (250 mL) was added and the mixture was purged with hydrogen, pressurized under a hydrogen pressure (1.0 MPa), and reacted at 35° C. for 15 hr. The reaction mixture was concentrated under reduced pressure, methanol (109 mL) and N,N-dimethylformamide (27 mL) were added, and the mixture was dissolved by heating at 50° C. Isopropyl ether (200 mL) was added dropwise at 60° C., seed crystal was added, and isopropyl ether (369 mL) was added dropwise. The mixture was cooled to room temperature, stirred for 4 hr and stirred for 1 hr under ice-cooling, and the solid was collected by filtration. The solid was dried at 60° C. under reduced pressure to give the title compound (38.98 g). 99.8% de.

$^1$H NMR (500 MHz, DMSO-$d_6$): δ 0.85-0.92 (m, 1H), 2.36 (dd, J=14.19 Hz), 2.59 (dd, J=16.24, 2.68 Hz, 1H), 3.55-3.65 (m, 1H), 4.13 (dd, J=8.83 Hz, 1H), 4.64 (t, J=8.83 Hz, 1H), 6.16 (d, J=2.21 Hz, 1H), 6.23 (dd, J=8.20, 2.21 Hz, 1H), 6.93-7.00 (m, 1H), 7.09-7.21 (m, 2H), 7.22-7.35 (m, 4H), 7.51 (d, J=7.57 Hz, 2H), 7.63 (dd, J=8.20 Hz, 2H)
(high performance liquid chromatography conditions)
column: CHIRALPAK AD-H (manufactured by DAICEL CHEMICAL INDUSTRIES, LTD.)
mobile phase: normal hexane/ethanol/trifluoroacetic acid (volume ratio: 90/10/0.1)
flow rate: 1.0 mL/min
detection: UV 220 nm
te mperature: 30° C.

Reference Example 3

Synthesis of (6-hydroxy-1-benzofuran-3-yl)acetic acid (S)-2-amino-1,1-diphenylpropan-1-ol salt

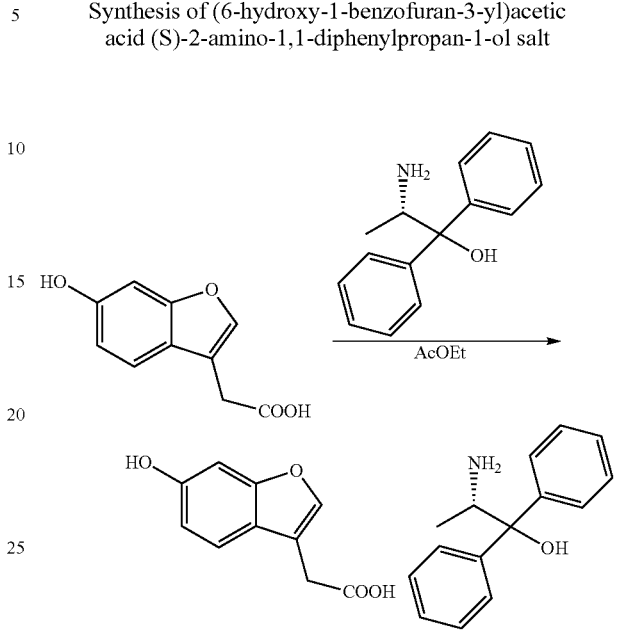

(6-Hydroxy-1-benzofuran-3-yl)acetic acid (25.00 g) and (S)-2-amino-1,1-diphenylpropan-1-ol (29.57 g) were added to ethyl acetate (175 mL), and the mixture was dissolved by stirring at 60° C. After allowing to cool to room temperature, isopropyl ether (200 mL) was added, and the mixture was stirred for 1 hr. The solid was collected by filtration, and washed with a mixed solvent (1:1, 100 mL) of ethyl acetate-isopropyl ether. The solid was dried under reduced pressure at 50° C. to give the title compound (53.81 g).

$^1$H NMR (500 MHz, DMSO-$d_6$): δ 0.86 (d, J=5.67 Hz, 3H), 3.51 (br.s., 2H), 4.06-4.16 (m, 1H), 6.72 (dd, J=8.35, 2.05 Hz, 1H), 6.86 (d, J=1.89 Hz, 1H), 7.10-7.15 (m, 2H), 7.15-7.37 (m, 5H), 7.49 (dd, J=8.35, 1.42 Hz, 2H), 7.58-7.65 (m, 3H)

Example 6

Synthesis of [(3S)-6-hydroxy-2,3-dihydro-1-benzofuran-3-yl]acetic acid (S)-2-amino-1,1-diphenylpropan-1-ol salt

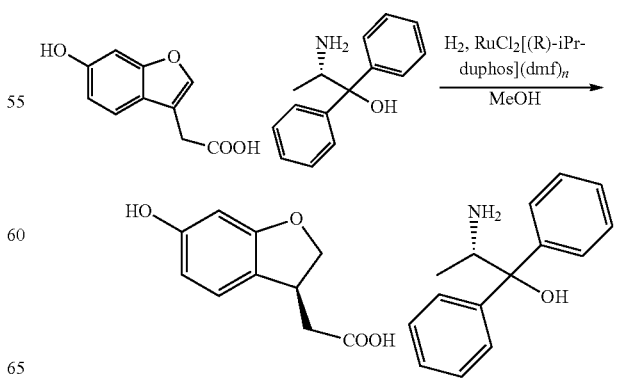

A solution of (6-hydroxy-1-benzofuran-3-yl)acetic acid (S)-2-amino-1,1-diphenylpropan-1-ol salt (19.64 g) and dichloro[(+)-1,2-bis((2R,5R)-2,5-diisopropylphosphorano)benzene]ruthenium (II)-N,N-dimethylformamide complex (2.3 mg) in dehydrated methanol (90 ml) was stirred at 35° C. for 22 hr under a hydrogen atmosphere (1.1 MPa). To the reaction solution was added methanol (9 mL) to give a methanol solution of the title compound. 81.3% de
(high performance liquid chromatography conditions)
column: CHIRALPAK AD-H (manufactured by DAICEL CHEMICAL INDUSTRIES, LTD.)
mobile phase: normal hexane/ethanol/trifluoroacetic acid (volume ratio: 90/10/0.1)
flow rate: 1.0 mL/min
detection: UV 220 nm
temperature: 30° C.

Example 7

Synthesis of methyl [(3R)-6-hydroxy-2,3-dihydro-1-benzofuran-3-yl]acetate

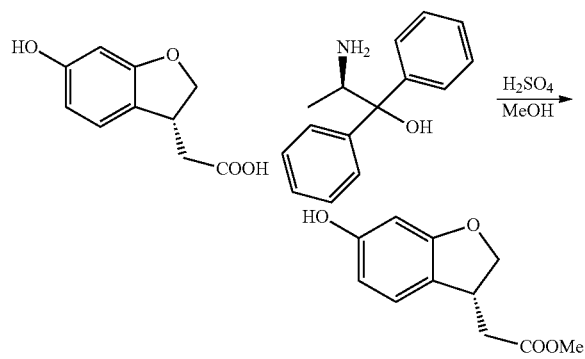

[(3R)-6-Hydroxy-2,3-dihydro-1-benzofuran-3-yl]acetic acid (R)-2-amino-1,1-diphenylpropan-1-ol salt (100 g) and sulfuric acid (30.26 g) were added to methanol (120 mL), and the mixture was stirred at 60° C. for 2 hr. After allowing to cool to room temperature, the solvent was concentrated under reduced pressure. To the residue were added toluene (831 mL), tetrahydrofuran (415 mL) and 1M hydrochloric acid (500 mL), and the mixture was partitioned. The organic layer was washed with water (500 mL), 5% aqueous sodium hydrogen carbonate solution (500 mL) and water (500 mL). The organic layer was concentrated, and toluene (110 mL) was added to the residue. The mixture was heated to 50° C., dissolved, allowed to cool to room temperature, and solid precipitation was confirmed. Normal heptane (220 mL) was added, and the mixture was stirred at room temperature for 5 hr. After cooling to 5° C., the solid was collected by filtration, washed with a mixed solution (1:2, 24 mL) of toluene-normal heptane. The solid was dried at 50° C. under reduced pressure to give the title compound (45.19 g). 99.6% ee.
(high performance liquid chromatography conditions)
column: CHIRALPAK AD-RH (manufactured by DAICEL CHEMICAL INDUSTRIES, LTD.)
mobile phase: water/acetonitrile (volume ratio: 77/23)
flow rate: 1.0 mL/min
detection: UV 220 nm
temperature: 30° C.

Reference Example 4

Synthesis of methyl((3S)-6-trifluoromethylsulfonyloxy-2,3-dihydro-1-benzofuran-3-yl)acetate

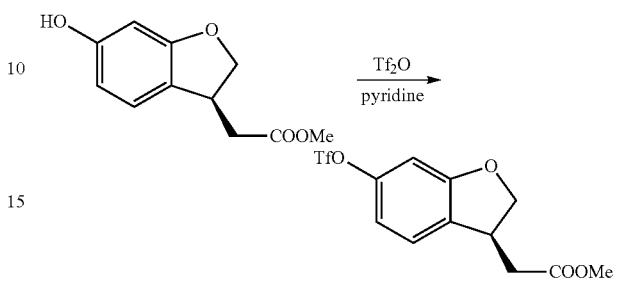

To methyl((3S)-6-hydroxy-2,3-dihydro-1-benzofuran-3-yl)acetate (100 g) was added pyridine (500 mL), and the mixture was stirred at room temperature for 10 min. Trifluoromethanesulfonic anhydride (142 g) was added dropwise at 0-20° C., and the mixture was stirred at room temperature for 1 hr. The reaction mixture was washed with water (500 mL), 6M hydrochloric acid (500 mL), 5% aqueous sodium hydrogen carbonate solution (500 g) and water (500 mL). To the organic layer was added magnesium sulfate (40 g), and the mixture was stirred at room temperature for 10 min and separated by filtration. The filtrate was concentrated under reduced pressure to give the title compound (162.59 g) as a dark-red oil.

$^1$H NMR (500 MHz, CDCl$_3$): δ 2.61 (dd, J=20.0, 10.0 Hz, 1H), 2.79 (dd, J=20.0 Hz, 5.0 Hz, 1H), 3.71 (s, 3H), 3.83-3.93 (m, 1H), 4.34 (dd, J=10.0 Hz, 1H), 4.34 (dd, J=10.0, 5.0 Hz, 1H), 4.83 (t, J=10.0 Hz, 1H), 6.71 (d, J=5.0 Hz, 1H), 6.71 (d, J=5.0 Hz, 1H), 6.76 (dd, J=10.0, 5.0 Hz, 1H), 7.20 (d, J=10.0 Hz, 1H). $^{13}$C NMR (125 MHz, CDCl$_3$) δ 37.6, 38.8, 51.7, 78.0, 103.6, 113.1, 118.6 (q, $^1$J$_{cf}$=320.3 Hz), 124.9, 129.9, 149.6, 161.1, 171.7.

Reference Example 5

Synthesis of 3-(methylthio)propyl 4-methylbenzenesunfonate

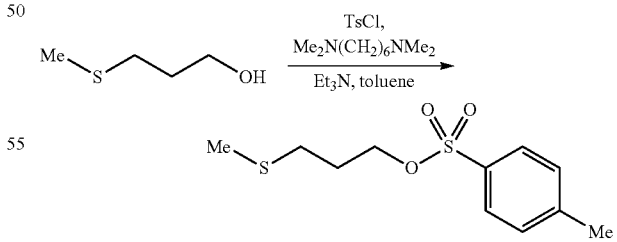

3-Methylthiopropanol (10 g), triethylamine (14.3 g) and N,N,N',N'-tetramethyl-1,6-diaminohexane (1.62 g) were dissolved in toluene (100 mL), and the solution was cooled to 6° C. or below. While cooling to 6° C. or below, tosyl chloride (2.69 g) dissolved in toluene (66 mL) was added dropwise, and the mixture was stirred at 6° C. or below for 3 hr. After the reaction, water (100 mL) was added dropwise, and the mixture was heated to room temperature and partitioned. The organic layer was washed twice with water (100 mL) and concentrated at 40° C. to give the title compound (24.1 g) as a pale-yellow oil. $^1$H NMR (300 MHz, CDCl$_3$): δ 1.81-1.95 (2H, m), 2.03 (3H, s), 2.45 (3H, s), 2.49-2.53 (2H, m), 4.15 (2H, t, J=5.9 Hz), 7.34-7.37 (2H, d, J=8.0 Hz), 7.78-7.80 (2H, d, J=7.6 Hz).

Reference Example 6

Synthesis of 3-(methylsulfonyl)propyl 4-methylbenzenesunfonate

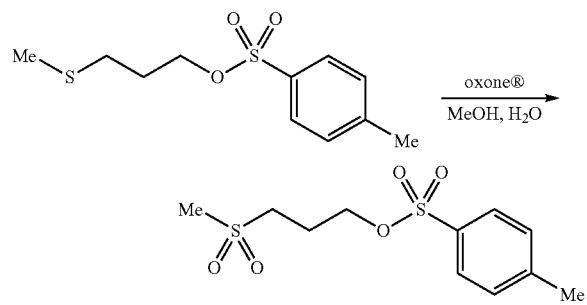

3-(Methylthio)propyl 4-methylbenzenesunfonate (29.4 g) was dissolved in methanol, and the mixture was cooled to 6C or below. While cooling to 6° C. or below, oxone (registered trade mark; 105.2 g) dissolved in water (400 mL) was added dropwise over 1 hr. After stirring at 6° C. or below for 1 hr, the mixture was stirred at room temperature for 14 hr. Water (800 mL) was added, and the mixture was stirred at 6° C. or below for 1 hr. The precipitated solid was collected by filtration, and washed twice with water (400 mL). The solid was suspended in methanol (150 mL), and the suspension was heated to 65° C. Water (150 mL) was added dropwise over 30 min, and the mixture was cooled to room temperature and stirred at 6° C. or below for 1 hr. The solid was collected by filtration, and washed twice with water (150 mL). The solid was vacuum-dried at 50° C. to give white title compound (25.21 g).

$^1$H NMR (300 MHz, CDCl$_3$): δ 2.17-2.28 (2H, m), 2.46 (3H, s), 2.91 (3H, s), 3.07-3.15 (2H, m), 4.18 (2H, t, J=5.9 Hz), 7.34-7.37 (2H, d, J=8.0 Hz), 7.78-7.80 (2H, d, J=8.3 Hz).

Example 8

Synthesis of 2-bromo-1,3-dimethyl-5-[3-(methylsulfonyl)propoxy]benzene

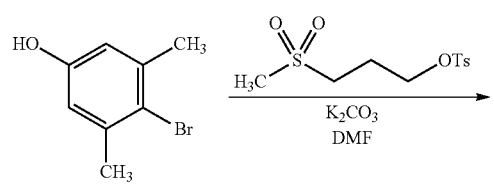

-continued

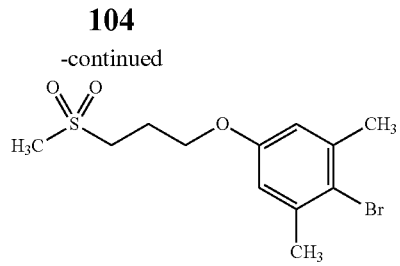

4-Bromo-3,5-dimethylphenol (400.0 g), 3-(methylsulfonyl)propyl 4-methylbenzenesulfonate (727.3 g) and potassium carbonate (357.6 g) were added to N,N-dimethylformamide (4000 mL), and the mixture was stirred. The mixture was heated to 70° C., stirred for 20 hr and cooled to 5° C. Water (2000 mL) was added dropwise at 10° C. or below, seed crystal was added, and water (4000 mL) was further added. The mixture was stirred at room temperature overnight and at 10° C. or below for 2 hr. The precipitated crystals were collected by filtration, washed with water (4000 mL) and dried to give the title compound (631.0 g).

Example 9

Synthesis of 2-bromo-1,3-dimethyl-5-[3-(methylsulfonyl)propoxy]benzene

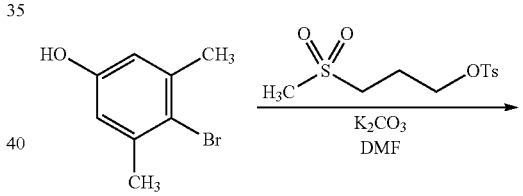

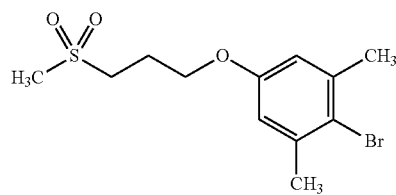

4-Bromo-3,5-dimethylphenol (40.00 g), 3-(methylsulfonyl)propyl 4-methylbenzenesulfonate (72.71 g) and potassium carbonate (35.75 g) were added to N,N-dimethylformamide (400 mL), and the mixture was stirred. The mixture was heated to 70° C., stirred for 46 hr, and cooled to 5° C. Water (200 mL) was added dropwise at 10° C. or below, seed crystal (60 mg) was added, and water (400 mL) was continuously added. After stirring for 2 hr, the precipitated crystals were collected by filtration, washed with water (400 mL) and dried to give the title compound (63.08 g).

$^1$H NMR (300 MHz, CDCl$_3$): δ 2.28-2.36 (m, 2H), 2.38 (s, 6H), 2.93-2.97 (m, 3H), 3.20-3.26 (m, 2H), 4.07 (t, J=5.8 Hz, 2H), 6.63 (s, 2H), 7.26 (s, 1H).

Example 10

Synthesis of 2',6'-dimethyl-4'-[3-(methylsulfonyl)propoxy]biphenyl-3-carbaldehyde (homogeneous reaction example)

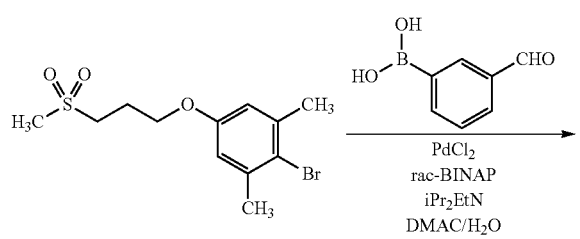

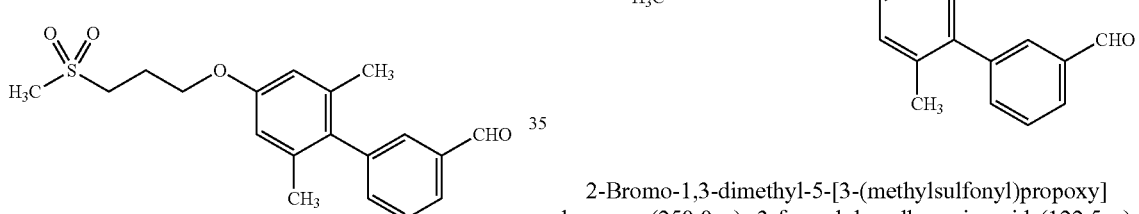

Under a nitrogen atmosphere, a mixture of palladium chloride (82.8 mg), 2,2'-bis(diphenylphosphino)-1,1'-binaphthyl (387.7 mg), N,N-dimethylacetamide (500 mL) and diisopropylethylamine (60.4 g) was stirred at 70° C. for 2 hr. To the obtained mixture were added 2-bromo-1,3-dimethyl-5-[3-(methylsulfonyl)propoxy]benzene (100.0 g) and 3-formylphenylboronic acid (46.7 g), and the mixture was stirred at 70° C. for 1 hr. Deaerated water (450 mL) was added dropwise at 70° C., and the mixture was stirred for 8 hr. The reaction mixture was cooled, 10% brine (200 mL) was added, and the mixture was extracted with toluene (600 mL). The aqueous layer was extracted again with toluene (600 mL). The organic layers were combined, and washed with 10% brine (600 mL) and then water (600 mL). To the organic layer was added activated carbon (10.0 g), and the mixture was stirred at room temperature for 30 min. The insoluble material was removed by filtration, and washed with toluene (300 mL). The filtrate was concentrated to 300 mL under reduced pressure, to which was added toluene (600 mL), and the mixture was concentrated again to 300 mL. To the concentrated solution was added ethanol (300 mL), and the mixture was stirred at room temperature for 30 min. Normal heptane (1200 mL) was added dropwise, and the mixture was stirred at room temperature for 1 hr and at 5° C. for 2 hr. The precipitated solid was collected by filtration, and the solid was washed with a mixture (300 mL) of ethanol*normal heptane (1:4), and dried under reduced pressure to give 2',6'-dimethyl-4'-[3-(methylsulfonyl)propoxy]biphenyl-3-carbaldehyde (96.0 g).

Example 11

Synthesis of 2',6'-dimethyl-4'-[3-(methylsulfonyl)propoxy]biphenyl-3-carbaldehyde (heterogeneous reaction example)

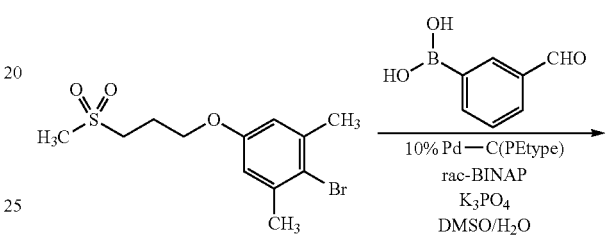

2-Bromo-1,3-dimethyl-5-[3-(methylsulfonyl)propoxy]benzene (250.0 g), 3-formylphenylboronic acid (122.5 g), tripotassium phosphate (330.4 g), 10% palladium carbon 50% water-containing product (12.5 g) and 2,2'-bis(diphenylphosphino)-1,1'-binaphthyl (5.5 g) were added to dimethyl sulfoxide (2500 mL) and water (1250 mL). After deaeration and nitrogen substitution, the mixture was heated, and stirred at 80° C. for 3 hr. The reaction mixture was left standing, and the oil component in the lower layer was removed. The mixture was cooled, ethyl acetate (875 mL) was added, and the mixture was stirred. The insoluble material was removed by filtration, and washed with ethyl acetate (625 mL). To the filtrate was added 10% brine (1500 mL), the mixture was stirred, and the organic layer was separated. The aqueous layer was extracted again with ethyl acetate (1500 mL). The organic layers were combined, and washed twice with 10% brine (1500 mL). The organic layer was concentrated to 750 mL, ethyl acetate (1500 mL) was added, and an operation to concentrate the mixture to 750 mL again was performed twice. To the concentrate were added ethyl acetate (1250 mL) and activated carbon (25 g), and the mixture was stirred at room temperature for 30 min. The insoluble material was removed by filtration, and washed with ethyl acetate (750 mL). The filtrate was concentrated to 750 mL under reduced pressure, and stirred at room temperature overnight. Normal heptane (3750 mL) was added dropwise, and the mixture was stirred at room temperature for 2 hr. The precipitated solid was collected by filtration, and the solid was washed with a mixture (750 mL) of ethyl acetate.normal heptane (1:5), and

Example 12

Synthesis of 2',6'-dimethyl-4'-[3-(methylsulfonyl)propoxy]biphenyl-3-carbaldehyde

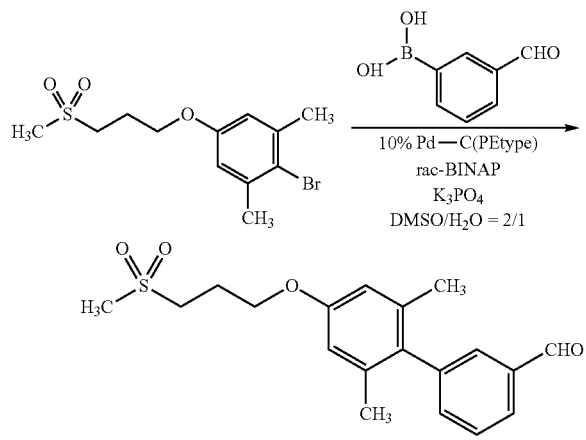

2-Bromo-1,3-dimethyl-5-[3-(methylsulfonyl)propoxy]benzene (15.00 g), 3-formylphenylboronic acid (7.38 g), tripotassium phosphate (19.83 g), palladium carbon (3.0 g) and 2,2'-bis-(diphenylphosphino)-1,1'-binaphthyl (1.16 g) were added to dimethyl sulfoxide (150 mL) and water (75 mL), and the mixture was stirred at 80° C. for 5 hr. Activated carbon (1.5 g) was added, and the mixture was filtered with heating at 80° C. to remove the insoluble material. The filtrate was cooled to room temperature and stirred for 5 hr. The filtrate was cooled to 10° C. or below and stirred for 2 hr. Water (120 mL) was added dropwise, and the mixture was stirred for 1 hr. Water (150 mL) was added dropwise, and the mixture was stirred for 1 hr. The crystallized solid was collected by filtration, and the solid was washed with water (150 mL), and dried under reduced pressure to give 2',6'-dimethyl-4'-[3-(methylsulfonyl)propoxy]biphenyl-3-carbaldehyde (15.43 g).

$^1$H NMR (300 MHz, CDCl$_3$) δ 1.99 (s, 6H), 2.97 (s, 3H), 3.28 (t, J=7.5 Hz, 2H), 4.14 (t, J=5.8 Hz, 2H), 6.67 (s, 2H), 7.40-7.45 (m, 1H), 10.05 (s, 1H).

Reference Example 7

Synthesis of {2',6'-dimethyl-4'-[3-(methylsulfonyl)propoxy]biphenyl-3-yl}methanol

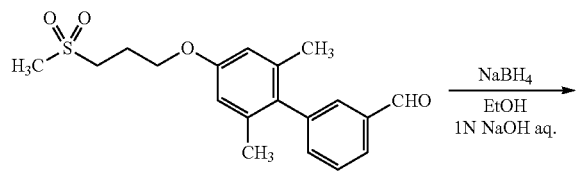

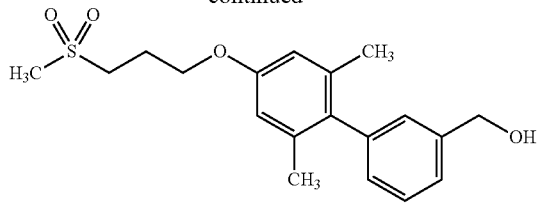

To 2',6'-dimethyl-4'-[3-(methylsulfonyl)propoxy]biphenyl-3-carbaldehyde (50.0 g) was added ethanol (400 mL), and the mixture was stirred for 10 min. To this solution was added dropwise at 25° C. a solution separately prepared by dissolving sodium hydroxide (1.0 g) in water (125 mL) and adding sodium borohydride (3.28 g), and the wall-side of the titration equipment was washed with water (50 mL). The mixture was stirred at 25° C. for 1 hr, activated carbon (10.0 g) was added, and the mixture was stirred for 1 hr. The insoluble material was removed by filtration, and washed with a mixed solution (200 mL) of water.ethanol (1:4). 6M Hydrochloric acid was added to the filtrate at 25° C. to adjust the mixture to pH 3.0. Then, 1 mol/L aqueous sodium hydroxide solution was added to adjust the mixture to pH 7.0. The mixture was concentrated to 200 mL, the attachment on the wall was washed with a mixed solution (50 mL) of water-ethanol (1:4), and the mixture was stirred at 50° C. for 30 min. Water (50 mL) was added dropwise, and the mixture was stirred at 50° C. for 30 min. After stirring at 25° C. for 2 hr, water (450 mL) was added dropwise, and the mixture was stirred at 25° C. for 2 hr. The precipitated solid was collected by filtration, and the solid was washed with water (500 mL) and dried at 60° C. under reduced pressure to give {2',6'-dimethyl-4'-[3-(methylsulfonyl)propoxy]biphenyl-3-yl}methanol (47.6 g).

Example 13

Synthesis of 3'-chloromethyl-2,6-dimethyl-4-[3-(methylsulfonyl)propoxy]biphenyl

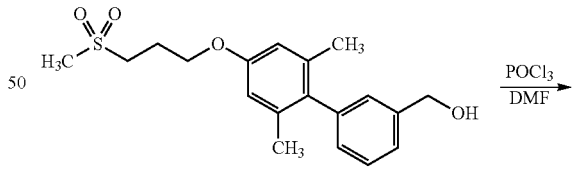

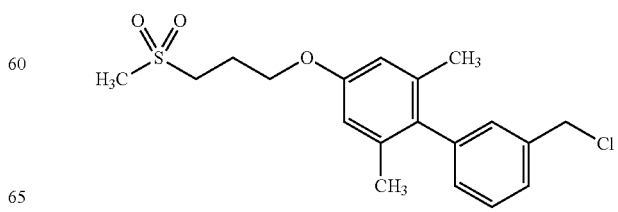

To {2',6'-dimethyl-4'-[3-(methylsulfonyl)propoxy]biphenyl-3-yl}methanol (30.0 g) was added N,N-dimethylformamide (90 mL), and the mixture was stirred for 20 min. To the mixture was added dropwise at 25° C. a separately prepared solution of phosphorus oxychloride (17.2 g) in N,N-dimethylformamide (54.0 mL), and the mixture was stirred at 25° C. for 4 hr. Water (30 mL) and then methanol (30 mL) were added dropwise. Seed crystal was added, and the mixture was stirred for 1 hr. Methanol (120 mL) was added, and the mixture was stirred for 1 hr. Then, water (120 mL) was added dropwise, and the mixture was stirred for 1 hr. The precipitated crystals were collected by filtration, and washed with water (300 mL). The obtained crystals were suspended in water (300 mL), and the mixture was stirred. The crystals were collected by filtration, washed with water (300 mL), and dried at 60° C. to give 3'-chloromethyl-2,6-dimethyl-4-[3-(methylsulfonyl)propoxy]biphenyl (28.8 g).

Example 14

Synthesis of 3'-chloromethyl-2,6-dimethyl-4-[3-(methylsulfonyl)propoxy]biphenyl

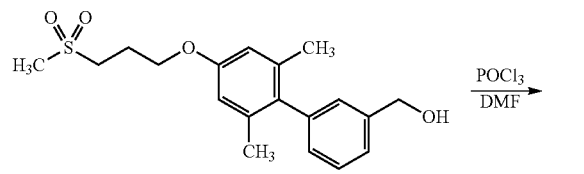

To {2',6'-dimethyl-4'-[3-(methylsulfonyl)propoxy]biphenyl-3-yl}methanol (2.40 g) was added N,N-dimethylformamide (7.2 mL), and the mixture was stirred for 20 min. The N,N-dimethylformamide solution was added dropwise at 25° C. to a separately prepared solution of phosphorus oxychloride (1.37 g) in N,N-dimethylformamide (4.8 mL). After stirring at 25° C. for 1 hr, water (2.4 mL), then methanol (12 mL), and water (2.4 mL) were added dropwise. Seed crystal was added, and the mixture was stirred at room temperature for 1 hr and at 10° C. or below for 1 hr. The precipitated crystals were collected by filtration, washed with water (24 mL), and dried at 50° C. under reduced pressure to give 3'-chloromethyl-2,6-dimethyl-4-[3-(methylsulfonyl)propoxy]biphenyl (2.33 g).

$^1$H NMR (300 MHz, CDCl$_3$) δ 2.00 (s, 6H), 2.29-2.40 (m, 2H), 2.97 (s, 3H), 3.22-3.30 (m, 2H), 4.10-4.15 (m, 2H), 4.62 (s, 2H), 6.45 (s, 2H), 7.05-7.10 (m, 1H), 7.15 (s, 1H), 7.30-7.44 (m, 2H).

Example 15

Synthesis of [(3S)-6-({2',6'-dimethyl-4'-[3-(methylsulfonyl)propoxy]biphenyl-3-yl}methoxy)-2,3-dihydro-1-benzofuran-3-yl]acetic acid

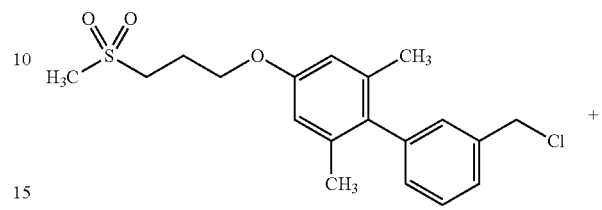

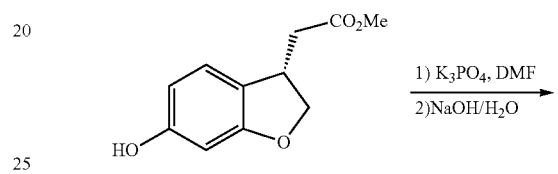

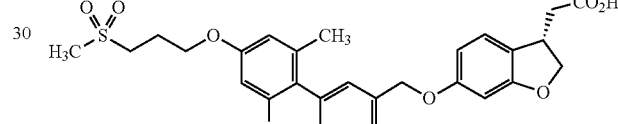

To a solution of methyl [(3S)-6-hydroxy-2,3-dihydro-1-benzofuran-3-yl]acetate (10.0 g) and 3'-chloromethyl-2,6-dimethyl-4-[3-(methylsulfonyl)propoxy]biphenyl (17.6 g) in N,N-dimethylformamide (30.0 mL) was added tripotassium phosphate (16.8 g), and the mixture was stirred at 60° C. for 3 hr. 2.4M Aqueous sodium hydroxide solution (32.9 g) was added, and the mixture was stirred at 80° C. for 2 hr. The reaction mixture was cooled, water (100 mL) was added, and the mixture was extracted with toluene (50 mL). To the aqueous layer was added toluene (50 mL), and the mixture was extracted. To the obtained aqueous layer were added acetone (10 mL) and concentrated hydrochloric acid (17.6 mL), and the mixture was stirred at 30° C. for 1 hr, at 50° C. for 30 min, and at 25° C. for 2 hr. The precipitated crystals were collected by filtration, and washed with a mixed solution (50 mL) of acetone.water (3:7) and then water (50 mL). The obtained crystals were dried at 60° C. under reduced pressure to give [(3S)-6-({2',6'-dimethyl-4'-[3-(methylsulfonyl)propoxy]biphenyl-3-yl}methoxy)-2,3-dihydro-1-benzofuran-3-yl]acetic acid (24.3 g). 100% ee. (high performance liquid chromatography conditions)

column: CHIRALPAK AD-H (manufactured by DAICEL CHEMICAL INDUSTRIES, LTD.)
mobile phase: normal hexane/isopropylalcohol/trifluoroacetic acid (volume ratio: 50/50/0.1)
flow rate: 0.5 mL/min
detection: UV 220 nm
temperature: 30° C.

Example 16

Synthesis of [(3S)-6-({2',6'-dimethyl-4'-[3-(methylsulfonyl)propoxy]biphenyl-3-yl}methoxy)-2,3-dihydro-1-benzofuran-3-yl]acetic acid

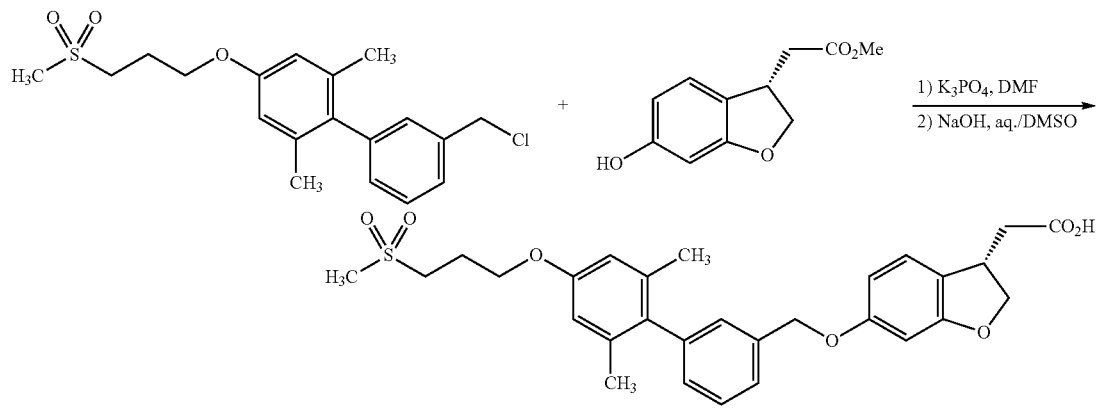

To a solution of methyl [(3S)-6-hydroxy-2,3-dihydro-1-benzofuran-3-yl]acetate (85.00 g) and 3'-chloromethyl-2,6-dimethyl-4-[3-(methylsulfonyl)propoxy]biphenyl (149.91 g) in N,N-dimethylformamide (255 mL) was added tripotassium phosphate (130.00 g), and the mixture was stirred at 60° C. for 3 hr. The reaction mixture was cooled to room temperature, ethyl acetate (1020 mL) and water (1020 mL) were added, and the mixture was partitioned. The organic layer was washed with water (1020 mL) and 10% brine (1020 mL) and concentrated under reduced pressure. To the concentrated residue were added dimethyl sulfoxide (510 mL) and 2M aqueous sodium hydroxide solution, and the mixture was stirred at 60° C. for 1 hr. The mixture was allowed to cool to room temperature, and washed with ethyl acetate (1020 mL). The organic layer was washed with water (1223 mL). 6M Hydrochloric acid was added, and the mixture was extracted with ethyl acetate (1020 mL). The organic layer was washed with water (1020 mL) and 10% brine (1020 mL) and concentrated to give [(3S)-6-({2',6'-dimethyl-4'-[3-(methylsulfonyl)propoxy]biphenyl-3-yl}methoxy)-2,3-dihydro-1-benzofuran-3-yl]acetic acid (212.60 g). 100% ee. (high performance liquid chromatography conditions)

column: CHIRALPAK AD-H (manufactured by DAICEL CHEMICAL INDUSTRIES, LTD.)

mobile phase: normal hexane/isopropylalcohol/trifluoroacetic acid (volume ratio: 50/50/0.1)

flow rate: 0.5 mL/min detection: UV 220 nm temperature: 30° C.

Example 17

Synthesis of [(3S)-6-({2',6'-dimethyl-4'-[3-(methylsulfonyl)propoxy]biphenyl-3-yl}methoxy)-2,3-dihydro-1-benzofuran-3-yl]acetic acid hydrate crystal

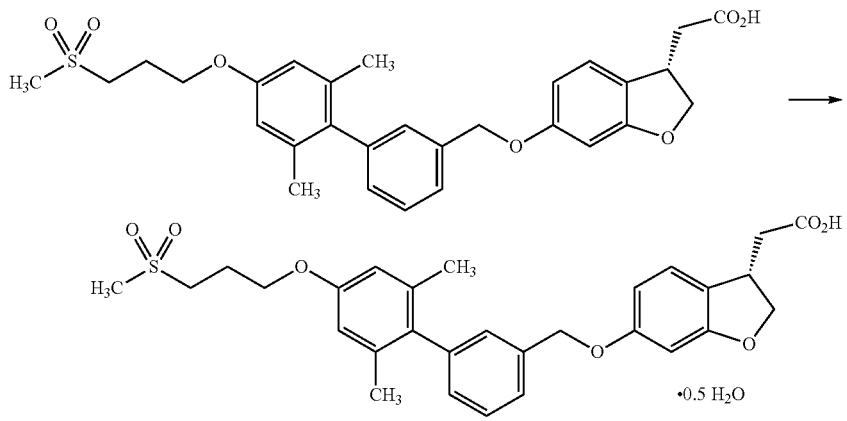

To [(3S)-6-({2',6'-dimethyl-4'-[3-(methylsulfonyl)propoxy]biphenyl-3-yl}methoxy)-2,3-dihydro-1-benzofuran-3-yl]acetic acid (15.0 g) were added acetone (30 mL) and water (10.5 mL) for dissolution therein. Activated carbon (0.45 g) was added, and the mixture was stirred at 45° C. for 10 min. The insoluble material was removed by filtration and washed with acetone (7.5 mL). Water (3 mL) was added dropwise to the filtrate, and the mixture was allowed to cool to room temperature. Seed crystal was added, and the mixture was stirred for 30 min. At 20° C., water (9 mL) and water (15 mL) was respectively added over 1 hr, and the mixture was stirred at 10° C. for 1 hr. The precipitated crystals were collected by filtration, and washed with a mixed solution (30 mL) of acetone.water (1:1) and then water (30 mL). The obtained crystals were dried at 30° C. under reduced pressure (1.5–3.0 kPa) to give [(3S)-6-({2',6'-dimethyl-4'-[3-(methylsulfonyl) propoxy]biphenyl-3-yl}methoxy)-2,3-dihydro-1-benzofuran-3-yl]acetic acid hydrate as crystals (14.4 g). 100% ee.
(high performance liquid chromatography conditions)
column: CHIRALPAK AD-H (manufactured by DAICEL CHEMICAL INDUSTRIES, LTD.)
mobile phase: normal hexane/isopropylalcohol/trifluoroacetic acid (volume ratio: 50/50/0.1)
flow rate: 0.5 mL/min
detection: UV 220 nm
temperature: 30° C.

Example 18

Synthesis of [(3S)-6-({2',6'-dimethyl-4'-[3-(methylsulfonyl)propoxy]biphenyl-3-yl}methoxy)-2,3-dihydro-1-benzofuran-3-yl]acetic acid hydrate crystal

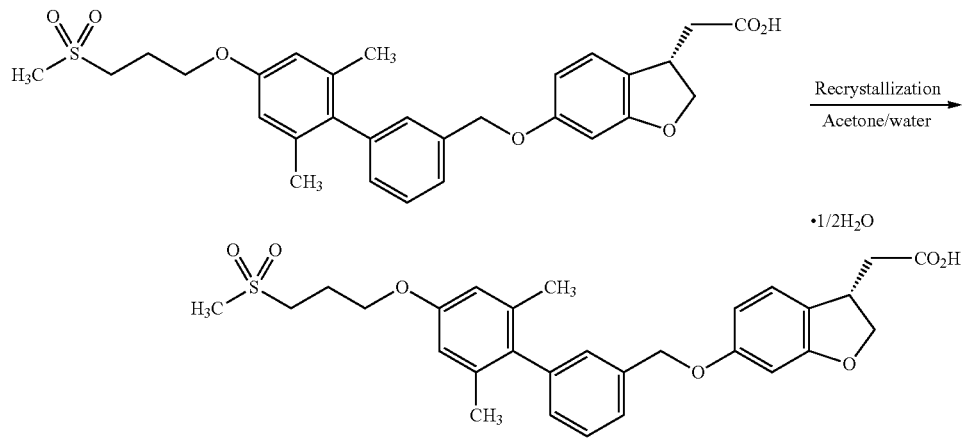

[(3S)-6-({2',6'-Dimethyl-4'-[3-(methylsulfonyl)propoxy] biphenyl-3-yl}methoxy)-2,3-dihydro-1-benzofuran-3-yl] acetic acid (212.60 g) was dissolved in acetone (510 mL). Water (255 mL) was added dropwise. Seed crystal was added, and the mixture was stirred for 2 hr. The mixture was cooled to 10° C. or below, and stirred for 2 hr. While cooling to 10° C. or below, water (765 mL) was added dropwise, and the mixture was stirred for 2 hr. The precipitated solid was collected by filtration, and washed with a mixed solution (1360 mL) of acetone.water (1:4). The obtained solid was dried at 50° C. under reduced pressure to give [(3S)-6-({2',6'-dimethyl-4'-[3-(methylsulfonyl)propoxy]biphenyl-3-yl}methoxy)-2,3-dihydro-1-benzofuran-3-yl]acetic acid hydrate as crystals (190.94 g). 100% ee.
(high performance liquid chromatography conditions)
column: CHIRALPAK AD-H (manufactured by DAICEL CHEMICAL INDUSTRIES, LTD.)
mobile phase: normal hexane/isopropylalcohol/trifluoroacetic acid (volume ratio: 50/50/0.1)
flow rate: 0.5 mL/min
detection: UV 220 nm
temperature: 30° C.

Example 19

Synthesis of [(3S)-6-({2',6'-dimethyl-4'-[3-(methylsulfonyl)propoxy]biphenyl-3-yl}methoxy)-2,3-dihydro-1-benzofuran-3-yl]acetic acid anhydride crystal (C form crystal)

[(3S)-6-({2',6'-Dimethyl-4'-[3-(methylsulfonyl)propoxy] biphenyl-3-yl}methoxy)-2,3-dihydro-1-benzofuran-3-yl] acetic acid hydrate (0.5 hydrate) was heated at 60° C. for 30 min to give [(3S)-6-({2',6'-dimethyl-4'-[3-(methylsulfonyl) propoxy]biphenyl-3-yl}methoxy)-2,3-dihydro-1-benzofuran-3-yl]acetic acid anhydride as crystals (C form crystal).

Reference Example 8

Synthesis of [(3S)-6-({2',6'-dimethyl-4'-[3-(methylsulfonyl)propoxy]biphenyl-3-yl}methoxy)-2,3-dihydro-1-benzofuran-3-yl]acetic acid anhydride crystal (A form crystal)

[(3S)-6-({2',6'-Dimethyl-4'-[3-(methylsulfonyl)propoxy] biphenyl-3-yl}methoxy)-2,3-dihydro-1-benzofuran-3-yl] acetic acid hydrate (0.5 hydrate) (100 mg) was dissolved in 2-propanol (2.5 mL) at 55° C. After filtration, n-heptane (2.5 mL) heated to 55° C. was added, and the mixture was allowed to gradually cool to 5° C. with stirring. The precipitated crystals were collected by filtration to give [(3S)-6-({2',6'-dimethyl-4'-[3-(methylsulfonyl)propoxy]biphenyl-3-yl}methoxy)-2,3-dihydro-1-benzofuran-3-yl]acetic acid anhydride as crystals (A form crystal) (about 60 mg).

Reference Example 9

Synthesis of methyl (6-hydroxy-1-benzofuran-3-yl)acetate

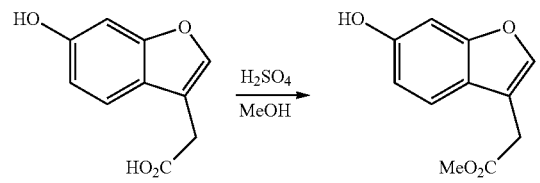

To a solution of (6-hydroxy-1-benzofuran-3-yl)acetic acid (20.0 g) in methanol (300 mL) was added concentrated sulfuric acid (7 mL), and the mixture was stirred at 60° C. for 4 hr. After concentration, to the residue were added ethyl acetate (400 mL) and saturated aqueous sodium hydrogen carbonate (400 mL), and an extraction operation was performed. The aqueous layer was extracted twice with ethyl acetate (200 mL), and the organic layer was washed with saturated brine (400 mL), dried over anhydrous sodium sulfate, and concentrated. The residue was dissolved in toluene (60 mL) at 60° C., allowed to cool to room temperature, and seed crystal was added. Normal heptane (120 mL) was added, and the mixture was stirred at room temperature for 16 hr and at 0° C. for 1 hr. The precipitated crystals were collected by filtration, and dried at 50° C. to give the title compound (19.6 g) as white crystals.

$^1$H NMR (500 MHz, CDCl$_3$): δ 3.68 (s, 2H), 3.74 (s, 3H), 5.17 (br s, 1H), 6.79 (dd, 1H), 6.94 (d, 1H), 7.37 (d, 1H), 7.52 (s, 1H).

Reference Example 10

Synthesis of [6-({2',6'-dimethyl-4'-[3-(methylsulfonyl)propoxy]biphenyl-3-yl}methoxy)-1-benzofuran-3-yl]acetic acid

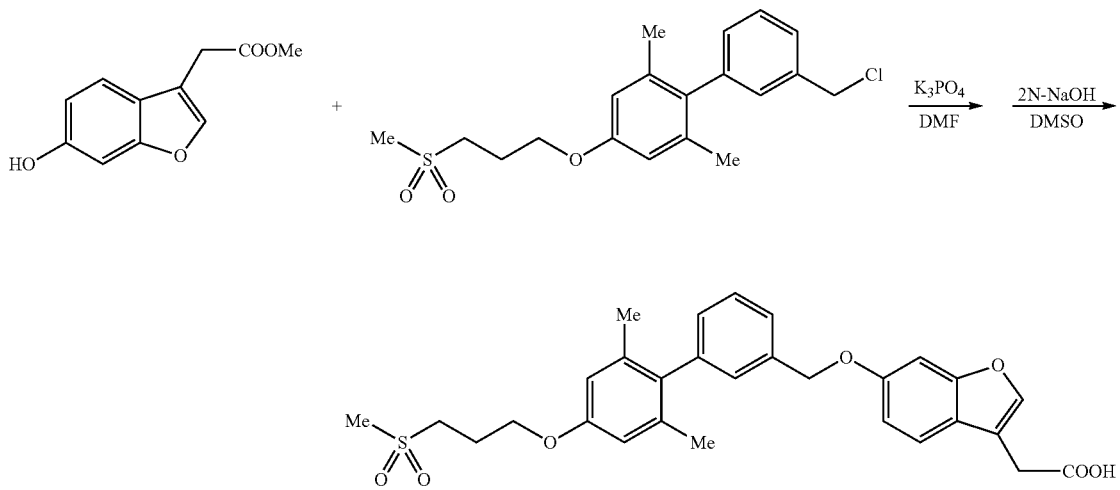

To a solution of methyl (6-hydroxy-1-benzofuran-3-yl)acetate (17.7 g) and 3'-(chloromethyl)-2,6-dimethyl-4-[3-(methylsulfonyl)propoxy]biphenyl (31.5 g) in N,N-dimethylformamide (60 mL) was added tripotassium phosphate (27.4 g), and the mixture was stirred at 70° C. for 3 hr. The mixture was allowed to cool to room temperature, toluene (240 mL) and water (240 mL) were added, and an extraction operation was performed. The aqueous phase was extracted with toluene (240 mL), and the extract was washed with water (240 mL) and saturated brine (240 mL), and concentrated. The obtained solid was dissolved in dimethyl sulfoxide (100 mL), and 2N sodium hydroxide (47.2 mL) was added at room temperature. After stirring at 70° C. for 1 hr and at 25° C. for 20 hr, the aqueous layer was acidified with 6N hydrochloric acid to pH 1-2, water (240 mL) and ethyl acetate (240 mL) were added, and an extraction operation was performed. The aqueous layer was extracted with ethyl acetate (200 mL), and the combined organic layer was washed with water (240 mL) and concentrated. The crude product was recrystallized from acetone (120 mL)-water (240 mL), and the obtained solid was dried at 60° C. under reduced pressure to give the title compound (34.1 g) as white crystals.

$^1$H NMR (500 MHz, DMSO-d$_6$): δ 1.92 (s, 6H), 2.05-2.21 (m, 2H), 3.03 (s, 3H), 3.18-3.30 (m, 2H), 3.63 (s, 2H), 4.00-4.15 (m, 2H), 5.20 (s, 2H), 6.71 (s, 2H), 6.96 (dd, 1H), 7.06 (d, 1H), 7.20-7.27 (m, 2H), 7.35-7.48 (m, 3H), 7.76 (s, 1H), 12.44 (br s, 1H).

Example 20

Synthesis of [(3S)-6-({2',6'-dimethyl-4'-[3-(methylsulfonyl)propoxy]biphenyl-3-yl}methoxy)-2,3-dihydro-1-benzofuran-3-yl]acetic acid

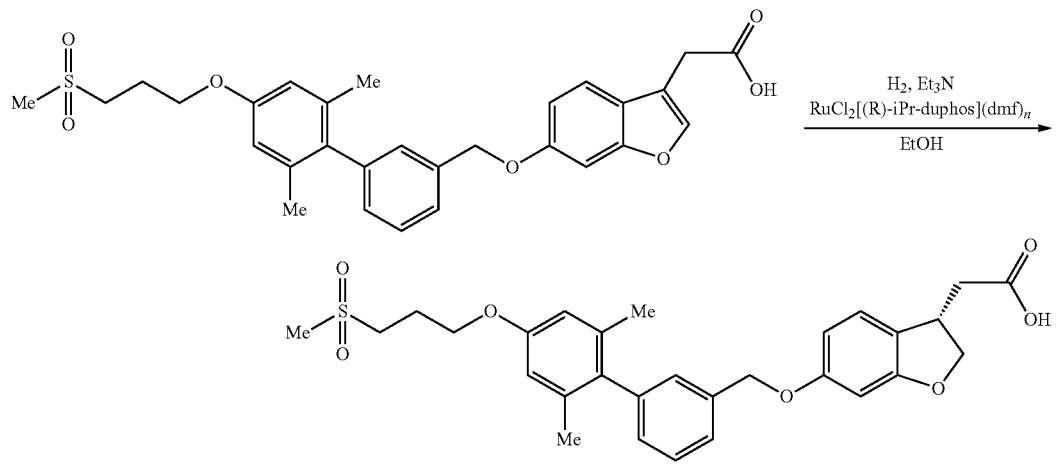

Under an argon atmosphere, to [6-({2',6'-dimethyl-4'-[3-(methylsulfonyl)propoxy]biphenyl-3-yl}methoxy)-1-benzofuran-3-yl]acetic acid (522 mg), dichloro[(+)-1,2-bis((2R,5R)-2,5-diisopropylphosphorano)benzene]ruthenium (II)-N,N-dimethylformamide complex (7.4 mg) in an autoclave container was added a solution of dehydrated ethanol (6 mL) containing triethylamine (0.139 mL), and the mixture was stirred at 50° C. for 24 hr under a hydrogen atmosphere (1 MPa). The reaction mixture was concentrated, 10% aqueous citric acid solution (25 mL) and ethyl acetate (25 mL) were added, and an extraction operation was performed. The aqueous layer was extracted with ethyl acetate (25 mL), and the combined organic layer was washed with water (25 mL), dried over sodium sulfate and concentrated. The crude product was washed with diisopropyl ether. After filtration, the obtained solid was dried at 50° C. under reduced pressure to give the title compound (523 mg) as white crystals. 80.0% ee.

$^1$H NMR (500 MHz, DMSO-$d_6$): δ 1.93 (s, 6H), 2.09-2.21 (m, 2H), 2.43-2.56 (m, 1H), 2.70 (dd, 1H, J=16.6, 5.5 Hz), 3.04 (s, 3H), 3.22-3.29 (m, 2H), 3.62-3.72 (m, 1H), 4.10 (t, 2H, J=6.1 Hz), 4.19 (dd, 1H, J=9.0, 6.8 Hz), 4.68 (t, 1H, J=9.0 Hz), 5.10 (s, 2H), 6.42-6.51 (m, 2H), 6.72 (s, 2H), 7.01-7.18 (m, 3H), 7.34-7.49 (m, 2H), 12.35 (br s, 1H).

(high performance liquid chromatography conditions)
column: CHIRALPAK AD-H (manufactured by DAICEL CHEMICAL INDUSTRIES, LTD.)
mobile phase: normal hexane/isopropylalcohol/trifluoroacetic acid (volume ratio: 50/50/0.1)
flow rate: 0.5 mL/min
detection: UV 220 nm
temperature: 30° C.

Example 21

The measurement results of powder X-ray diffraction of [(3S)-6-({2',6'-dimethyl-4'-[3-(methylsulfonyl)propoxy]biphenyl-3-yl}methoxy)-2,3-dihydro-1-benzofuran-3-yl]acetic acid anhydride crystals (C form crystal) are shown in the following Table.

TABLE 1

| 2θ (°) | d value (Å) | relative intensity (%) |
|---|---|---|
| 4.59 | 19.2356 | 10 |
| 4.7 | 18.7856 | 21 |

TABLE 1-continued

| 2θ (°) | d value (Å) | relative intensity (%) |
|---|---|---|
| 11.56 | 7.6486 | 14 |
| 13.94 | 6.3476 | 17 |
| 15.42 | 5.7415 | 20 |
| 16.5 | 5.3681 | 100 |
| 17.15 | 5.1661 | 21 |
| 18.05 | 4.9105 | 19 |
| 18.37 | 4.8256 | 16 |
| 18.42 | 4.8126 | 22 |
| 18.79 | 4.7187 | 30 |
| 18.89 | 4.694 | 28 |
| 19.45 | 4.56 | 43 |
| 19.77 | 4.487 | 70 |
| 19.9 | 4.4579 | 18 |
| 20.01 | 4.4337 | 30 |
| 20.07 | 4.4206 | 24 |
| 20.51 | 4.3267 | 18 |
| 20.7 | 4.2874 | 37 |
| 21.53 | 4.124 | 49 |
| 21.62 | 4.107 | 34 |
| 22.59 | 3.9328 | 30 |
| 23.17 | 3.8357 | 57 |
| 23.37 | 3.8033 | 44 |
| 23.6 | 3.7667 | 20 |
| 23.75 | 3.7433 | 56 |

Reference Example 11

The measurement results of powder X-ray diffraction of [(3S)-6-({2',6'-dimethyl-4'-[3-(methylsulfonyl)propoxy]biphenyl-3-yl}methoxy)-2,3-dihydro-1-benzofuran-3-yl]acetic acid anhydride crystals (A form crystal) are shown in the following Table.

TABLE 2

| 2θ (°) | d value (Å) | relative intensity (%) |
|---|---|---|
| 4.32 | 20.4372 | 7 |
| 4.7 | 18.7856 | 27 |

TABLE 2-continued

| 2θ (°) | d value (Å) | relative intensity (%) |
|---|---|---|
| 11.24 | 7.8656 | 11 |
| 11.74 | 7.5317 | 11 |
| 12.7 | 6.9645 | 13 |
| 14.82 | 5.9726 | 11 |
| 15.02 | 5.8935 | 21 |
| 15.52 | 5.7048 | 23 |
| 17.14 | 5.1691 | 25 |
| 17.5 | 5.0635 | 46 |
| 17.68 | 5.0124 | 46 |
| 18.9 | 4.6915 | 100 |
| 19.52 | 4.5439 | 19 |
| 20.44 | 4.3414 | 47 |
| 20.92 | 4.2428 | 12 |
| 21.26 | 4.1757 | 37 |
| 22.16 | 4.0081 | 17 |
| 22.54 | 3.9414 | 66 |
| 23 | 3.8636 | 53 |
| 23.4 | 3.7985 | 10 |
| 23.62 | 3.7636 | 12 |
| 24.34 | 3.6539 | 14 |
| 26.78 | 3.3262 | 14 |
| 27.9 | 3.1952 | 10 |

Reference Example 12

The measurement results of powder X-ray diffraction of [(3S)-6-({2',6'-dimethyl-4'-[3-(methylsulfonyl)propoxy]biphenyl-3-yl}methoxy)-2,3-dihydro-1-benzofuran-3-yl]acetic acid hydrate crystals are shown in the following Table.

TABLE 3

| 2θ (°) | d value (Å) | relative intensity (%) |
|---|---|---|
| 4.85 | 18.205 | 27 |
| 7.26 | 12.1662 | 17 |
| 11.63 | 7.6027 | 11 |
| 12.08 | 7.3205 | 30 |
| 15.49 | 5.7158 | 23 |
| 15.6 | 5.6757 | 42 |
| 15.75 | 5.622 | 100 |
| 17.6 | 5.035 | 15 |
| 18.02 | 4.9186 | 19 |
| 18.17 | 4.8783 | 11 |
| 19.02 | 4.6622 | 29 |
| 19.35 | 4.5834 | 46 |
| 19.75 | 4.4915 | 14 |
| 20.86 | 4.2549 | 20 |
| 20.97 | 4.2328 | 64 |
| 21.31 | 4.166 | 16 |
| 21.52 | 4.1259 | 23 |
| 21.82 | 4.0698 | 13 |
| 22.09 | 4.0207 | 27 |
| 22.48 | 3.9518 | 17 |
| 22.98 | 3.8669 | 27 |
| 23.12 | 3.8438 | 60 |
| 23.36 | 3.8049 | 57 |
| 23.6 | 3.7667 | 17 |
| 24.11 | 3.6882 | 32 |
| 26.36 | 3.3783 | 15 |

Reference Example 13

Synthesis of 3-(methylsulfonyl)propyl 4-methylbenzenesunfonate

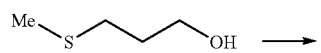

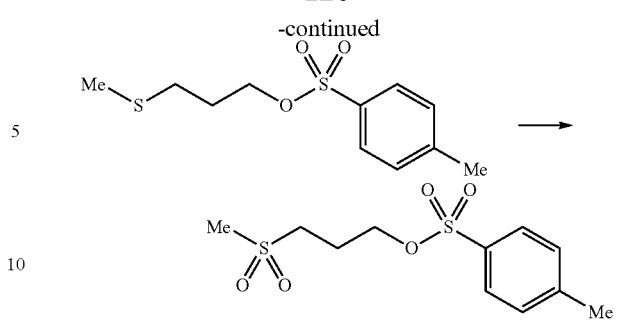

3-Methylthiopropanol (100 g), triethylamine (143 g) and N,N,N',N'-tetramethyl-1,6-diaminohexane (16 g) were dissolved in toluene (1000 mL), tosyl chloride (179.5 g) dissolved in toluene (660 mL) was added dropwise, and the mixture was stirred at 3° C. for 3 hr. After the reaction, water was added, and the mixture was left standing and partitioned. To the organic layer was added dropwise oxone (registered trade mark; 868 g) dissolved in water, and the mixture was stirred at room temperature for about 5 hr. Water was added, and the precipitated solid was collected by filtration, and washed with water. The solid was dried under reduced pressure to give white title compound (221.1 g).

Example 22

Synthesis of 2',6'-dimethyl-4'-[3-(methylsulfonyl)propoxy]biphenyl-3-carbaldehyde

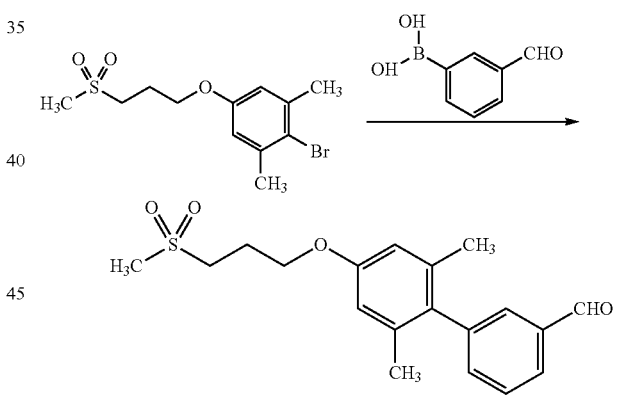

2-Bromo-1,3-dimethyl-5-[3-(methylsulfonyl)propoxy]benzene (100 g), 3-formylphenylboronic acid (56 g), 10% palladium carbon 50% water-containing product (10 g) and 2,2'-bis(diphenylphosphino)-1,1'-binaphthyl (4 g) were added to dimethyl sulfoxide (1000 mL). Tripotassium phosphate (132 g) dissolved in water (500 mL) was added, and the mixture was stirred at 80° C. for 1 hr. The reaction mixture was left standing, an oil component was removed, and ethyl acetate was added. The insoluble material was removed by filtration, and washed with ethyl acetate. The filtrate was washed with 10% brine, and the organic layer was concentrated. Ethyl acetate was added, and the mixture was azeotropically distilled with dehydration. To the concentrate were added ethyl acetate and activated carbon (10 g), and the mixture was stirred at 45° C. The insoluble material was removed by filtration, and washed with ethyl acetate. The filtrate was concentrated under reduced pressure, and isopropyl alcohol was added dropwise. The precipitated solid was collected by filtration, and the solid was washed with isopropyl alcohol, and dried under reduced pressure to give 2',6'-dimethyl-4'-[3-(methylsulfonyl)propoxy]biphenyl-3-carbaldehyde (92.8 g).

Example 23

Synthesis of methyl [(3S)-6-({2',6'-dimethyl-4'-[3-(methylsulfonyl)propoxy]biphenyl-3-yl}methoxy)-2,3-dihydro-1-benzofuran-3-yl]acetate

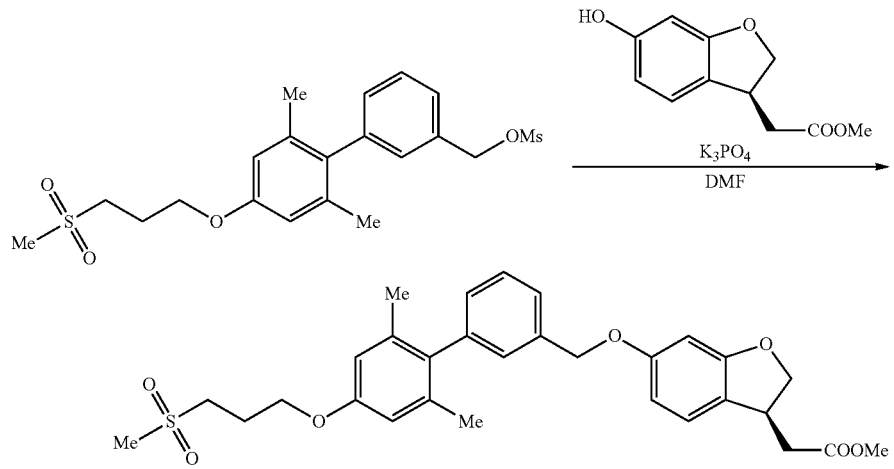

{2',6'-Dimethyl-4'-[(3-methylsulfonyl)propoxy]biphenyl-3-yl}methyl methanesulfonate (0.512 g, 1.20 mmol), methyl [(3S)-6-hydroxy-2,3-dihydro-1-benzofuran-3-yl]acetate (0.237 g, 1.14 mmol), tripotassium phosphate (0.255 g, 1.20 mmol) and N,N-dimethylformamide (1.25 ml) were charged, and the mixture was stirred at 60° C. for 1 hr. The obtained reaction mixture was is analyzed by high performance liquid chromatography to find the title compound (31.9% peak area).
(high performance liquid chromatography conditions)
column: YMC ODS A-302 (4.6 mm×150 mm)
mobile phase: 50 mM potassium dihydrogen phosphate/acetonitrile (volume ratio:4/6)
flow rate: 1.0 mL/min
detection: UV 220 nm
temperature: 25° C.

Example 24

Synthesis of [6-({2',6'-dimethyl-4'-[3-(methylsulfonyl)propoxy]biphenyl-3-yl}methoxy)-1-benzofuran-3-yl]acetic acid To a solution of methyl(S)-2-(6-(((trifluoromethyl)sulfonyl)oxy)-2,3-dihydrobenzofuran-3-yl)acetate (4.88 g) and (2',6'-dimethyl-4'-(3-(methylsulfonyl)propoxy)-[1,1'-biphenyl]-3-yl)methanol (5.00 g) in N,N-dimethylformamide (15 mL) was added tripotassium phosphate (4.57 g), and the mixture was stirred at 70° C. for 3 hr. The mixture was allowed to cool to room temperature, toluene (60 mL) and water (60 mL) were added, and an extraction operation was performed. The organic layer was washed with water (60 mL) and 10% brine (60 mL), and concentrated. The obtained oil was dissolved in dimethyl sulfoxide (30 mL), and 2N sodium hydroxide (8 mL) was added at room temperature. The mixture was stirred at 70° C. for 1 hr, and allowed to cool to room temperature. Ethyl acetate (60 mL) and water (60 mL) were added, and the mixture was partitioned. The aqueous layer was acidified with 6N hydrochloric acid to pH 1, ethyl acetate (60 mL) was added, and an extraction operation was performed. The organic layer was washed with water (60 mL), and concentrated. The crude product was recrystallized from acetone (30 mL)-water (60 mL), and the obtained solid was dried at 60° C. under reduced pressure to give the title compound (4.91 g) as white crystals. Yield 65%.

Example 25

Synthesis of [6-({2',6'-dimethyl-4'-[3-(methylsulfonyl)propoxy]biphenyl-3-yl}methoxy)-1-benzofuran-3-yl]acetic acid To a solution of methyl(S)-2-(6-(((trifluoromethyl)sulfonyl)oxy)-2,3-dihydrobenzofuran-3-yl)acetate (4.88 g) and (2',6'-dimethyl-4'-(3-(methylsulfonyl)propoxy)-[1,1'-biphenyl]-3-yl)methanol (5.00 g) in acetonitrile (15 mL) was added tripotassium phosphate (4.57 g), and the mixture was stirred at 70° C. for 3 hr. The mixture was allowed to cool to room temperature and concentrated, toluene (60 mL) and water (60 mL) were added, and an extraction operation was performed. The organic layer was washed with water (60 mL) and 10% brine (60 mL), and concentrated. The obtained oil was dissolved in dimethyl sulfoxide (30 mL), and 2N sodium hydroxide (8 mL) was added at room temperature. The mixture was stirred at 70° C. for 1 hr, and allowed to cool to room temperature. Ethyl acetate (60 mL) and water (60 mL) were added, and the mixture was partitioned. The aqueous layer was acidified with 6N hydrochloric acid to pH 1, ethyl acetate (60 mL) was added, and an extraction operation was performed. The organic layer was washed with water (60 mL), and concentrated. The crude product was recrystallized from acetone (30 mL)-water (60 mL), and the obtained solid was dried at 60° C. under reduced pressure to give the title compound (4.82 g) as white crystals. Yield 64%.

Example 26

Synthesis of [6-({2',6'-dimethyl-4'-[3-(methylsulfonyl)propoxy]biphenyl-3-yl}methoxy)-1-benzofuran-3-yl]acetic acid A solution of tris(dibenzylideneacetone)dipalladium (0). dibenzylideneacetone solvate (42.5 mg) and 2-(dicyclohexylphosphino-2',4',6'-triisopropyl-1,1'-biphenyl) (76.18 mg) in toluene (4 ml) and 1,2-dimethoxyethane (4 ml) was stirred at 70° C. for 1 hr. After allowing to cool to room temperature, methyl(S)-2-(6-(((trifluoromethyl)sulfonyl)oxy)-2,3-dihydrobenzofuran-3-yl)acetate (864.3 mg), (2',6'-dimethyl-4'-(3-(methylsulfonyl)propoxy)-[1,1'-biphenyl]-3-yl)methanol (1.15 g) and cesium carbonate (2.60 g) were added, and the mixture was stirred at 85° C. for 6 hr. The mixture was allowed to cool to room temperature and concentrated, toluene (30 mL) and water (30 mL) were added, and an extraction operation was performed. The organic layer was washed with water (30 mL) and 10% brine (30 mL), and concentrated. The obtained oil was dissolved in dimethyl sulfoxide (15 mL), and 2N sodium hydroxide (4 mL) was added at room temperature. The mixture was stirred at 70° C. for 1 hr, and allowed to cool to room temperature. Ethyl acetate (30 mL) and water (30 mL) were added, and the mixture was partitioned. The aqueous layer was acidified with 6N hydrochloric acid to pH 1, ethyl acetate (30 mL) was added, and an extraction operation was performed. The organic layer was washed with water (30 mL), and concentrated. The crude product was recrystallized from acetone (15 mL)-water (30 mL), and the obtained solid was dried at 60° C. under reduced pressure to give the title compound (706 mg) as white crystals. Yield 53%.

Example 27

Synthesis of [(3S)-6-hydroxy-2,3-dihydro-1-benzofuran-3-yl]acetic acid

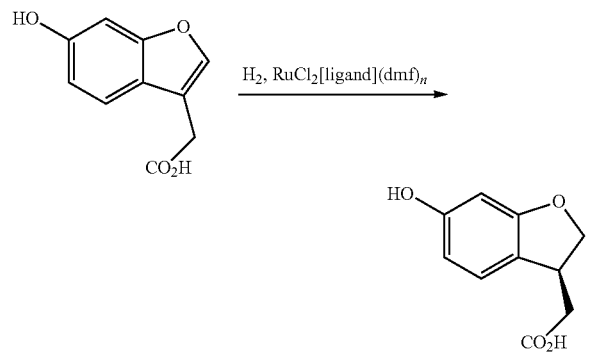

(6-Hydroxy-1-benzofuran-3-yl)acetic acid (0.050 g, 0.26 mmol) and dichloro[(+)-1,2-bis((2R,5R)-2,5-diisopropylphosphorano)benzene]ruthenium (II)-N,N-dimethylformamide complex (1.9 mg, 0.0026 mmol) and sodium methoxide (14.0 mg, 0.26 mmol) were charged, and purged with argon. Methanol (1 mL) was added thereto, and the mixture was stirred at room temperature for 12 hr under a hydrogen atmosphere (1.0 MPa). The obtained reaction mixture was analyzed by liquid chromatography to give the title compound (conversion ratio 99.9%, optical purity 84.1% ee(S)).
(high performance liquid chromatography conditions)
column: CHIRALPAK AD-H (manufactured by DAICEL CHEMICAL INDUSTRIES, LTD.)
mobile phase: normal hexane/ethanol/trifluoroacetic acid (volume ratio: 90/10/0.1)
flow rate: 1.0 mL/min
detection: UV 220 nm
temperature: 25° C.

Examples 28-37

The reaction was performed according to the method of Example 27. The results are shown in Table 4.
A ruthenium complex to be the catalyst was prepared according to the method of Example 1.

TABLE 4

| Ex. | ligand | solvent | base | Conv., % | ee, % | absolute configuration |
|---|---|---|---|---|---|---|
| 28 | (S)-Me-DuPHOS | methanol | KO$^t$Bu | 73.4 | 53.6 | S |
| 29 | (S)-Me-DuPHOS | methanol | NaOMe | 99.9 | 65.0 | S |
| 30 | (S)-Et-DuPHOS | methanol | NaOMe | 99.9 | 66.6 | S |
| 31 | (S)-$^i$Pr-DuPHOS | methanol | NaOMe | 99.9 | 83.8 | R |
| 32 | (S)-Me-BPE | methanol | NaOMe | 100.0 | 53.6 | S |
| 33 | (S)-Ph-BPE | methanol | NaOMe | 99.8 | 18.4 | R |
| 34 | (S)-MeO-BIPHEP | methanol | NaOMe | 99.5 | 22.3 | S |
| 35 | (S)-SKEWPHOS | methanol | NaOMe | 29.7 | 5.1 | R |
| 36 | (S)-Me-Bophoz | methanol | NaOMe | 13.6 | 13.6 | R |
| 37 | (R)-$^i$Pr-DuPHOS | methanol | K$_3$PO$_4$ | 99.9 | 77.4 | S |

(S)-Me-DuPHOS: 1,2-bis[(2S,5S)-2,5-dimethylphosphorano]benzene
(S)-Et-DuPHOS: 1,2-bis[(2S,5S)-2,5-diethylphosphorano]benzene
(S)-$^i$Pr-DuPHOS: 1,2-bis[(2S,5S)-2,5-diisopropylphosphorano]benzene
(S)-Me-BPE: 1,2-bis[(2S,5S)-2,5-dimethylphosphorano]ethane
(S)-Ph-BPE: 1,2-bis[(2S,5S)-2,5-diphenylphosphorano]ethane
(S)-MeO-BIPHEP: (S)-2,2'-bis-(diphenylphosphino)-6,6'-dimethoxy-1,1'-biphenyl
(S)-SKEWPHOS: (2S,4S)-2,4-bis(diphenylphosphino)pentane
(S)-Me-Bophoz: (S)-N-methyl-N-diphenylphosphino-1-[(R)-2-(diphenylphosphino)ferrocenyl]ethylamine
(R)-$^i$Pr-DuPHOS: 1,2-bis[(2R,5R)-2,5-diisopropylphosphorano]benzene

Example 38

Synthesis of [(3S)-6-hydroxy-2,3-dihydro-1-benzofuran-3-yl]acetic acid (S)-2-amino-1,1-diphenylpropan-1-ol salt A racemate (0.05 g) of (6-hydroxy-2,3-dihydro-1-benzofuran-3-yl)acetic acid was charged, a mixed solvent of methanol/isopropyl alcohol (1/4) was added, and the racemate was dissolved. (S)-2-Amino-1,1-diphenylpropan-1-ol (0.059 g, 1 eq) was added thereto, and the mixture was stirred at room temperature for 12 hr. The precipitated crystals were collected by filtration to give the title compound (0.037 g). 87.8% de
(high performance liquid chromatography conditions)
column: CHIRALPAK AD-H (manufactured by DAICEL CHEMICAL INDUSTRIES, LTD.)
mobile phase: normal hexane/ethanol/trifluoroacetic acid (volume ratio: 90/10/0.1)
flow rate: 1.0 mL/min
detection: UV 220 nm
temperature: 25° C.

Examples 39-60

According to the method of Example 38, diastereomer salts were synthesized. The results are shown in Table 5.

TABLE 5

| Ex. | optically active amine | solvent | solvent amount, x fold | yield, % | de, % |
|---|---|---|---|---|---|
| 39 | Amine-1 | ethanol | 20 | 7.7 | 87.5 |
| 40 | Amine-2 | ethanol | 40 | 12.8 | 40.4 |
| 41 | Amine-3 | isopropanol | 50 | 39 | 17.5 |
| 42 | Amine-4 | ethanol | 30 | 35.2 | 58.6 |
| 43 | Amine-4 | isopropanol | 50 | 50 | 35.5 |
| 44 | Amine-4 | acetone | 20 | 39.1 | 63.1 |
| 45 | Amine-4 | methanol/acetonitrile (1/2) | 30 | 44.4 | 51.5 |
| 46 | Amine-4 | methanol/ethyl acetate (1/2) | 30 | 35.1 | 64.1 |
| 47 | Amine-4 | methanol/isopropanol (1/4) | 30 | 42.1 | 46.8 |
| 48 | Amine-4 | isopropanol/acetone (1/1) | 20 | 34.2 | 59.3 |
| 49 | Amine-4 | ethanol/acetonitrile (1/1) | 20 | 25 | 75.9 |
| 50 | Amine-4 | acetonitrile/acetone (1/4) | 30 | 32.9 | 72.3 |
| 51 | Amine-5 | ethanol | 30 | 11.6 | 90.5 |
| 52 | Amine-5 | ethyl acetate | 50 | 27.8 | 90.4 |
| 53 | Amine-5 | water/isopropanol (1/4) | 20 | 14.8 | 93.5 |
| 54 | Amine-5 | ethanol/ethyl acetate (1/1) | 30 | 20.1 | 93 |
| 55 | Amine-5 | methanol/acetonitrile (1/4) | 30 | 30.1 | 91.2 |
| 56 | Amine-5 | methanol/ethyl acetate (1/4) | 30 | 28.8 | 90.1 |
| 57 | Amine-6 | ethanol | 30 | 26 | 19.8 |
| 58 | Amine-6 | isopropanol | 50 | 29 | 32.4 |
| 59 | Amine-6 | tetrahydrofuran | 30 | 45.2 | 26.3 |
| 60 | Amine-6 | ethyl acetate | 50 | 67.6 | 12.4 |

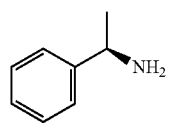

Amine-1

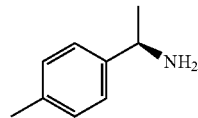

Amine-2

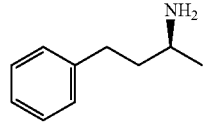

Amine-3

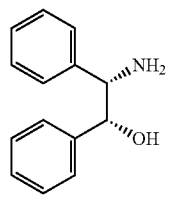

Amine-4

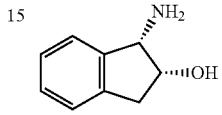

Amine-5

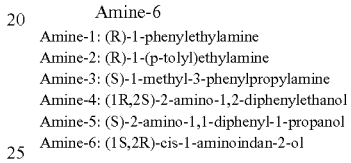

Amine-6

Amine-1: (R)-1-phenylethylamine
Amine-2: (R)-1-(p-tolyl)ethylamine
Amine-3: (S)-1-methyl-3-phenylpropylamine
Amine-4: (1R,2S)-2-amino-1,2-diphenylethanol
Amine-5: (S)-2-amino-1,1-diphenyl-1-propanol
Amine-6: (1S,2R)-cis-1-aminoindan-2-ol Example 61

Synthesis of [(3S)-6-hydroxy-2,3-dihydro-1-benzofuran-3-yl]acetic acid (R)-1-phenylpropylamine salt A racemate (19 mg, 0.1 mmol) of (6-hydroxy-2,3-dihydro-1-benzofuran-3-yl)acetic acid was charged, methanol was added, and the racemate was dissolved. The solution and ((R)-1-phenylpropylamine (13.5 mg, 0.1 mmol) were mixed and stood. The precipitated crystals were collected by filtration to give the title compound. 5.1% de
(high performance liquid chromatography conditions)
column: CHIRALPAK AD-H (manufactured by DAICEL CHEMICAL INDUSTRIES, LTD.)
mobile phase: normal hexane/ethanol/trifluoroacetic acid (volume ratio: 90/10/0.1)
flow rate: 1.0 mL/min
detection: UV 220 nm
temperature: 25° C.

Example 62

Synthesis of [(3S)-6-hydroxy-2,3-dihydro-1-benzofuran-3-yl]acetic acid (R)-α,α-diphenyl-2-pyrrolidinemethanol salt A racemate (19 mg, 0.1 mmol) of (6-hydroxy-2,3-dihydro-1-benzofuran-3-yl)acetic acid was charged, methanol was added, and the racemate was dissolved. This solution and (R)-α,α-diphenyl-2-pyrrolidinemethanol (25.3 mg, 0.1 mmol) were mixed and stood. The precipitated crystals were collected by filtration to give the title compound. 9.9% de
(high performance liquid chromatography conditions)
column: CHIRALPAK AD-H (manufactured by DAICEL CHEMICAL INDUSTRIES, LTD.)
mobile phase: normal hexane/ethanol/trifluoroacetic acid (volume ratio: 90/10/0.1)
flow rate: 1.0 mL/min
detection: UV 220 nm
temperature: 25° C.

Example 63

Synthesis of 2',6'-dimethyl-4'-[3-(methylsulfonyl)propoxy]biphenyl-3-carbaldehyde

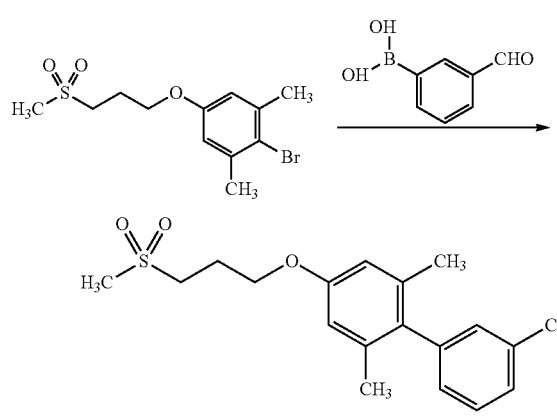

2-Bromo-1,3-dimethyl-5-[3-(methylsulfonyl)propoxy]benzene (0.10 g), 3-formylphenylboronic acid (0.05 g, 1.05 eq), potassium phosphate (0.13 g, 2.0 eq) and 1,1'-bis(diphenylphosphino)ferrocene-palladium (II) dichloride-dichloromethane complex (PdCl$_2$(dppf)) (5 mg, 2 mol %) were charged in a glass tube, and N,N-dimethylformamide (1 mL) and water (0.5 mL) were added thereto. After argon substitution, the mixture was stirred at 60° C. for 3 hr. The obtained reaction mixture was analyzed by high performance liquid chromatography to find the title compound (81.8% peak area).

(high performance liquid chromatography conditions)

column: YMC ODS A302 (4.6 mm×150 mm)

mobile phase: 25 mM potassium dihydrogen phosphate/acetonitrile (volume ratio: 50/50)

flow rate: 1.0 mL/min detection: UV 220 nm temperature: 25° C.

Examples 64-70

The reaction was performed according to the method of Example 63. The results are shown in Table 6.

TABLE 6

| Example | palladium catalyst | base | solvent | title compound area percentage (%) |
|---|---|---|---|---|
| 64 | PdCl$_2$(dppf) | K$_3$PO$_4$ | DMAc | 82.0 |
| 65 | PdCl$_2$(dppf) | LiOH | DMF | 79.2 |
| 66 | PdCl$_2$(dppf) | LiOH | DMAc | 84.2 |
| 67 | PdCl$_2$(dppf) | NaOH | DMF | 70.8 |
| 68 | Pd(PPh$_3$)$_4$ | K$_3$PO$_4$ | THF | 51.2 |
| 69 | Pd(PPh$_3$)$_4$ | LiOH | THF | 53.7 |
| 70 | Pd(PPh$_3$)$_4$ | NaOH | THF | 62.5 |

PdCl$_2$(dppf): dichloro(1,1'-bis(diphenylphosphino)ferrocene)palladium (II)
Pd(PPh$_3$)$_4$: tetrakis(triphenylphosphine)palladium (0)

Example 71

Synthesis of 2',6'-dimethyl-4'-[3-(methylsulfonyl)propoxy]biphenyl-3-carbaldehyde

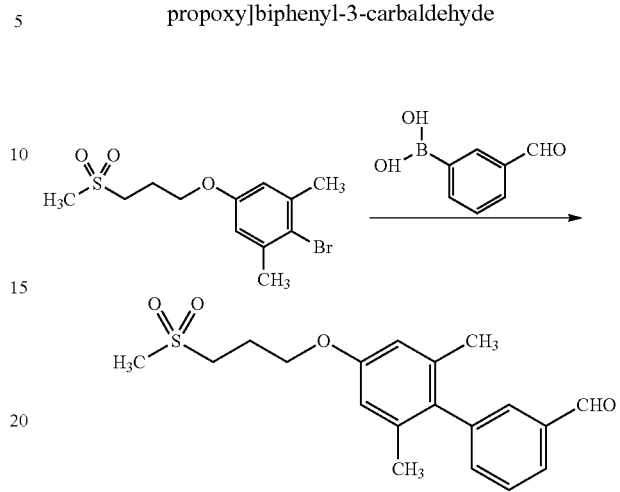

2-Bromo-1,3-dimethyl-5-[3-(methylsulfonyl)propoxy]benzene (0.10 g), 3-formylphenylboronic acid (0.05 g, 1.05 eq), lithium chloride (0.026 g, 2.0 eq), palladium acetate (1.4 mg, 2 mol %) and tri-tert-butylphosphonium tetrafluoroborate (1.8 mg, 2 mol %) were charged in a glass tube, and tetrahydrofuran (1 mL) and water (0.5 mL) were added thereto. After argon substitution, the mixture was stirred at 60° C. for 3 hr. The obtained reaction mixture was analyzed by high performance liquid chromatography to find the title compound (82.9% peak area).

(high performance liquid chromatography conditions)

column: YMC ODS A302 (4.6 mm×150 mm)

mobile phase: 25 mM potassium dihydrogen phosphate/acetonitrile (volume ratio: 50/50)

flow rate: 1.0 mL/min detection: UV 220 nm temperature: 25° C.

Examples 72-74

The reaction was performed according to the method of Example 71. The results are shown in Table 7.

TABLE 7

| Ex. | palladium source | ligand | base | solvent | title compound area percentage (%) |
|---|---|---|---|---|---|
| 72 | Pd(OAc)$_2$ | P$^t$Bu$_3$HBF$_4$ | NaOH | DMAc | 66.6 |
| 73 | Pd(OAc)$_2$ | P$^t$Bu$_2$MeHBF$_4$ | LiOH | THF | 60.6 |
| 74 | Pd(OAc)$_2$ | P$^t$Bu$_2$MeHBF$_4$ | NaOH | DMF | 56.6 |

Pd(OAc)$_2$: palladium acetate
P$^t$Bu$_3$HBF$_4$: tri-tert-butylphosphonium tetrafluoroborate
P$^t$Bu$_2$MeHBF$_4$: di-tert-butyl(methyl)phosphonium tetrafluoroborate

Examples 75-81

The reaction was performed according to the method of Example 71. The results are shown in Table 8.

TABLE 8

| Ex. | palladium source | ligand | base | solvent | title compound area percentage (%) |
|---|---|---|---|---|---|
| 75 | Pd(OAc)$_2$ | cataCXium PInCy | LiOH | THF | 78.7 |
| 76 | Pd(OAc)$_2$ | cataCXium ABn | LiOH | DMAc | 59.6 |
| 77 | Pd(OAc)$_2$ | cataCXium POMetB | LiOH | DMAc | 79.2 |
| 78 | Pd(OAc)$_2$ | cataCXium POMeCy | LiOH | DMAc | 88.5 |
| 79 | Pd(OAc)$_2$ | cataCXium PIntB | LiOH | DMAc | 89.4 |
| 80 | Pd(OAc)$_2$ | cataCXium PtB | LiOH | DMAc | 86.9 |
| 81 | Pd(OAc)$_2$ | cataCXium PCy | LiOH | DMAc | 80.6 |

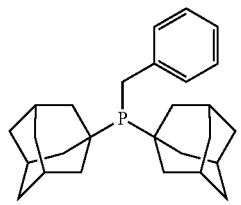

cataCXium ABn

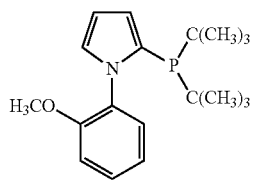

cataCXium POMetB

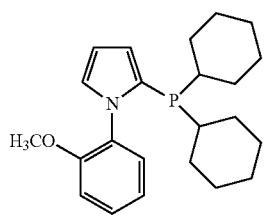

cataCXium POMeCy

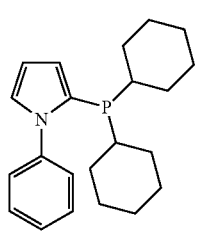

cataCXium PCy

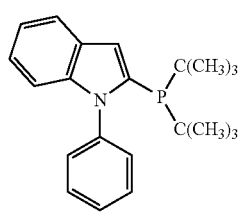

cataCXium PIntB cataCXium PInCy cataCXium PtB cataCXium ABn: benzyl-di-1-adamantylphosphine cataCXium POMetB: 1-(2-methoxyphenyl)-2-(di-tert-butylphosphino)-1H-pyrrole cataCXium POMeCy: 1-(2-methoxyphenyl)-2-(dicyclohexylphosphino)-1H-pyrrole cataCXium PCy: 1-phenyl-2-(dicyclohexylphosphino)-1H-pyrrole cataCXium PIntB: 1-phenyl-2-(di-tert-butylphosphino)-1H-indole cataCXium PInCy: 1-phenyl-2-(dicyclohexylphosphino)-1H-indole cataCXium PtB: 1-phenyl-2-(di-tert-buylphosphino)-1H-pyrrole

Examples 82-89

The reaction was performed according to the method of Example 71. The results are shown in Table 9.

TABLE 9

| Example | palladium source | ligand | base | solvent | title compound area percentage (%) |
|---|---|---|---|---|---|
| 82 | Pd(OAc)$_2$ | La1 | LiOH | DMAc | 91.3 |
| 83 | Pd(OAc)$_2$ | La2 | LiOH | DMAc | 100 |
| 84 | Pd(OAc)$_2$ | La3 | LiOH | DMAc | 100 |
| 85 | Pd(OAc)$_2$ | La4 | LiOH | DMAc | 96.3 |
| 86 | Pd(OAc)$_2$ | La5 | LiOH | DMAc | 91.7 |
| 87 | Pd(OAc)$_2$ | La6 | LiOH | DMAc | 88.1 |
| 88 | Pd(OAc)$_2$ | La7 | LiOH | DMAc | 90.9 |
| 89 | Pd(OAc)$_2$ | La8 | LiOH | DMAc | 76.7 |

La1: sodium 2'-(dicyclohexylphosphino)-2,6-dimethoxybiphenyl-3-sulfonate

La2: 2-(dicyclohexylphosphino)-2',6'-dimethoxybiphenyl

La3: 2-(dicyclohexylphosphino)-2'-(N,N-dimethylamino)biphenyl

La4: 2-(dicyclohexylphosphino)-2',6'-diisopropoxybiphenyl

La5: 2-(dicyclohexylphosphino)-2'-methylbiphenyl

La6: 2-(dicyclohexylphosphino)-2',4',6'-triisopropylbiphenyl

La7: 2-(dicyclohexylphosphino)biphenyl

La8: 2-(diphenylphosphino)-2'-(N,N-dimethylamino)biphenyl

Example 90

Synthesis of 2',6'-dimethyl-4'-[3-(methylsulfonyl)propoxy]biphenyl-3-carbaldehyde

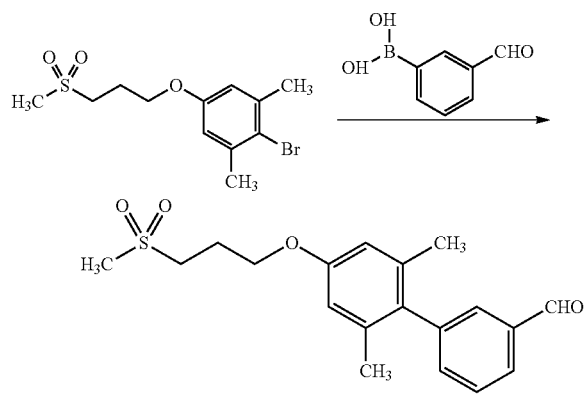

2-Bromo-1,3-dimethyl-5-[3-(methylsulfonyl)propoxy]benzene (1.0 g), 3-formylphenylboronic acid (0.49 g, 1.05 eq), LiOH.H$_2$O (0.26 g, 2.0 eq), palladium chloride (11 mg, 2 mol %) and 2-(dicyclohexylphosphino)biphenyl (44 mg, 4 mol %) were charged in a reaction container, and N,N-dimethylacetamide (10 mL) and water (5 mL) were added thereto. After nitrogen substitution, the mixture was stirred at 60° C. for 3 hr. The obtained reaction mixture was analyzed by high performance liquid chromatography to find the title compound (94.0% peak area).
(high performance liquid chromatography conditions)
column: YMC ODS A302 (4.6 mm×150 mm)
mobile phase: 25 mM potassium dihydrogen phosphate/acetonitrile (volume ratio: 50/50)
flow rate: 1.0 mL/min
detection: UV 220 nm
temperature: 25° C.

Examples 91-100

The reaction was performed according to the method of Example 90. The results are shown in Table 10.

TABLE 10

| Ex. | palladium source | ligand | title compound area percentage (%) |
|---|---|---|---|
| 91 | PdCl$_2$ | P$^t$Bu$_3$ | 69.5 |
| 92 | PdCl$_2$ | P$^n$Bu$_3$ | 23.6 |
| 93 | PdCl$_2$ | PCy$_3$ | 79.4 |
| 94 | PdCl$_2$ | DPPE | 27.5 |
| 95 | Pd(OAc)$_2$ | 2-(dicyclohexylphosphino)-biphenyl | 89.6 |
| 96 | Pd(OAc)$_2$ | P(o-tol)$_3$ | 64.5 |
| 97 | Pd(OAc)$_2$ | DPPE | 33.6 |
| 98 | Pd(OAc)$_2$ | rac-BINAP | 30.8 |
| 99 | Pd(OAc)$_2$ | P$^t$Bu$_3$ | 72.1 |
| 100 | Pd(OAc)$_2$ | PCy$_3$ | 68.2 |

PdCl$_2$: palladium chloride
Pd(OAc)$_2$: palladium acetate
rac-BINAP: racemate of 2,2'-bis(diphenylphosphino)-1,1'-binaphthyl
DPPE: 1,2-bis(diphenylphosphino)ethane
P(o-tol)$_3$: tri(o-tolyl)phosphine
PCy$_3$: tricyclohexylphosphine
P$^t$Bu$_3$: tri-tert-butylphosphine
P$^n$Bu$_3$: tri-n-butylphosphine

Example 101

Synthesis of 2',6'-dimethyl-4'-[3-(methylsulfonyl)propoxy]biphenyl-3-carbaldehyde

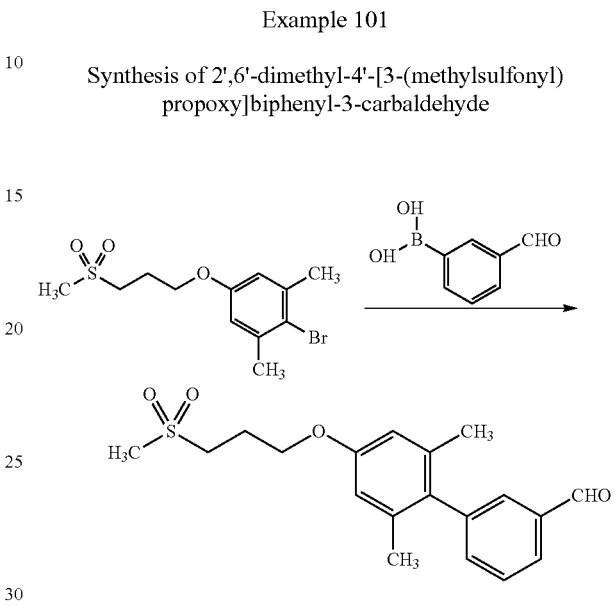

2-Bromo-1,3-dimethyl-5-[3-(methylsulfonyl)propoxy]benzene (1.0 g), 3-formylphenylboronic acid (0.49 g, 1.05 eq), tripotassium phosphate (1.32 g, 2.0 eq), 10% Pd—C(PE) (0.1 g, 1.38 mol %), rac-BINAP (26.8 mg, 1.38 mol %), dimethyl sulfoxide (10 mL) and water (5 mL) were added. After nitrogen substitution, the mixture was stirred at 80° C. for 3 hr. The obtained reaction mixture was analyzed by high performance liquid chromatography to find the title compound (91.2% peak area).
(high performance liquid chromatography conditions)
column: YMC ODS A302 (4.6 mm×150 mm)
mobile phase: 25 mM potassium dihydrogen phosphate/acetonitrile (volume ratio: 50/50)
flow rate: 1.0 mL/min
detection: UV 220 nm
temperature: 25° C.

Examples 102-115

The reaction was performed according to the method of Example 101. The results are shown in Table 11.

TABLE 11

| Example | palladium catalyst | ligand | title compound area percentage (%) |
|---|---|---|---|
| 102 | 10% Pd—C(AE) | rac-BINAP | 89.7 |
| 103 | 10% Pd—C(OH) | rac-BINAP | 90.8 |
| 104 | 5% Pd—C(P) | rac-BINAP | 75.7 |
| 105 | 5% Pd—C(B) | rac-BINAP | 44.2 |
| 106 | 10% Pd—C(PE) | DPPE | 77.1 |
| 107 | 10% Pd—C(PE) | DPPB | 77.1 |
| 108 | 10% Pd—C(PE) | DPPP | 78.7 |
| 109 | 10% Pd—C(PE) | DPEphos | 67.2 |
| 110 | 10% Pd—C(PE) | P(o-tol)$_3$ | 44.7 |
| 111 | 10% Pd—C(PE) | PCy$_3$ | 37.6 |
| 112 | 10% Pd—C(AE) | DPPE | 81.2 |

TABLE 11-continued

| Example | palladium catalyst | ligand | title compound area percentage (%) |
|---------|-------------------|--------|-----------------------------------|
| 113 | 10% Pd—C(OH) | DPPE | 77.5 |
| 114 | 10% Pd—C(AE) | DPPF | 87.0 |
| 115 | 10% Pd—C(OH) | DPPB | 77.7 |

Pd—C: palladium carbon
AE, OH, P, B and PE show the kind of palladium carbon (manufactured by N.E. CHEMCAT CORPORATION)
rac-BINAP: racemate of 2,2'-bis(diphenylphosphino)-1,1'-binaphthyl
DPPE: 1,2-bis(diphenylphosphino)ethane
DPPP: 1,3-bis(diphenylphosphino)propane
DPPB: 1,4-bis(diphenylphosphino)butane
DPPF: 1,1'-bis(diphenylphosphino)ferrocene
DPEphos: bis[2-(diphenylphosphino)phenyl]ether
P(o-tol)$_3$: tri(o-tolyl)phosphine
PCy$_3$: tricyclohexylphosphine

Example 116

Synthesis of 2',6'-dimethyl-4'-[3-(methylsulfonyl)propoxy]biphenyl-3-carbaldehyde

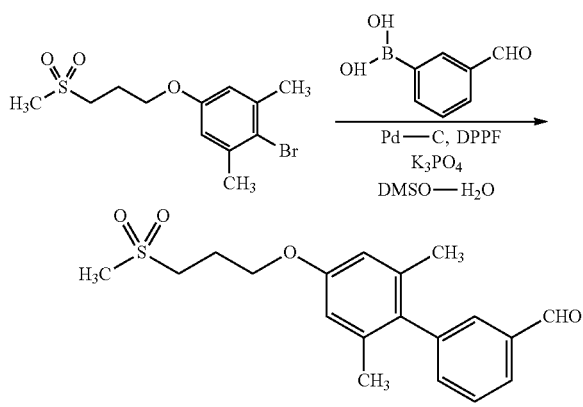

2-Bromo-1,3-dimethyl-5-[3-(methylsulfonyl)propoxy]benzene (50.0 g) and 3-formylphenylboronic acid (24.5 g, 1.05 eq) were dissolved in dimethyl sulfoxide (500 mL), and 10% Pd—C (PE type) (725.0 mg, 0.2 mol %) and 1,1'-bis(diphenylphosphino)ferrocene (171.6 mg, 0.2 mol %) were added. After nitrogen substitution, a deaeration operation was performed under reduced pressure three times, and the mixture was stirred at inside temperature 80±5° C. for 1 hr. A solution of separately prepared tripotassium phosphate (66.1 g, 2.0 eq)/water (250 mL) was added to the reaction mixture at the same temperature, and the mixture was stirred at the same temperature for 4.5 hr. After cooling to 60° C., the mixture was partitioned. To the organic layer was added ethyl acetate (175 mL), and the mixture was cooled to 30° C. Pd—C was filtered off, and washed with ethyl acetate (125 mL). To the filtrate was added 10% brine (300 mL), and the mixture was partitioned. The aqueous layer was extracted with ethyl acetate (300 mL). The organic layers were combined and washed with 10% brine (300 mL×2). The organic layer was concentrated to about 150 mL, to the residue was added ethyl acetate (300 mL), and the mixture was concentrated to about 150 mL. To the residue were added ethyl acetate (250 mL) and activated carbon Shirasagi A (5 g), and the mixture was stirred for 30 min. The activated carbon was filtered off, and washed with ethyl acetate (150 mL). The filtrate was concentrated to about 150 mL, and the mixture was stirred at room temperature overnight. Heptane (750 mL) was added dropwise, and the mixture was stirred at room temperature for 2 hr. The crystals were filtered, and washed with ethyl acetate/heptane (25 mL/125 mL). The crystal was dried at 60° C. under reduced pressure to give the title compound (46.9 g, yield 90.0%).

Example 117

Synthesis of [(3R)-6-({2',6'-dimethyl-4'-[3-(methylsulfonyl)propoxy]biphenyl-3-yl}methoxy)2,3-dihydro-1-benzofuran-3-yl]acetic acid

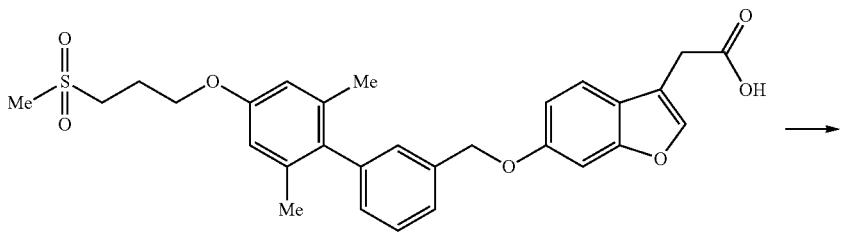

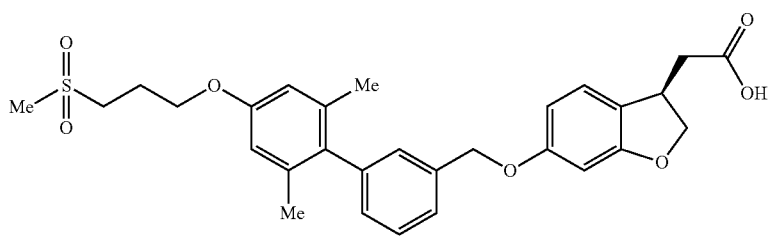

Under a nitrogen atmosphere, in a glove box, [6-({2',6'-dimethyl-4'-[3-(methylsulfonyl)propoxy]biphenyl-3-yl}methoxy)-1-benzofuran-3-yl]acetic acid (52 mg/mL, 0.1 mmol/mL), a solution (1:1, 0.02 mL) of methanol/THF containing triethylamine (0.007 mL/mL, 0.05 mmol/mL), a solution (1:1, 0.01 mL) of methanol/THF containing dichloro-p-cymeneruthenium (II) dimer (2.5 mg/mL, 0.004 mmol/mL) and a solution (1:1, 0.026 mL) of methanol/THF containing optically active ligand (R)-(S)JOSIPHOS (2.5 mg/mL, 0.0038 mmol/mL) were added in a glass microtube. The microtube was introduced into an autoclave and sealed, and the mixture was stirred at 50° C. for 24 hr under a hydrogen atmosphere (1 MPa). The reaction mixture was diluted with a solution (1:1, 1 mL) of normal hexane/isopropylalcohol and analyzed by high performance liquid chromatography to find the title compound (conversion ratio 27%, 41% ee).

(R)—(S)-JOSIPHOS: (R)-1-[(S)-2-(diphenylphosphino)ferrocenyl]ethyldicyclohexylphosphine (high performance liquid chromatography conditions)
column: CHIRALPAK AD-H (manufactured by DAICEL CHEMICAL INDUSTRIES, LTD.)
mobile phase: normal hexane/isopropylalcohol/trifluoroacetic acid (volume ratio: 50/50/0.1)
flow rate: 0.5 mL/min
detection: UV 220 nm
temperature: 30° C.

Examples 118-125

According to the method of Example 117, the reaction was performed using the optically active ligand shown in Table 12. The results are shown in Table 12.

TABLE 12

| Example | liagnd | ee, % | Conv., % | absolute configuration |
|---|---|---|---|---|
| 118 | (R)-(S) Lb1 | 80.2 | 99.6 | R |
| 119 | (R)-(S) Lb2 | 84.2 | 97.4 | R |
| 120 | (S)-(R) Lb3 | 98.0 | 89.7 | S |
| 121 | (R)-(S) Lb4 | 92.2 | 80.1 | R |
| 122 | (R)-(S) Lb5 | 80.3 | 98.7 | R |
| 123 | (R,R) Lb6 | 50.6 | 96.2 | R |
| 124 | (R,R) Lb7 | 85.3 | 100 | S |
| 125 | (R,R) Lb8 | 10.0 | 89.5 | R |

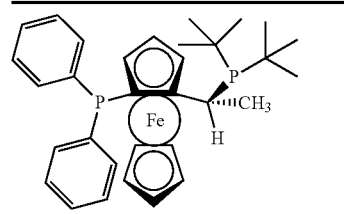

(R)-(S) Lb1

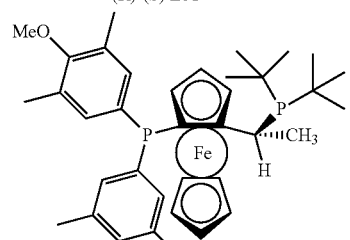

(R)-(S) Lb2

TABLE 12-continued

| Example | liagnd | ee, % | Conv., % | absolute configuration |
|---|---|---|---|---|

(S)-(R) Lb3

(R)-(S) Lb4

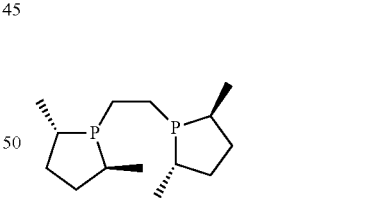

(R)-(S) Lb5

(R,R) Lb6

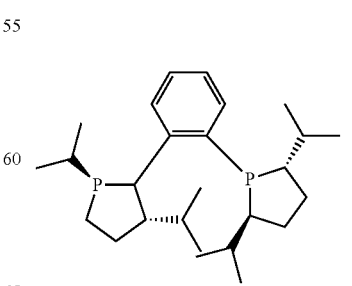

(R,R) Lb7

TABLE 12-continued

| Example | liagnd | ee, % | Conv., % | absolute configuration |
|---------|--------|-------|----------|------------------------|

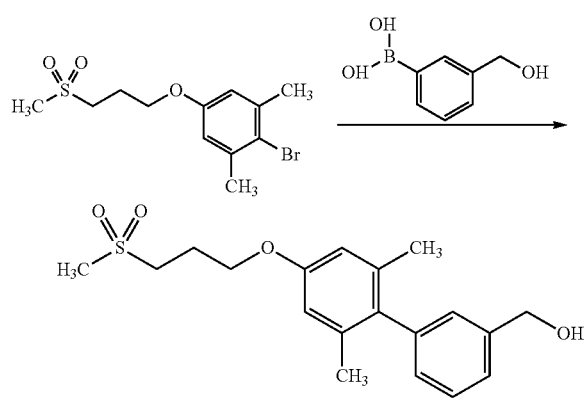

(R,R) Lb8

(R)-(S) Lb1: (R)-1-[(S)-2-(diphenylphosphino)ferrocenyl]ethyldi-tert-butylphosphine
(R)-(S) Lb2: (R)-1-[(S)-2-[bis(4-methoxy-3,5-dimethylphenyl)phosphino]ferrocenyl]ethyldi-tert-butylphosphine
(S)-(R) Lb3: (S)-1-[(R)-2-(di-2-furylphosphino)ferrocenyl]ethyldi-tert-butylphosphine
(R)-(S) Lb4: (R)-1-[(S)-2-(di-p-fluorophenylphosphino)ferrocenyl]ethyldi-tert-butylphosphine
(R)-(S) Lb5: (R)-1-[(S)-2-(di-p-methoxyphenylphophino)ferrocenyl]ethyldi-butylphosphine
(R,R) Lb6 ((R)-Me-BPE): 1,2-bis[(2R,5R)-2,5-dimethylphosphorano]ethane
(R,R) Lb7 ((R)-$^i$Pr-DuPHOS): 1,2-bis[(2R,5R)-2,5-diisopropylphosphorano]benzene
(R,R) Lb8 ((R)-Et-FerroTANE): 1,1'-bis[(2R,4R)-2,4-diethylphosphotano]ferrocene

Example 126

Synthesis of {2',6'-dimethyl-4'-[3-(methylsulfonyl)propoxy]biphenyl-3-yl}methanol 2-Bromo-1,3-dimethyl-5-[3-(methylsulfonyl)propoxy]benzene (1.0 g), 3-hydroxymethylphenylboronic acid (0.497 g, 1.05 eq), triphenylphosphine (65.3 mg, 0.08 eq) and tetrabutylammonium bromide (50.2 mg, 0.05 eq) were dissolved in tetrahydrofuran (12 mL). Tripotassium phosphate (1.98 g, 3 eq) dissolved in water (5 mL) was added, and palladium acetate (14.0 mg) was added under a nitrogen atmosphere. The mixture was stirred under heated reflux for 8 hr. To the reaction mixture was added ethyl acetate (12 mL), and the insoluble material was removed. The filtrate was partitioned, and the organic layer was washed with 10% brine. After treatment with activated carbon, ethanol was added, and the mixture was concentrated is under reduced pressure. To the obtained oil was added ethyl acetate (3 mL), and the oil was dissolved. n-Heptane (10 mL) was added to allow crystallization. The obtained crystals were collected by filtration, and dried to give the title compound (0.893 g).

Example 127

{2',6'-dimethyl-4'-[(3-methylsulfonyl)propoxy]biphenyl-3-yl}methyl methanesulfonate

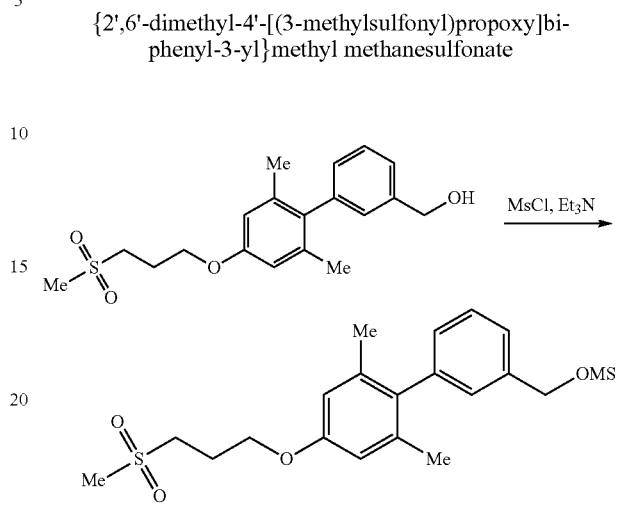

{2',6'-Dimethyl-4'-[3-(methylsulfonyl)propoxy]biphenyl-3-yl}methanol (1.0 g, 2.87 mmol), triethylamine (0.435 g, 4.30 mmol) and tetrahydrofuran (10 mL) were charged, and methanesulfonyl chloride (0.39 g, 3.44 mmol) was added dropwise at 4-9° C. After stirring at 4-9° C. for 1 hr, to the reaction mixture were added water (30 mL) and ethyl acetate (10 mL), and the organic layer was collected by separation. The organic layer was washed with water (10 mL) and concentrated to give a crude product (1.50 g) as a brown oil. Under cooling, the crude product was stood for 4 hr to allow crystallization. Diisopropyl ether was added thereto, and the crystals were pulverized and collected by filtration to give {2',6'-dimethyl-4'-[(3-methylsulfonyl)propoxy]biphenyl-3-yl}methyl methanesulfonate (1.06 g).
$^1$H NMR (300 MHz, CDCl$_3$): δ 2.04 (6H, s), 2.3-2.4 (2H, m), 2.92 (3H, s), 2.96 (3H, s), 3.2-3.3 (2H, m), 4.13 (2H, t, J=5.7 Hz), 5.27 (2H, s)m, 6.65 (2H, s), 7.1-7.2 (2H, m), 7.4-7.5 (2H, m) EI-MS m/e 426 [m$^+$]
elemental analysis: Calcd for C$_{20}$H$_{26}$O$_6$S$_2$: C, 56.32; H, 6.14; S, 15.03. Found: C, 56.33; H, 6.22; S, 14.81.

INDUSTRIAL APPLICABILITY

The present invention provides a production method of an optically active dihydrobenzofuran derivative, which is convenient and has high stereoselectivity. The method is useful for producing a compound having an optically active dihydrobenzofuran ring, which is useful as a drug for the prophylaxis or treatment of diabetes and the like.

This application is based on a patent application No. 2011-032610 filed in Japan, the contents of which are incorporated in full herein.

The invention claimed is:
1. A ruthenium complex represented by the formula:

$$RuCl_2(L)(dmf)_n \qquad (V)$$

wherein L is an optically active form of 1,2-bits(2,5-diisopropylphosphorano)benzene;
dmf is N,N-dimethylformamide; and
n is an integer of one or more.

* * * * *

UNITED STATES PATENT AND TRADEMARK OFFICE
CERTIFICATE OF CORRECTION

PATENT NO. : 8,952,185 B2  
APPLICATION NO. : 13/985395  
DATED : February 10, 2015  
INVENTOR(S) : Mitsuhisa Yamano Page 1 of 1

It is certified that error appears in the above-identified patent and that said Letters Patent is hereby corrected as shown below:

In the Claims

In claim 1, column 138, lines 62-63, "wherein L is an optically active form of 1,2-bits(2,5-diisopropylphosphorano)benzene;", should read --wherein L is an optically active form of 1,2-bis(2,5-diisopropylphosphorano)benzene;--

Signed and Sealed this  
Fourth Day of August, 2015

Michelle K. Lee  
*Director of the United States Patent and Trademark Office*